US010095111B2

(12) United States Patent
Nihashi

(10) Patent No.: US 10,095,111 B2
(45) Date of Patent: Oct. 9, 2018

(54) PATTERN FORMING METHOD, METHOD FOR MANUFACTURING ELECTRONIC DEVICE, AND ELECTRONIC DEVICE

(71) Applicant: FUJIFILM Corporation, Tokyo (JP)

(72) Inventor: Wataru Nihashi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/432,460

(22) Filed: Feb. 14, 2017

(65) Prior Publication Data

US 2017/0153545 A1    Jun. 1, 2017

Related U.S. Application Data

(63) Continuation of application No. PCT/JP2015/072142, filed on Aug. 4, 2015.

(30) Foreign Application Priority Data

Sep. 2, 2014  (JP) ................ 2014-178217

(51) Int. Cl.
| G03F 7/004 | (2006.01) |
| G03F 7/038 | (2006.01) |
| G03F 7/09  | (2006.01) |
| G03F 7/16  | (2006.01) |
| G03F 7/20  | (2006.01) |
| G03F 7/38  | (2006.01) |
| G03F 7/32  | (2006.01) |
| G03F 7/40  | (2006.01) |
| H01L 21/027 | (2006.01) |
| C07C 381/12 | (2006.01) |

(52) U.S. Cl.
CPC ............ G03F 7/038 (2013.01); C07C 381/12 (2013.01); G03F 7/0045 (2013.01); G03F 7/091 (2013.01); G03F 7/16 (2013.01); G03F 7/168 (2013.01); G03F 7/2004 (2013.01); G03F 7/325 (2013.01); G03F 7/38 (2013.01); G03F 7/40 (2013.01); H01L 21/0274 (2013.01)

(58) Field of Classification Search
CPC .......... G03F 7/004; G03F 7/325; G03F 7/038; H01L 21/0274; C07C 381/12
USPC .......................... 430/322, 434, 435, 325, 329
See application file for complete search history.

(56) References Cited

U.S. PATENT DOCUMENTS

| 2005/0008968 A1 | 1/2005 | Watanabe et al. |
| 2010/0009299 A1 | 1/2010 | Watanabe et al. |
| 2012/0077131 A1 | 3/2012 | Enomoto et al. |
| 2012/0183892 A1 | 7/2012 | Watanabe et al. |
| 2012/0183893 A1 | 7/2012 | Watanabe et al. |
| 2013/0035503 A1* | 2/2013 | Oh ................ C07C 309/06 560/138 |
| 2013/0224661 A1 | 8/2013 | Sakakibara et al. |
| 2013/0224666 A1 | 8/2013 | Sakakibara et al. |
| 2013/0230804 A1 | 9/2013 | Sakakibara et al. |
| 2014/0193749 A1 | 7/2014 | Takizawa et al. |
| 2014/0295350 A1 | 10/2014 | Sakakibara et al. |
| 2014/0349221 A1 | 11/2014 | Takizawa et al. |
| 2014/0363758 A1 | 12/2014 | Nihashi et al. |
| 2015/0010855 A1 | 1/2015 | Tsuchimura et al. |
| 2015/0177616 A1 | 6/2015 | Sakakibara et al. |
| 2015/0301451 A1 | 10/2015 | Iwato |
| 2016/0131972 A1* | 5/2016 | Fukushima ........... G03F 7/0045 430/270.1 |
| 2016/0349612 A1* | 12/2016 | Fujiwara ............... C08F 220/38 |
| 2017/0299963 A1* | 10/2017 | Fujiwara ............... G03F 7/0392 |
| 2017/0329227 A1* | 11/2017 | Ohashi .................. G03F 7/0397 |

FOREIGN PATENT DOCUMENTS

| JP | 2002-365802 A | 12/2002 |
| JP | 2004-347738 A | 12/2004 |
| JP | 2011-118419 A | 6/2011 |
| JP | 2011-123469 A | 6/2011 |
| JP | 2013-64986 A | 4/2013 |
| JP | 2013-76991 A | 4/2013 |
| JP | 2013-167826 A | 8/2013 |
| JP | 2013-174715 A | 9/2013 |
| JP | 2013-205520 A | 10/2013 |
| WO | 2011/122336 A1 | 10/2011 |
| WO | 2014/122852 A1 | 8/2014 |

OTHER PUBLICATIONS

Machine Translation of JP 2002-365802 (no date).*
Office Action dated Jul. 11, 2017 by the Japanese Patent Office in counterpart Japanes Patent Application No. 2016-546388.
Translation of Written Opinion dated Sep. 15, 2016 issued by the International Searching Authority in counterpart International Patent Application No. PCT/JP2015/072142 (PCT/ISA/237).
Search Report dated Sep. 15, 2015, issued by the International Searching Authority in counterpart International Patent Application No. PCT/JP2015/072142 (PCT/ISA/210).
Written Opinion dated Sep. 15, 2015, issued by the International Searching Authority in counterpart International Patent Application No. PCT/JP2015/072142 (PCT/ISA/237).
Office Action dated Apr. 5, 2018 by the Korean Intellectual Property Office in counterpart Korean Patent Application No. 10-2017-7004590.
Office Action dated Aug. 3, 2018 in counterpart Korean Patent Application No. 10-2017-7004590.

* cited by examiner

*Primary Examiner* — Amanda C Walke
(74) *Attorney, Agent, or Firm* — Sughrue Mion, PLLC

(57) ABSTRACT

There is provided a pattern forming method including (1) a step of forming a film with an active-light-sensitive or radiation-sensitive resin composition containing the following (A) to (C): (A) a resin having a repeating unit having a phenolic hydroxyl group, and having a group that decomposes by the action of an acid to generate a polar group, (B) a compound that generates an acid upon irradiation with active light or radiation, and (C) a compound having a cationic site and an anionic site in the same molecule, in which the cationic site and the anionic site are linked to each other via a covalent bond; (2) a step of exposing the film; and (3) a step of developing the exposed film using a developer including an organic solvent to form a negative tone pattern.

14 Claims, No Drawings

PATTERN FORMING METHOD, METHOD FOR MANUFACTURING ELECTRONIC DEVICE, AND ELECTRONIC DEVICE

CROSS REFERENCE TO RELATED APPLICATION

This is a continuation of International Application No. PCT/JP2015/072142 filed on Aug. 4, 2015, and claims priority from Japanese Patent Application No. 2014-178217 filed on Sep. 2, 2014, the entire disclosures of which are incorporated herein by reference.

BACKGROUND OF THE INVENTION

1. Field of the Invention

The present invention relates to a pattern forming method, a method for manufacturing an electronic device, and an electronic device. More specifically, the present invention relates to a pattern forming method which is suitable for a process for manufacturing a semiconductor such as an IC, a process for manufacturing a circuit board for a liquid crystal, a thermal head, or the like, and other lithographic processes for photofabrication, a method for manufacturing an electronic device, and an electronic device.

2. Description of the Related Art

Since a resist for a KrF excimer laser (248 nm) was developed, a pattern forming method using chemical amplification has been used in order to complement desensitization caused by light absorption. For example, in a positive tone chemical amplification, a photoacid generator included in an exposed area first decomposes by irradiation with light to generate an acid. Further, during a post exposure bake (PEB) process or the like, an alkali-insoluble group included in a photosensitive composition is changed to an alkali-soluble group by the catalytic action of an acid thus generated. Thereafter, development is carried out by using, for example, an alkaline solution. Thus, the exposed area is removed to obtain a desired pattern.

In the method, various alkaline developers have been suggested as the alkaline developer. For example, a water-based alkaline developer with 2.38% by mass of tetramethylammonium hydroxide (aqueous TMAH solution) is universally used as the alkaline developer.

Moreover, in order to make semiconductor elements finer, the wavelength of a light source for exposure has been shortened and a projection lens with a high numerical aperture (high NA) has been advanced. Currently, an exposure machine using an ArF excimer laser having a wavelength of 193 nm as a light source has been developed. As a technique for further improving resolving power, a method (that is, a liquid immersion method) in which a liquid having a high refractive index (hereinafter also referred to as an "immersion liquid") is charged between a projection lens and a sample has been proposed. In addition, EUV lithography in which exposure is carried out with ultraviolet rays at a shorter wavelength (13.5 nm) has also been proposed.

Moreover, recently, a pattern forming method using a developer (organic developer) including an organic solvent has also been developed (see, for example, JP2011-123469A and WO2011/122336A). For example, JP2011-123469A and WO2011/122336A each disclose a pattern forming method including a step of coating a substrate with a resist composition whose solubility in an organic developer is reduced upon irradiation with active light or radiation, an exposing step, and a step of carrying out development using an organic developer. It is considered that according to these methods, it is possible to stably form a fine pattern with high accuracy.

In addition, JP2013-174715A discloses a pattern forming method including forming a film using a resist composition including a resin having a phenolic hydroxyl group, tetrabutylammonium hydroxide, and carrying out development with an organic developer.

SUMMARY OF THE INVENTION

However, good pattern shapes have been obtained by the above pattern forming methods in the related art, using a developer including an organic solvent, but particularly for formation of an ultrafine pattern (for example, having a line width of 50 nm or less), there has been a demand for suppression of line width roughness (LWR) performance, suppression of development defects, and further improvement of a pattern shape.

It is an object of the present invention to provide a pattern forming method which can accomplish all of line width roughness performance, suppression of development defects, and pattern shapes to extremely high levels, in particular, in formation of an ultrafine pattern (for example, having a line width of 50 nm or less). It is another object of the present invention to provide a method for manufacturing an electronic device including the pattern forming method, and an electronic device manufactured by this manufacturing method.

That is, the present invention is as follows.

<1> A pattern forming method comprising:
(1) a step of forming a film with an active-light-sensitive or radiation-sensitive resin composition containing the following (A) to (C):
(A) a resin having a repeating unit having a phenolic hydroxyl group, and having a group that decomposes by the action of an acid to generate a polar group,
(B) a compound that generates an acid upon irradiation with active light or radiation, and
(C) a compound having a cationic site and an anionic site in the same molecule, in which the cationic site and the anionic site are linked to each other via a covalent bond,
(2) a step of exposing the film, and
(3) a step of developing the exposed film using a developer including an organic solvent to form a negative tone pattern.

<2> The pattern forming method as described in <1>, in which the compound (C) is a compound represented by the following General Formula (C-1).

$$(Rx)_{n2}\text{-}X^{\oplus}\text{-}L\text{-}A^{\ominus} \qquad (C\text{-}1)$$

$A^-$ represents an organic acid anion, L represents a single bond or a divalent linking group, and $X^+$ represents a nitrogen cation, a sulfur cation, or an iodine cation.

Rx represents an alkyl group, a cycloalkyl group, an aryl group, an aralkyl group, or a heterocyclic group. In a case where Rx's are present in plural numbers, a plurality of Rx's may be the same as or different from each other. Further, in a case where Rx's are present in plural numbers, a plurality of Rx's may be bonded to each other to form a ring, and a ring thus formed may have a nitrogen atom, an oxygen atom, or a sulfur atom as a ring member.

In a case where $X^+$ represents a nitrogen cation, n2 represents 3, in a case where $X^+$ represents a sulfur cation, n2 represents 2, and in a case where $X^+$ represents an iodine cation, n2 represents 1.

<3> The pattern forming method as described in <2>, in which A⁻ represents a carboxylate anion.

<4> The pattern forming method as described in <2> or <3>, in which X⁺ represents a nitrogen cation.

<5> The pattern forming method as described in any one of <2> to <4>, in which Rx represents an alkyl group.

<6> The pattern forming method as described in any one of <2> to <5>, in which at least one of n2 Rx's has 3 or more carbon atoms.

<7> The pattern forming method as described in any one of <2> to <6>, in which the number of carbon atoms present between X⁺ and the element having negative charge among the elements constituting A⁻ is 5 or less.

<8> The pattern forming method as described in any one of <1> to <7>, in which the content of the compound (C) is 5% by mass or less with respect to the total solid content of the active-light-sensitive or radiation-sensitive resin composition.

<9> A method for manufacturing an electronic device, comprising the pattern forming method as described in any one of <1> to <8>.

<10> An electronic device manufactured by the method for manufacturing an electronic device as described in <9>.

According to the present invention, it is possible to provide a pattern forming method which can accomplish all of line width roughness performance, suppression of development defects, and pattern shapes to extremely high levels, in particular, in formation of an ultrafine pattern (for example, having a line width of 50 nm or less). Further, according to the present invention, it is also possible to provide a method for manufacturing an electronic device including the pattern forming method, and an electronic device manufactured by this manufacturing method.

DESCRIPTION OF THE PREFERRED EMBODIMENTS

Hereinafter, embodiments of the present invention will be described in detail.

In citations for a group (an atomic group) in the present specification, in a case where a group is denoted without specifying whether it is substituted or unsubstituted, the group denoted without specifying whether it is substituted or unsubstituted includes both a group not having a substituent and a group having a substituent. For example, an "alkyl group" includes not only an alkyl group not having a substituent (unsubstituted alkyl group), but also an alkyl group having a substituent (substituted alkyl group).

"Active light" or "radiation") in the present specification means, for example, a bright line spectrum of a mercury lamp, far ultraviolet rays represented by an excimer laser, extreme ultraviolet rays (EUV light), X-rays, electron beams (EB), or the like. In addition, in the present invention, light means active light or radiation.

Unless otherwise specified, "exposure" in the present specification includes not only exposure by a mercury lamp, far ultraviolet rays represented by an excimer laser, extreme ultraviolet rays (EUV light), X-rays, or the like, but also writing by particle rays such as electron beams and ion beams.

In the present specification, a "(meth)acryl-based monomer" means at least one of monomer having a structure of "$CH_2=CH-CO-$" or "$CH_2=C(CH_3)-CO-$". Similarly, "(meth)acrylate" and "(meth)acrylic acid" mean "at least one of acrylate or methacrylate" and "at least one of acrylic acid or methacrylic acid", respectively.

In the present specification, the weight-average molecular weight of a resin is a value in terms of polystyrene, measured by a GPC method. GPC can be performed in accordance with a method using HLC-8120 (manufactured by Tosoh Corporation), TSK gel Multipore HXL-M (manufactured by Tosoh Corporation, 7.8 mmID×30.0 cm) as a column, and tetrahydrofuran (THF) or N-methyl-2-pyrrolidone (NMP) as an eluant.

The pattern forming method of the present invention includes:

(1) a step of forming a film with an active-light-sensitive or radiation-sensitive resin composition (simply also referred to as a "composition") containing the following (A) to (C):

(A) a resin having a group that decomposes by the action of an acid to generate a polar group, which contains a repeating unit having a phenolic hydroxyl group, (B) a compound that generates an acid upon irradiation with active light or radiation, and (C) a compound having a cationic site and an anionic site in the same molecule, in which the cationic site and the anionic site are linked to each other via a covalent bond;

(2) a step of exposing the film; and (3) a step of developing the exposed film using a developer (also referred to as an "organic developer") including an organic solvent to form a negative tone pattern.

According to the present invention, it is possible to provide a pattern forming method, by which LWR is small, development defects are fewer, and pattern shapes are excellent, a method for manufacturing an electronic device, and an electronic device.

The reason therefor is not clear, but is presumed to be as follows.

For example, a compound (salt) in which a cationic site and an anionic site interact with each other through an ion bond, such as tetrabutylammonium hydroxide, interacts with a phenolic hydroxyl group of the resin (A), and the resin (A) is hardly dissolved in the developer including an organic solvent. However, it is thought that since the compound (C) in the present invention is a compound (molecular inner salt) having a cationic site and an anionic site in the same molecule, in which the cationic site and the anionic site are linked to each other via a covalent bond, it is difficult that the compound (C) interacts with a phenolic hydroxyl group of the resin (A), accordingly, problems as described above do not occur, and therefore, all of line width roughness performance, suppression of development defects, and pattern shapes can be accomplished to extremely high levels.

The pattern forming method of the present invention preferably further includes a step (4) of carrying out rinsing using a rinsing liquid including an organic solvent.

The rinsing liquid is preferably a rinsing liquid containing at least one organic solvent selected from the group consisting of a hydrocarbon-based solvent, a ketone-based solvent, an ester-based solvent, an alcohol-based solvent, an amide-based solvent, and an ether-based solvent.

The pattern forming method of the present invention preferably includes a heating step (5) after the exposing step (2).

Furthermore, the resin (A) is also a resin in which the polarity is enhanced by the action of an acid, and the solubility in an alkaline developer is enhanced. Accordingly, the pattern forming method of the present invention may further include a step (6) of carrying out development using an alkaline developer.

The pattern forming method of the present invention may include the exposing step (2) in plural times.

the pattern forming method of the present invention may include the heating step (5) in plural times.

Hereinafter, the pattern forming method of the present invention will be described in detail.

<Pattern Forming Method>

The pattern forming method according to the present invention includes forming a film (resist film) using the composition of the step (1), (2) exposing the film with active light or radiation, and (3) developing the exposed film using an organic developer. It is preferable that this method further includes (4) rinsing the developed film using a rinsing liquid since the effects of the present invention are more excellent.

After forming the film, a prebake (PB) step is also preferably included before the exposing step. In addition, a post exposure bake (PEB) step is also preferably included after the exposing step and before the developing step.

Both the PB step and the PEB step are preferably carried out at a heating temperature of 40° C. to 130° C., more preferably 50° C. to 120° C., and still more preferably 60° C. to 120° C. In particular, in a case where the PEB step is carried out at a low temperature of 60° C. to 90° C., exposure latitude (EL) and resolving power can be significantly improved.

Furthermore, the heating time is preferably 30 to 300 seconds, more preferably 30 to 180 seconds, and still more preferably 30 to 90 seconds.

In the pattern forming method according to the present invention, the step of forming the film on a substrate, using the composition, the step of exposing the film, the heating step, and the developing step can be carried out by a generally known method.

The light source used for the exposure is preferably extreme ultraviolet rays (EUV light) or electron beams (EB).

The film formed using the composition according to the present invention may also be subjected to liquid immersion exposure. Thus, the resolution can further be improved. As the liquid immersion medium to be used, any medium having a higher refractive index than that of air can be used, but is preferably pure water.

In this case, a hydrophobic resin may also be added to the composition in advance, or after forming a film, a top coat may also be provided of the film. Further, the performance required for the top coat and the method for using the top coat are described in Chapter 7 of "Process and Material for Liquid Immersion Lithography" published by CMC Publishing Co., Ltd.

When the top coat is peeled after the exposure, a developer may be used or an additional peeling agent may also be used. As the peeling agent, a solvent having a little permeation into a film is preferable. In view that a peeling step can be carried out at the same time with a step for a film developing treatment, it is preferable that the top coat can be peeled by a developer.

In the present invention, the substrate on which the film is formed is not particularly limited. As the substrate, a substrate which is generally used in a process for manufacturing a semiconductor such as an IC, in a process for manufacturing a circuit board for a liquid crystal, a thermal head or the like, and in other lithographic processes of photofabrication can be used. Examples of the substrate include an inorganic substrate such as silicon, SiN, and $SiO_2$, and a coating type inorganic substrate such as SOG. Further, if desired, an organic antireflection film may be formed between the film and the substrate.

Examples of the organic developer include developers including polar solvents such as a ketone-based solvent, an ester-based solvent, an alcohol-based solvent, an amide-based solvent, and an ether-based solvent, and a hydrocarbon-based solvent. Further, a mixed solvent thereof may also be used.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methylisobutyl ketone, methyl amyl ketone (2-heptanone), acetylacetone, acetonylacetone, ionone, diacetonyl alcohol, acetylcarbinol, acetophenone, methyl naphthyl ketone, isophorone, and propylene carbonate.

Examples of the ester-based solvent include butyl butyrate, methyl acetate, butyl acetate, ethyl acetate, isopropyl acetate, amyl acetate, isoamyl acetate, n-pentyl acetate, propylene glycol monomethyl ether acetate, propylene glycol monoethyl ether acetate, ethylene glycol monoethyl ether acetate, diethylene glycol monobutyl ether acetate, diethylene glycol monoethyl ether acetate, ethyl-3-ethoxypropionate, 3-methoxybutylacetate, 3-methyl-3-methoxybutylacetate, methyl formate, ethyl formate, butyl formate, propyl formate, ethyl lactate, butyl lactate, propyl lactate, methyl propionate, methyl 3-methoxypropionate (MMP), ethyl propionate, ethyl 3-ethoxypropionate (EEP), and propyl propionate. Particularly, butyl butyrate, alkyl acetate esters such as methyl acetate, butyl acetate, ethyl acetate, isopropyl acetate, and amyl acetate, or alkyl propionate esters such as methyl propionate, ethyl propionate, and propyl propionate are preferable.

Examples of the alcohol-based solvent include alcohols such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol and n-decanol; glycols such as ethylene glycol, diethylene glycol, and triethylene glycol; and glycol ethers such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol.

Examples of the ether-based solvent includes dioxane and tetrahydrofuran, in addition to the glycol ethers.

Examples of the amide-based solvent include N-methyl-2-pyrrolidone, N,N-dimethylacetamide, N,N-dimethylformamide, hexamethylphosphoric triamide, and 1,3-dimethyl-2-imidazolidinone.

Examples of the hydrocarbon-based solvent include aromatic hydrocarbon-based solvents such as toluene, xylene, and anisole, and aliphatic hydrocarbon-based solvents such as pentane, hexane, octane, and decane.

The above solvent is used by mixing two or more thereof or used by mixing the solvent with other solvent(s) and/or water in a range in which sufficient performance can be exhibited. Here, the moisture content in the whole volume of the developer is preferably less than 10% by mass, but a developer having substantially no moisture is more preferable. That is, this developer is preferably a developer that is composed substantially only of organic solvents.

Incidentally, even in this case, the developer can include a surfactant which will be described later. Further, the organic developer may include a basic compound. Specific examples and preferred examples of the basic compound that can be included in the organic developer are the same ones as for the basic compound that can be included in the active-light-sensitive or radiation-sensitive resin composition which will be described later. Further, in this case, in this case, the developer may include inevitable impurities derived from atmosphere.

The amount of the organic solvent to be used with respect to the developer is preferably from 80% by mass to 100% by mass, more preferably from 90% by mass to 100% by mass, and still more preferably from 95% by mass to 100% by mass, with respect to the total amount of the developer.

In particular, the organic solvent included in the developer is preferably at least one selected from a ketone-based solvent, an ester-based solvent, an alcohol-based solvent, an amide-based solvent, or an ether-based solvent.

The vapor pressure of the organic developer is preferably 5 kPa or less, more preferably 3 kPa or less, and particularly preferably 2 kPa or less at 20° C. By setting the vapor pressure of the developer to 5 kPa or less, evaporation of the developer on the substrate or in a development cup is suppressed, the temperature evenness in the wafer surface is improved, and as a result, the dimensional evenness in the wafer surface is improved.

Specific examples of the developer having a vapor pressure of 5 kPa or less include ketone-based solvents such as 1-octanone, 2-octanone, 1-nonanone, 2-nonanone, 4-heptanone, 2-hexanone, diisobutyl ketone, cyclohexanone, methyl cyclohexanone, phenyl acetone, and methyl isobutyl ketone; ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, butyl butyrate, ethyl lactate, butyl lactate, and propyl lactate; alcohol-based solvents such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; glycol-based solvents such as ethylene glycol, diethylene glycol, and triethylene glycol; glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; ether-based solvents such as tetrahydrofuran; amide-based solvents such as N-methyl-2-pyrrolidone, N,N-dimethyl acetamide, and N,N-dimethyl formamide; aromatic hydrocarbon-based solvents such as toluene and xylene; and aliphatic hydrocarbon-based solvents such as octane and decane.

Specific examples of the developer having a vapor pressure of 2 kPa or less include ketone-based solvents such as 1-octanone, 2-octanone, 1-nonanone, 2-nonanone, 4-heptanone, 2-hexanone, diisobutyl ketone, cyclohexanone, methyl cyclohexanone, and phenyl acetone; ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate, and propyl lactate; alcohol-based solvents such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; glycol-based solvents such as ethylene glycol, diethylene glycol, and triethylene glycol; glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; amide-based solvents such as N-methyl-2-pyrrolidone, N,N-dimethyl acetamide, and N,N-dimethyl formamide; aromatic hydrocarbon-based solvents such as xylene; and aliphatic hydrocarbon-based solvents such as octane and decane.

An appropriate amount of a surfactant can be added to the developer, if necessary.

The surfactant is not particularly limited, and for example, ionic or non-ionic fluorine-based and/or silicon-based surfactants, or the like can be used. Examples of the fluorine- and/or the silicon-based surfactant include the surfactants described in JP1987-36663A (JP-S62-36663A), JP1986-226746A (JP-S61-226746A), JP1986-226745A (JP-S61-226745A), JP1987-170950A (JP-S62-170950A), JP1988-34540A (JP-S63-34540A), JP1995-230165A (JP-H07-230165A), JP1996-62834A (JP-H08-62834A), JP1997-54432A (JP-H09-54432A), JP1997-5988A (JP-H09-5988A), U.S. Pat. No. 5,405,720A, U.S. Pat. No. 5,360,692A, U.S. Pat. No. 5,529,881A, U.S. Pat. No. 5,296,330A, U.S. Pat. No. 5,436,098A, U.S. Pat. No. 5,576,143A, U.S. Pat. No. 5,294,511A, and U.S. Pat. No. 5,824,451A. The surfactant is preferably a non-ionic surfactant. The non-ionic surfactant is not particularly limited, but a fluorine-based surfactant or a silicon-based surfactant is more preferably used.

Furthermore, the amount of the surfactant to be added is usually 0.001% to 5% by mass, preferably 0.005% to 2% by mass, and more preferably 0.01% to 0.5% by mass, with respect to the total amount of the developer.

Examples of the developing method include a method in which a substrate is immersed in a tank filled with a developer for a certain period of time (a dip method), a method in which a developer is heaped up to the surface of a substrate by surface tension and developed by stopping for a certain period of time (a paddle method), a method in which a developer is sprayed on the surface of a substrate (a spray method), and a method in which a developer is continuously discharged on a substrate rotated at a constant rate while scanning a developer discharging nozzle at a constant rate (a dynamic dispense method).

In a case where the various developing methods include a step of discharging a developer toward a resist film from a developing nozzle of a developing device, the discharge pressure of the developer discharged (the flow velocity per unit area of the developer discharged) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of a throughput.

By setting the discharge pressure of a developer to be discharged to be within the above range, the defects of the pattern resulting from a resist residue after development can be significantly reduced.

Although details on the mechanism are not clear, it is thought to be due to a fact that the pressure imposed on the resist film by the developer is decreased by setting the discharge pressure to the above range so that the composition film and/or the pattern are inhibited from being inadvertently cut or collapsing.

Moreover, the discharge pressure (mL/sec/mm$^2$) of the developer is the value at the outlet of the development nozzle in the developing device.

Examples of the method for adjusting the discharge pressure of the developer include a method of adjusting the discharge pressure by a pump or the like, and a method of supplying a developer from a pressurized tank and adjusting the pressure to change the discharge pressure.

In addition, after the step of carrying out development, a step of stopping the development while replacing the solvent with another solvent may also be carried out.

The pattern forming method according to the present invention preferably further includes a rinsing step (a step of rinsing a film using a rinsing liquid including an organic solvent) after the developing step.

The rinsing liquid used in the rinsing step is not particularly limited as long as it does not dissolve the pattern after development, and a solution including a general organic solvent can be used.

Examples of the rinsing liquid include a rinsing liquid including at least one kind of organic solvent selected from a hydrocarbon-based solvent, a ketone-based solvent, an ester-based solvent, an alcohol-based solvent, an amide-based solvent, or an ether-based solvent. The rinsing liquid more preferably includes at least one kind of organic solvent selected from a ketone-based solvent, an ester-based solvent, an alcohol-based solvent, or an amide-based solvent, and still more preferably includes an alcohol-based solvent or an ester-based solvent.

The rinsing liquid more preferably includes a monohydric alcohol, and still more preferably includes a monohydric alcohol having 5 or more carbon atoms.

These monohydric alcohols may be linear, branched, or cyclic. Examples of these monohydric alcohols include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol. Examples of the monohydric alcohol having 5 or more carbon atoms include 1-hexanol, 2-hexanol, 4-methyl-2-pentanol, 1-pentanol, and 3-methyl-1-butanol.

Furthermore, the rinsing liquid is also preferably a hydrocarbon having 11 or more carbon atoms, and more preferably a hydrocarbon having 11 to 14 carbon atoms.

The respective components as described above may be used in mixture with two or more kinds thereof, and may be used in mixture with an organic solvent other than the components.

The moisture content of the rinsing liquid is preferably less than 10% by mass, more preferably less than 5% by mass, and still more preferably less than 3% by mass. That is, the amount of an organic solvent to be used with respect to the rinsing liquid is preferably from 90% by mass to 100% by mass, more preferably from 95% by mass to 100% by mass, and still more preferably from 97% by mass to 100%, with respect to the total amount of the rinsing liquid. When the moisture content of the rinsing liquid is less than 10% by mass, more favorable development characteristics can be accomplished.

The vapor pressure of the rinsing liquid is preferably from 0.05 kPa to 5 kPa, more preferably from 0.1 kPa to 5 kPa, and still more preferably from 0.12 kPa to 3 kPa, at 20° C. By setting the vapor pressure of the rinsing liquid to a range from 0.05 kPa to 5 kPa, the temperature evenness in the wafer surface is improved, swelling due to permeation of the rinsing liquid is suppressed, and the dimensional evenness in the wafer surface is improved.

Moreover, a suitable amount of a surfactant may be added to the rinsing liquid.

In the rinsing step, the developed wafer is rinsed with the rinsing liquid. The method for the rinsing treatment is not particularly limited, and examples thereof include a method in which a rinsing liquid is discharged continuously onto a substrate while the wafer is rotated at a constant rate (a spin coating method), a method in which a wafer is immersed in a tank filled with a rinsing liquid for a certain period of time (a dipping method), and a method in which a rinsing liquid is sprayed onto the surface of a substrate (a spray method). Among these, it is preferable that after carrying out a washing treatment by the spin coating method, a rinsing liquid is removed from the substrate by rotating the substrate at a rotation speed of 2,000 rpm to 4,000 rpm.

The pattern forming method of the present invention can further include a step of forming a resist pattern by carrying out development using an aqueous alkaline solution (alkaline developing step). Due to this combination, a finer pattern can be formed.

In the present invention, an area with low exposure intensity is removed in the organic solvent developing step, and by further carrying out the alkaline developing step, an area with high exposure intensity is also removed. By virtue of a multiple development process in which development is carried out a plurality of times in this way, a pattern can be formed by keeping only a region with an intermediate exposure intensity from being dissolved, so that a finer pattern than usual can be formed (the same mechanism as in [0077] of JP2008-292975A).

The alkaline development can be carried out before and/or after carrying out development using a developer including an organic solvent, but is more preferably carried out before the organic solvent developing step.

The type of the alkaline developer is not particularly limited, but an aqueous tetramethylammonium hydroxide solution is usually used. An appropriate amount of alcohols or a surfactant may be added to the alkaline developer.

The alkali concentration of alkaline developer is usually 0.1% to 20% by mass. The pH of the alkaline developer is usually 10.0 to 15.0. As the alkaline developer, an aqueous solution with 2.38% by mass of tetramethylammonium hydroxide is particularly preferably used.

In a case of carrying out a rinsing treatment after development using an alkaline developer, pure water is typically used as the rinsing liquid. An appropriate amount of a surfactant may be added to the rinsing liquid.

Generally, a pattern obtained by the pattern forming method of the present invention is suitably used as an etching mask or the like of a semiconductor device, but can also be used in other applications. Examples of such other applications include applications for guide pattern formation in Directed Self-Assembly (DSA) (see, for example, ACS Nano, Vol. 4, No. 8, pp. 4815-4823), that is, a so-called core material (core) in a spacer process (see, for example, JP1991-270227A (JP-H03-270227A) and JP2013-164509A).

Moreover, the present invention relates to a method of manufacturing an electronic device, including the pattern forming method of the present invention as described above, and an electronic device manufactured by this manufacturing method.

The electronic device of the present invention is suitably mounted on electric or electronic equipment (home electronics, OA/media-related equipment, optical equipment, telecommunication equipment, and the like).

<Active-Light-Sensitive or Radiation-Sensitive Resin Composition>

Hereinafter, the active-light-sensitive or radiation-sensitive resin composition which can be used in the present invention will be described.

The active-light-sensitive or radiation-sensitive resin composition according to the present invention is used for negative tone development (development in which when the composition is exposed, its solubility in a developer is reduced, and thus, an exposed area remains as a pattern and an unexposed area is removed). That is, the active-light-sensitive or radiation-sensitive resin composition according to the present invention can be suitably used as an active-light-sensitive or radiation-sensitive resin composition for organic solvent development, which is used for development using a developer including an organic solvent. Here, the use for an organic solvent development means an application of the composition to be supplied to a step of carrying out development using a developer including an organic solvent.

As such, the present invention also relates to an active-light-sensitive or radiation-sensitive resin composition which is provided for the pattern forming method of the present invention.

The active-light-sensitive or radiation-sensitive resin composition of the present invention is typically a resist composition, and is preferably a negative tone resist composition (that is, a resist composition for organic solvent development), particularly in view that good effects can be obtained. Further, the composition according to the present invention is a typically a chemical amplification type resist composition.

The composition used in the present invention contains (A) a resin having a repeating unit having a phenolic hydroxyl group, and having a group that decomposes by the action of an acid to generate a polar group.

[(A) Resin Having Repeating Unit Having Phenolic Hydroxyl Group, and Having Group that Decomposes by Action of Acid to Generate Polar Group]

The (A) resin having a repeating unit having a phenolic hydroxyl group, and having a group that decomposes by the action of an acid to generate a polar group (also referred to as a "resin (A)") is a resin whose solubility in an organic solvent is reduced by the action of an acid.

Moreover, in the present invention, the "phenolic hydroxyl group" is a generic term that includes not only "a phenol in a narrow sense" formed by substituting a hydrogen atom in a benzene ring with a hydroxyl group (—OH group) but also "phenol in a broad sense" formed by substituting a hydrogen atom in the structure of an aromatic ring such as a naphthalene ring with a hydroxyl group (—OH group), in which the hydroxyl group exhibits acidic properties.

The resin (A) has a repeating unit having a phenolic hydroxyl group. Examples of the repeating unit having a phenolic hydroxyl group include a repeating unit represented by the following General Formula (I').

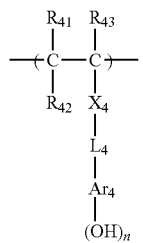

(I')

In General Formula (I'), $R_{41}$, $R_{42}$, and $R_{43}$ each independently represent a hydrogen atom, an alkyl group, a halogen atom, a cyano group, or an alkoxycarbonyl group. Here, $R_{42}$ may be bonded to $Ar_4$ to form a ring, and $R_{42}$ in this case represents a single bond or an alkylene group. $X_4$ represents a single bond, —COO—, or —CONR$_{64}$—, and in the case of forming a ring with $R_{42}$, represents a trivalent linking group. $R_{64}$ represents a hydrogen atom or an alkyl group. $L_4$ represents a single bond or an alkylene group. $Ar_4$ represents an (n+1)-valent aromatic ring group, and in the case of being bonded to $R_{42}$ to form a ring, represents an (n+2)-valent aromatic ring group. n represents an integer of 1 to 4.

Specific examples of the alkyl group, the cycloalkyl group, the halogen atom, and the alkoxycarbonyl group, represented by each of $R_{41}$, $R_{42}$, and $R_{43}$ in General Formula (I'), or the substituents which these groups may have are the same as those described for each of the groups represented by $R_{51}$, $R_{52}$, and $R_{53}$ in General Formula (V) which will be described later.

$Ar_4$ represents an (n+1)-valent aromatic ring group. The divalent aromatic ring group in a case where n is 1 may have a substituent, and preferable examples thereof include arylene groups having 6 to 18 carbon atoms, such as a phenylene group, a tolylene group, a naphthylene group, and an anthracenylene group, and aromatic ring groups including a hetero ring, such as thiophene, furan, pyrrole, benzothiophene, benzofuran, benzopyrrole, triazine, imidazole, benzimidazole, triazole, thiadiazole, and thiazole.

Suitable specific examples of the (n+1)-valent aromatic ring group in a case where n is an integer of 2 or more include a group obtained by excluding arbitrary (n−1) hydrogen atoms from a specific example described above of the divalent aromatic ring group.

The (n+1)-valent aromatic ring group may further have a substituent.

Examples of the substituent which the alkyl group, the cycloalkyl group, the alkoxycarbonyl group, the alkylene group, or the (n+1)-valent aromatic ring group as described above can have include alkoxy groups such as an alkyl group, a methoxy group, an ethoxy group, a hydroxyethoxy group, a propoxy group, a hydroxypropoxy group, and a butoxy group, and aryl groups such as a phenyl group, represented by each of $R_{51}$ to $R_{53}$ in General Formula (V) which will be described later.

Examples of the alkyl group represented by $R_{64}$ in —CONR$_{64}$— ($R_{64}$ represents a hydrogen atom or an alkyl group) represented by $X_4$ are the same as the alkyl group represented by each of $R_{61}$ to $R_{63}$ in General Formula (V) which will be described later.

$X_4$ is preferably a single bond, —COO—, or —CONH—, and more preferably a single bond or —COO—.

Examples of the alkylene group in $L_4$ include an alkylene group having 1 to 8 carbon atoms, such as a methylene group, an ethylene group, a propylene group, a butylene group, a hexylene group, and an octylene group, which preferably may have a substituent.

$Ar_4$ is particularly preferably an aromatic ring group having 6 to 18 carbon atoms which may have a substituent, and particularly preferably a benzene ring group, a naphthalene ring group, or a biphenylene ring group.

The repeating unit represented by General Formula (I') preferably has a hydroxystyrene structure. That is, $Ar_4$ is preferably a benzene ring group.

$X_4$ or $L_4$ in General Formula (I') is preferably a single bond.

Specific examples of the repeating unit represented by General Formula (I') will be described below, but the present invention is not limited thereto. In the formula, a represents 1 or 2.

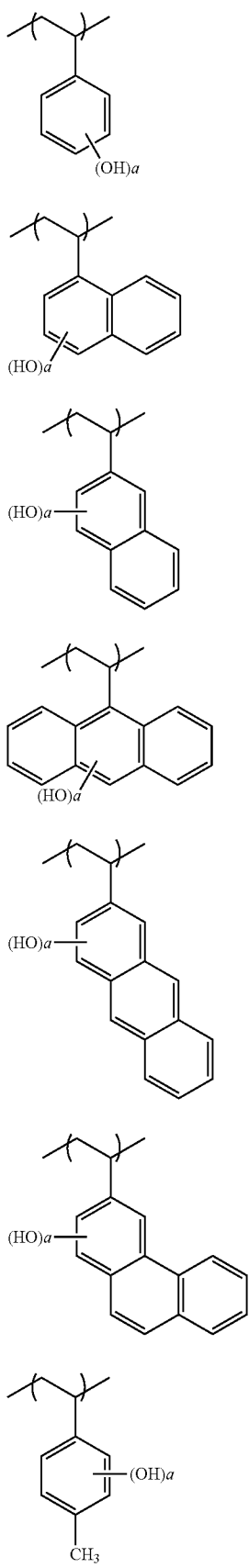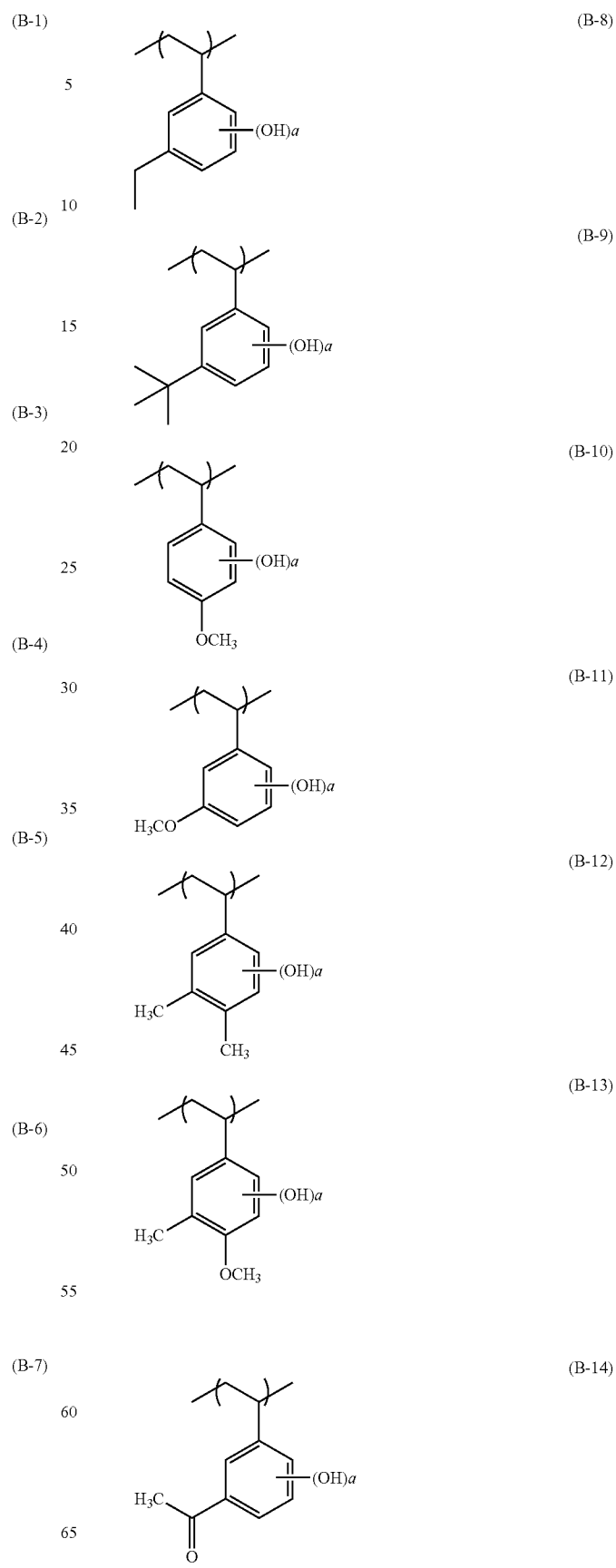

(B-15)
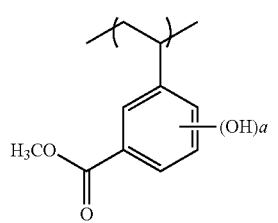
(B-16)
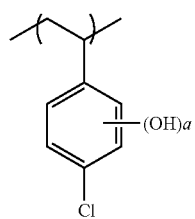
(B-17)
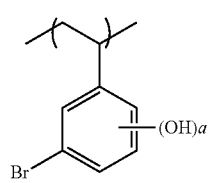
(B-18)
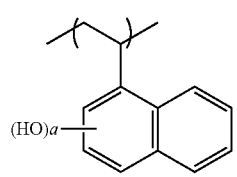
(B-19)
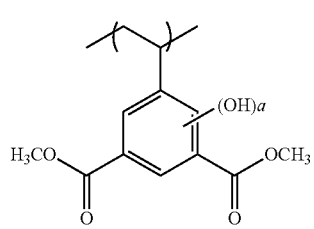
(B-20)
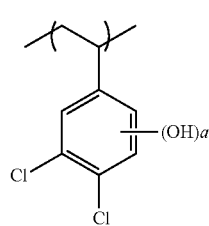
(B-21)
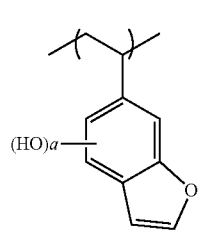
(B-22)
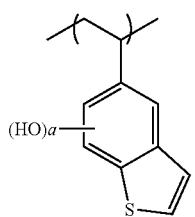
(B-23)
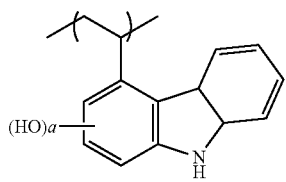
(B-24)
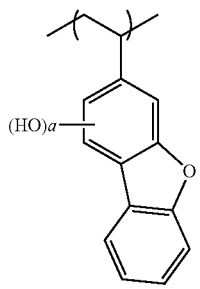
(B-25)
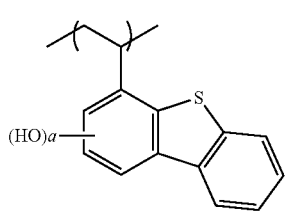
(B-26)
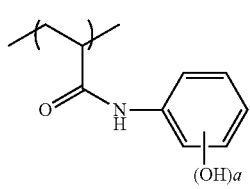
(B-27)
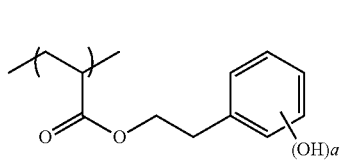
(B-28)
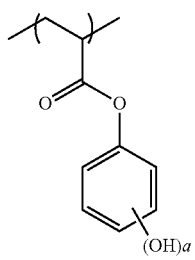

-continued

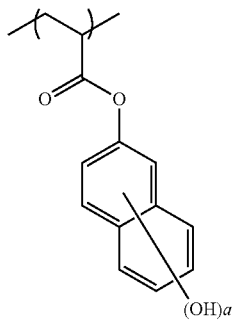
(B-29)

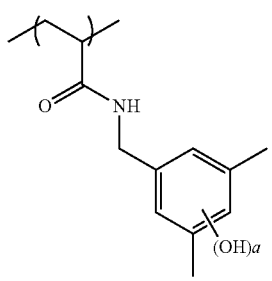
(B-30)

The resin (A) may include two or more kinds of repeating unit (I').

The content of the repeating unit (I') in the resin (A) is preferably large from the viewpoint of enhancing the sensitivity by the increase in the secondary electron generation amount at the time of exposure described above and strengthening of an interaction with the additive in the present invention, and the content should not be so great from the viewpoint of ensuring the contrast by increasing the amount of the repeating units (a) having an acid-decomposable group. For this reason, the content of the repeating unit (I') in the resin (A) is preferably 5% to 80% by mole, more preferably 10% to 80% by mole, still more preferably 20% to 70% by mole, and particularly preferably 30% to 60% by mole, with respect to all the repeating units in the resin (A).

The resin (A) has a group that decomposes by the action of an acid to generate a polar group. When the resin (A) has the group, it exhibits a property that he solubility in an organic solvent is reduced by the action of an acid.

Moreover, the repeating unit having a group (acid-decomposable group) which generates a polar group by being decomposed due to the action of an acid is referred to as "repeating unit (a)" in some cases. The repeating unit (a) includes "a phenolic hydroxyl group protected with a group that leaves by the action of an acid".

The resin (A) preferably has the repeating unit (a) having an acid-decomposable group.

The definition of the polar group is the same as that described in the section of the repeating unit (c) which will be described later, and examples of the polar group generated by decomposition of an acid-decomposable group include an alkaline soluble group, an amino group, and acidic group, and an alkaline soluble group is preferable.

The polar group is not particularly limited as long as it is a group which is solubilized in an organic developer, and preferred examples thereof include an alcoholic hydroxyl group, a phenolic hydroxyl group, a carboxylic acid group, a sulfonic acid group, a fluorinated alcohol group, a sulfonamido group, a sulfonylimido group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, more preferably a carboxylic acid group, a fluorinated alcohol group (preferably hexafluoroisopropanol), a phenolic hydroxyl group, an acid group such as a sulfonic acid group, and an alcoholic hydroxyl group.

Furthermore, the alcoholic hydroxyl group refers to a hydroxyl group bonded to a hydrocarbon group, which is other than a hydroxyl group (a phenolic hydroxyl group) directly bonded on an aromatic ring, and excludes an aliphatic alcohol (for example, a fluorinated alcohol group (a hexafluoroisopropanol group or the like)), of which the α-position is substituted with an electron withdrawing group such as a fluorine atom as a hydroxyl group. As the alcoholic hydroxyl group, a hydroxyl group having a pKa ranging from 12 to 20 is preferable.

A group that is preferable as the acid-decomposable group is a group in which a hydrogen atom is substituted with a group that leaves by an acid.

Examples of the group that leaves by an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formula, $R_{36}$ to $R_{39}$ each independently represent an alkyl group, a cycloalkyl group, an aryl group, a group obtained by combining an alkylene group and an aryl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, a group obtained by combining an alkylene group and an aryl group, or an alkenyl group.

The acid-decomposable group is preferably a cumyl ester group, an enol ester group, an acetal ester group, a tertiary alkyl ester group, or the like.

Examples of the repeating unit having a group that decomposes by the action of an acid to generate a polar group, which is included in the resin (A), include a repeating unit represented by the following General Formula (VI). Further, the following repeating unit is a repeating unit (a).

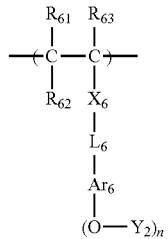
(VI)

In General Formula (VI), $R_{61}$, $R_{62}$, and $R_{63}$ each independently represent a hydrogen atom, an alkyl group, a cycloalkyl group, a halogen atom, a cyano group, or an alkoxycarbonyl group. Here, $R_{62}$ may be bonded to $Ar_6$ to form a ring, and $R_{62}$ in this case represents a single bond or an alkylene group.

$X_6$ represents a single bond, —COO—, or —CONR$_{64}$—. $R_{64}$ represents a hydrogen atom or an alkyl group.

$L_6$ represents a single bond or an alkylene group.

$Ar_6$ represents a (n+1)-valent aromatic ring group, and in the case of being bonded to $R_{62}$ to form a ring, represents a (n+2)-valent aromatic ring group.

In a case of n≥2, $Y_2$'s each independently represent a hydrogen atom or a group that leaves by the action of an acid. Here, at least one of $Y_2$'s represents a group that leaves by the action of an acid.

n represents an integer of 1 to 4.

General Formula (VI) will be described in more detail.

$R_{61}$ to $R_{63}$ in General Formula (VI) have the same definitions as $R_{51}$, $R_{52}$, and $R_{53}$ in General Formula (IVb) which will be described later, respectively, and the preferable ranges thereof are also the same.

In a case where $R_{62}$ represents an alkylene group, examples of the alkylene group include an alkylene group having 1 to 8 carbon atoms, such as a methylene group, an ethylene group, a propylene group, a butylene group, a hexylene group, and an octylene group, which may have a substituent.

Examples of the alkyl group of $R_{64}$ in —$CONR_{64}$— ($R_{64}$ represents a hydrogen atom or an alkyl group) represented by $X_6$ include the same ones as the alkyl groups represented by each of $R_{61}$ to $R_{63}$.

$X_6$ is preferably a single bond, —COO—, or —CONH—, and more preferably a single bond or —COO—.

Examples of the alkylene group in $L_6$ include an alkylene group having 1 to 8 carbon atoms, such as a methylene group, an ethylene group, a propylene group, a butylene group, a hexylene group, and an octylene group, which preferably may have a substituent. A ring formed by the bonding of $R_{62}$ and $L_6$ is particularly preferably a 5- or 6-membered ring.

$Ar_6$ represents a (n+1)-valent aromatic ring group. In a case where n is 1, the divalent aromatic ring group may have a substituent, and preferred examples thereof include an arylene group having 6 to 18 carbon atoms, such as a phenylene group, a tolylene group, and a naphthylene group, and a divalent aromatic ring group including a heterocycle, such as thiophene, furan, pyrrole, benzothiophene, benzofuran, benzopyrrole, triazine, imidazole, benzimidazole, triazole, thiadiazole, and thiazole.

Suitable specific examples of the (n+1)-valent aromatic ring group in a case where n is an integer of 2 or more include a group obtained by excluding arbitrary (n−1) hydrogen atoms from a specific example described above of the divalent aromatic ring group.

The (n+1)-valent aromatic ring group may further have a substituent.

Examples of the substituent which the alkyl group, the cycloalkyl group, the alkoxycarbonyl group, the alkylene group, or the (n+1)-valent aromatic ring group as described above can have are the same as the specific examples of the substituent which each of the groups represented by $R_{51}$ to $R_{53}$ in General Formula (V) which will be described later can have.

n is preferably 1 or 2, and more preferably 1.

n $Y_2$'s each independently represent a hydrogen atom or a group that leaves by the action of an acid. Here, at least one of n $Y_2$'s represents a group that leaves by the action of an acid.

Examples of $Y_2$ which is a group that leaves by the action of an acid include —$C(R_{36})(R_{37})(R_{38})$, —$C(=O)$—O—C$(R_{36})(R_{37})(R_{38})$, —$C(R_{01})(R_{02})(OR_{39})$, —$C(R_{01})(R_{02})$—C$(=O)$—O—C$(R_{36})(R_{37})(R_{38})$, and —$CH(R_{36})(Ar)$.

In the formulae, $R_{36}$ to $R_{39}$ each independently represent an alkyl group, a cycloalkyl group, an aryl group, a group formed by combining an alkylene group and an aryl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, a group formed by combining an alkylene group and an aryl group, or an alkenyl group.

Ar represents an aryl group.

The alkyl group of each of $R_{36}$ to $R_{39}$, $R_{01}$, and $R_{02}$ may be linear or branched, and is preferably an alkyl group having 1 to 8 carbon atoms, and examples thereof include a methyl group, an ethyl group, a propyl group, an n-butyl group, a sec-butyl group, a hexyl group, and an octyl group.

The cycloalkyl group of each of $R_{36}$ to $R_{39}$, $R_{01}$, and $R_{02}$ may be monocyclic or polycyclic. The monocyclic cycloalkyl group is preferably a cycloalkyl group having 3 to 10 carbon atoms, and examples thereof include a cyclopropyl group, a cyclobutyl group, a cyclopentyl group, a cyclohexyl group, and a cyclooctyl group. The polycyclic cycloalkyl group is preferably a cycloalkyl group having 6 to 20 carbon atoms, and examples thereof include an adamantyl group, a norbornyl group, an isobornyl group, a camphanyl group, a dicyclopentyl group, an α-pinene structure, a tricyclodecanyl group, a tetracyclododecyl group, and an androstanyl group. In addition, some of the carbon atoms in the cycloalkyl group may be substituted with heteroatoms such as an oxygen atom.

The aryl group of each of $R_{36}$ to $R_{39}$, $R_{01}$, $R_{02}$, and Ar is preferably an aryl group having 6 to 10 carbon atoms, and examples thereof include aryl groups such as a phenyl group, a naphthyl group, and an anthryl group, and divalent aromatic ring groups including a heterocycle, such as thiophene, furan, pyrrole, benzothiophene, benzofuran, benzopyrrole, triazine, imidazole, benzimidazole, triazole, thiadiazole, and thiazole.

A group formed by combining an alkylene group and an aryl group of each of $R_{36}$ to $R_{39}$, $R_{01}$, and $R_{02}$ is preferably an aralkyl group having 7 to 12 carbon atoms, and examples thereof include a benzyl group, a phenethyl group, and a naphthylmethyl group.

The alkenyl group of each of $R_{36}$ to $R_{39}$, $R_{01}$, and $R_{02}$ is preferably an alkenyl group having 2 to 8 carbon atoms, and examples thereof include a vinyl group, an allyl group, a butenyl group, and a cyclohexenyl group.

A ring formed by the mutual bonding of $R_{36}$ and $R_{37}$ may be monocyclic or polycyclic. The monocyclic ring preferably has a cycloalkyl structure having 3 to 10 carbon atoms, and examples thereof include a cyclopropane structure, a cyclobutane structure, a cyclopentane structure, a cyclohexane structure, a cycloheptane structure, and a cyclooctane structure. The polycyclic ring preferably has a cycloalkyl structure having 6 to 20 carbon atoms, and examples thereof include an adamantane structure, a norbornane structure, a dicyclopentane structure, a tricyclodecane structure, and a tetracyclododecane structure. In addition, some of the carbon atoms in the cycloalkyl structure may be substituted with heteroatoms such as an oxygen atom.

The respective groups as $R_{36}$ to $R_{39}$, $R_{01}$, $R_{02}$, and Ar may have a substituent, and examples of the substituent include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group, and the substituent preferably has 8 or less carbon atoms.

$Y_2$ which is a group that leaves by the action of an acid more preferably has the structure represented by the following General Formula (VI-A).

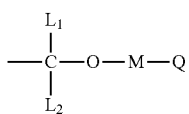
(VI-A)

Here, $L_1$ and $L_2$ each independently represent a hydrogen atom, an alkyl group, a cycloalkyl group, an aryl group, or a group formed by combining an alkylene group and an aryl group.

M represents a single bond or a divalent linking group.

Q represents an alkyl group, a cycloalkyl group which may include a heteroatom, an aryl group which may include a heteroatom, an amino group, an ammonium group, a mercapto group, a cyano group, or an aldehyde group.

At least two members out of Q, M, or $L_1$ may be bonded to each other to form a ring (preferably a 5- or 6-membered ring).

The alkyl group as each of $L_1$ and $L_2$ is, for example, an alkyl group having 1 to 8 carbon atoms, and specifically, preferred examples thereof include a methyl group, an ethyl group, a propyl group, an n-butyl group, a sec-butyl group, a hexyl group, and an octyl group.

The cycloalkyl group represented by each of $L_1$ and $L_2$ is, for example, a cycloalkyl group having 3 to 15 carbon atoms, and specifically, preferred examples thereof include a cyclopentyl group, a cyclohexyl group, a norbornyl group, and an adamantyl group.

The aryl group represented by each of $L_1$ and $L_2$ is, for example, an aryl group having 6 to 15 carbon atoms, and specifically, preferred examples thereof include a phenyl group, a tolyl group, a naphthyl group, and anthryl group.

A group formed by combining an alkylene group and an aryl group represented by each of $L_1$ and $L_2$ has, for example, 6 to 20 carbon atoms, and examples thereof include aralkyl groups such as a benzyl group and a phenethyl group.

Examples of the divalent linking group represented by M include alkylene groups (for example, a methylene group, an ethylene group, a propylene group, a butylene group, a hexylene group, and an octylene group), cycloalkylene groups (for example, a cyclopentylene group, a cyclohexylene group, and adamantylene group), alkenylene groups (for example, an ethylene group, a propenylene group, and a butenylene group), divalent aromatic ring groups (for example, a phenylene group, a tolylene group, and a naphthylene group), —S—, —O—, —CO—, —SO$_2$—, —N($R_0$)—, and divalent linking groups formed by combining a plurality of these. $R_0$ is a hydrogen atom or an alkyl group (which is, for example, an alkyl group having 1 to 8 carbon atoms, and specifically, a methyl group, an ethyl group, a propyl group, an n-butyl group, a sec-butyl group, a hexyl group, an octyl group, or the like).

The alkyl group as Q is the same as the alkyl group as each of $L_1$ and $L_2$ as described above.

In the cycloalkyl group as Q, which may include a heteroatom and the aryl group which may include a heteroatom, examples of the aliphatic hydrocarbon ring group which does not include a heteroatom and the aryl group which does not include a heteroatom include the cycloalkyl group and the aryl group represented by each of $L_1$ and $L_2$ as described above, and each of the cycloalkyl group and the aryl group preferably has 3 to 15 carbon atoms.

Examples the cycloalkyl group including a heteroatom and the aryl group including a heteroatom include a group having a heterocyclic structure such as thiirane, cyclothiolane, thiophene, furan, pyrrole, benzothiophene, benzofuran, benzopyrrole, triazine, imidazole, benzimidazole, triazole, thiadiazole, thiazole, or pyrrolidone, and the cycloalkyl group and the aryl group are not limited thereto as long as, in general, the groups have a structure (a ring formed by carbon and a heteroatom or a ring formed by heteroatoms) called a heterocycle.

As a ring formed by the mutual bonding of at least two members out of Q, M, or $L_1$, a case where at least two members out of Q, M, or $L_1$ are bonded to each other to form, for example, a propylene group or a butylene group, and a 5- or 6-membered ring containing an oxygen atom is formed is exemplified.

The respective groups represented by $L_1$, $L_2$, M, and Q in General Formula (VI-A) may have a substituent, and examples thereof include a substituent described as a substituent which each of $R_{36}$ to $R_{39}$, $R_{01}$, $R_{02}$, and Ar as described above may have, and the substituent preferably has 8 or less carbon atoms.

The group represented by -M-Q is preferably a group composed of 1 to 30 carbon atoms.

The repeating unit represented by General Formula (VI) is preferably a repeating unit represented by the following General Formula (3).

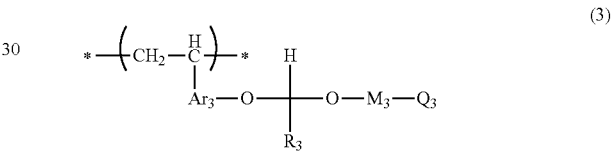
(3)

In General Formula (3), $Ar_3$ represents an aromatic ring group.

$R_3$ represents an alkyl group, a cycloalkyl group, an aryl group, an aralkyl group, an alkoxy group, an acyl group, or a heterocyclic group.

$M_3$ represents a single bond or a divalent linking group.

$Q_3$ represents an alkyl group, a cycloalkyl group, an aryl group, or a heterocyclic group.

At least two members out of $Q_3$, $M_3$, or $R_3$ may be bonded to each other to form a ring.

The aromatic ring group represented by $Ar_3$ is the same as $Ar_6$ in General Formula (VI) in a case where n in General Formula (VI) is 1, more preferably a phenylene group or a naphthylene group, and still more preferably a phenylene group.

$Ar_3$ may have a substituent, and examples of substituents which $Ar_3$ can have include the same substituents as substituents which $Ar_6$ in General Formula (VI) can have.

The alkyl group or the cycloalkyl group represented by $R_3$ has the same definition as the alkyl group or the cycloalkyl group represented by each of $R_{36}$ to $R_{39}$, $R_{01}$, and $R_{02}$ as described above.

The aryl group represented by $R_3$ described above has the same definition as the aryl group represented by each of $R_{36}$ to $R_{39}$, $R_{01}$, and $R_{02}$, and a preferred range thereof is also the same.

The aralkyl group represented by $R_3$ is preferably an aralkyl group having 7 to 12 carbon atoms, and examples thereof include a benzyl group, a phenethyl group, and a naphthylmethyl group.

The alkyl group moiety of the alkoxy group represented by $R_3$ is the same as alkyl group represented by each of $R_{36}$ to $R_{39}$, $R_{01}$, and $R_{02}$ as described above, and a preferred range thereof is also the same.

Examples of the acyl group represented by $R_3$ include an aliphatic acyl group having 1 to 10 carbon atoms, such as a formyl group, an acetyl group, a propionyl group, a butyryl group, an isobutyryl group, a valeryl group, a pivaloyl group, a benzoyl group, and a naphthoyl group, and the acyl group is preferably an acetyl group or a benzoyl group.

Examples of the heterocyclic group represented by $R_3$ include the cycloalkyl group including a heteroatom and the aryl group including a heteroatom, as described above, and the heterocyclic group is preferably a pyridine ring group or a pyran ring group.

$R_3$ is preferably a linear or branched alkyl group having 1 to 8 carbon atoms (specifically, a methyl group, an ethyl group, a propyl group, an i-propyl group, an n-butyl group, a sec-butyl group, a tert-butyl group, a neopentyl group, a hexyl group, a 2-ethylhexyl group, or an octyl group), a cycloalkyl group having 3 to 15 carbon atoms (specifically, a cyclopentyl group, a cyclohexyl group, a norbornyl group, or an adamantyl group), or a group having 2 or more carbon atoms. $R_3$ is more preferably an ethyl group, an i-propyl group, a sec-butyl group, a tert-butyl group, a neopentyl group, a cyclohexyl group, an adamantyl group, a cyclohexyl methyl group, or an adamantane methyl group, and still more preferably a tert-butyl group, a sec-butyl group, a neopentyl group, a cyclohexyl methyl group, or an adamantane methyl group.

The alkyl group, the cycloalkyl group, the aryl group, the aralkyl group, the alkoxy group, the acyl group, or the heterocyclic group as described above may further have a substituent, and examples of the substituent that the groups can have include those described as a substituent that each of $R_{36}$ to $R_{39}$, $R_{01}$, $R_{02}$, and Ar as described above may have.

The divalent linking group represented by $M_3$ as described above has the same definition as M in the structure represented by General Formula (VI-A), and a preferred range thereof is also the same. $M_3$ may have a substituent, and examples of the substituent which $M_3$ can have are the same as those which M in the group represented by General Formula (VI-A) as described above can have.

The alkyl group, the cycloalkyl group, and the aryl group represented by $Q_3$ have the same definitions as for Q in the structure represented by General Formula (VI-A), respectively, and preferred ranges thereof are also the same.

Examples of the heterocyclic group represented by $Q_3$ include a cycloalkyl group including a heteroatom and an aryl group including a heteroatom as Q in the structure represented by General Formula (VI-A).

$Q_3$ may have a substituent, and examples of the substituent which $Q_3$ can have include the same ones as the substituents which Q in the group represented by General Formula (VI-A) as described above can have.

A ring which is formed by the bonding of at least two members out of $Q_3$, $M_3$, or $R_3$ has the same definition as the ring which is formed by the mutual bonding of at least two members out of Q, M, or $L_1$ in General Formula (VI-A) as described above, and a preferred range thereof is also the same.

The resin (A) may have a repeating unit which is different from the repeating unit represented by General Formula (VI) as the repeating unit (a) including an acid-decomposable group that decomposes by the action of an acid. As such the repeating unit (a) including the acid-decomposable group, a repeating unit represented by the following General Formula (V) is preferable.

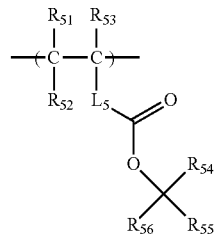

(V)

In General Formula (V), $R_{51}$, $R_{52}$, and $R_{53}$ each independently represent a hydrogen atom, an alkyl group, a cycloalkyl group, a halogen atom, a cyano group, or an alkoxycarbonyl group. $R_{52}$ may be bonded to $L_5$ to form a ring, and $R_{52}$ in this case represents an alkylene group.

$L_5$ represents a single bond or a divalent linking group, and in a case of forming a ring together with $R_{52}$, $L_5$ represents a trivalent linking group.

$R_{54}$ represents an alkyl group, and $R_{55}$ and $R_{56}$ each independently represent a hydrogen atom, an alkyl group, a cycloalkyl group, an aryl group, or an aralkyl group. $R_{55}$ and $R_{56}$ may be bonded to each other to form a ring. However, $R_{55}$ and $R_{56}$ are not a hydrogen atom at the same time in any case.

General Formula (V) will be described in more detail.

Preferred examples of the alkyl group of each of $R_{51}$ to $R_{53}$ in General Formula (V) include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, which may have a substituent, and an alkyl group having 8 or less carbon atoms is more preferable, and an alkyl group having 3 or less carbon atoms is particularly preferable.

The alkyl group included in the alkoxycarbonyl group is preferably the same one as the alkyl group in each of $R_{51}$ to $R_{53}$ as described above.

The cycloalkyl group may be monocyclic or polycyclic. Preferred examples include a monocyclic cycloalkyl group having 3 to 10 carbon atoms, such as a cyclopropyl group, a cyclopentyl group, or a cyclohexyl group, which may have a substituent.

Examples of the halogen atom include a fluorine atom, a chlorine atom, a bromine atom, and an iodine atom, with the fluorine atom being particularly preferable.

Preferred examples of the substituent in each of the groups include an alkyl group, a cycloalkyl group, an aryl group, an amino group, an amide group, a ureido group, a urethane group, a hydroxyl group, a carboxyl group, a halogen atom, an alkoxy group, a thioether group, an acyl group, an acyloxy group, an alkoxycarbonyl group, a cyano group, and nitro group, and the substituent preferably has 8 or less carbon atoms.

Furthermore, in a case where $R_{52}$ is an alkylene group and forms a ring together with $L_5$, preferred examples of the alkylene group include alkylene groups having 1 to 8 carbon atoms, such as a methylene group, an ethylene group, a propylene group, a butylene group, a hexylene group, and an octylene group. Alkylene groups having 1 to 4 carbon atoms are more preferable, and alkylene groups having 1 or 2 carbon atoms are particularly preferable. A ring formed by the bonding of $R_{52}$ and $L_5$ is particularly preferably a 5- or 6-membered ring.

As each of $R_{51}$ and $R_{53}$ in General Formula (V), a hydrogen atom, an alkyl group, or a halogen atom is more preferable, and a hydrogen atom, a methyl group, an ethyl group, a trifluoromethyl group (—$CF_3$), a hydroxymethyl group (—$CH_2$—OH), a chloromethyl group (—$CH_2$—Cl), or a fluorine atom (—F) is particularly preferable. As $R_{52}$, a hydrogen atom, an alkyl group, a halogen atom, or an alkylene group (which forms a ring together with $L_5$) is more preferable, and a hydrogen atom, a methyl group, an ethyl group, a trifluoromethyl group (—$CF_3$), a hydroxymethyl group (—$CH_2$—OH), a chloromethyl group (—$CH_2$—Cl), a fluorine atom (—F), a methylene group (which forms a ring together with $L_5$), or an ethylene group (which forms a ring together with $L_5$) is particularly preferable.

Examples of the divalent linking group represented by $L_5$ include an alkylene group, a divalent aromatic ring group, —COO-$L_{10}$-, —O-$L_{10}$-, and a group formed by combining two or more of these groups. Here, $L_{10}$ represents an alkylene group, a cycloalkylene group, a divalent aromatic ring group, or a group formed by combining an alkylene group and a divalent aromatic ring group.

$L_5$ is preferably a single bond, a group represented by —COO-$L_{10}$-, or a divalent aromatic ring group. $L_{10}$ is preferably an alkylene group having 1 to 5 carbon atoms, and more preferably a methylene or propylene group. As the divalent aromatic ring group, a 1,4-phenylene group, a 1,3-phenylene group, a 1,2-phenylene group, or a 1,4-naphthylene group is preferable, and a 1,4-phenylene group is more preferable.

In a case where $L_5$ is bonded to $R_{52}$ to form a ring, suitable examples of the trivalent linking group represented by $L_5$ include a group obtained by removing one arbitrary hydrogen atom from the specific example as described above of the divalent linking group represented by $L_5$.

The alkyl group of each of $R_{54}$ to $R_{56}$ is preferably an alkyl group having 1 to 20 carbon atoms, more preferably an alkyl group having 1 to 10 carbon atoms, and particularly preferably an alkyl group having 1 to 4 carbon atoms, such as a methyl group, an ethyl group, an n-propyl group, an isopropyl group, an n-butyl group, an isobutyl group, or a t-butyl group.

The cycloalkyl group represented by each of $R_{55}$ and $R_{56}$ is preferably a cycloalkyl group having 3 to 20 carbon atoms, may be a cycloalkyl group which is monocyclic, such as a cyclopentyl group and a cyclohexyl group, and may be a cycloalkyl group which is polycyclic, such as a norbornyl group, an adamantyl group, a tetratricyclodecanyl group, and a tetracyclodododecanyl group.

Moreover, a ring formed by the mutual bonding of $R_{55}$ and $R_{56}$ is preferably a ring having 3 to 20 carbon atoms, may be a monocyclic ring such as a cyclopentyl group and a cyclohexyl group, and may be a polycyclic ring such as a norbornyl group, an adamantyl group, a tetratricyclodecanyl group, and a tetracyclododecanyl group. In a case where $R_{55}$ and $R_{56}$ are bonded to each other to form a ring, $R_{54}$ is preferably an alkyl group having 1 to 3 carbon atoms, and a methyl group or an ethyl group is more preferable.

The aryl group represented by $R_{55}$ or $R_{56}$ preferably has 6 to 20 carbon atoms, and may be monocyclic or polycyclic, or may have a substituent. Examples thereof include a phenyl group, a 1-naphthyl group, a 2-naphthyl group, a 4-methylphenyl group, and a 4-methoxyphenyl group. In a case where any one of $R_{55}$ and $R_{56}$ is a hydrogen atom, the other is preferably an aryl group.

The aralkyl group represented by $R_{55}$ or $R_{56}$ may be monocyclic or polycyclic, or may have a substituent. The aralkyl group preferably has 7 to 21 carbon atoms, and examples thereof include a benzyl group and a 1-naphthylmethyl group.

Furthermore, the resin (A) may include a repeating unit represented by the following General Formula (BZ) as the repeating unit (a) having an acid-decomposable group.

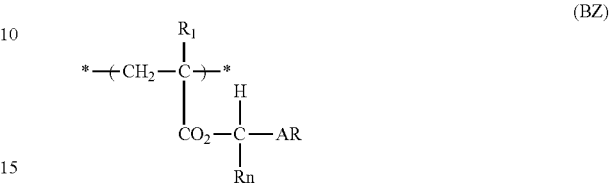

In General Formula (BZ), AR represents an aryl group. Rn represents an alkyl group, a cycloalkyl group, or an aryl group. Rn and AR may be bonded to each other to form a non-aromatic ring.

$R_1$ represents a hydrogen atom, an alkyl group, a cycloalkyl group, a halogen atom, a cyano group, or an alkyloxycarbonyl group.

With regard to the description (description of each group, specific examples of the repeating unit represented by General Formula (BZ), and the like) of the repeating unit represented by General Formula (BZ), reference can be made to the description of the repeating unit represented by General Formula (BZ) described in paragraphs [0101] to [0131] of JP2012-208447A, the contents of which are incorporated in the present specification.

The repeating unit having the acid-decomposable group may be used singly or in combination of two or more kinds thereof.

the content (in the case of containing plural kinds, the total content) of the repeating unit (a) having an acid-decomposable group in the resin (A) is preferably from 5% by mole to 80% by mole, more preferably from 5% by mole to 75% by mole, and still more preferably from 10% by mole to 65% by mole, with respect to all the repeating units in the resin (A).

The resin (A) may have a repeating unit having a polar group (c), in addition to the phenolic hydroxyl group.

The repeating unit (c) may be a repeating unit having a lactone structure or a sultone structure as a polar group.

As the repeating unit having a lactone structure, the repeating unit represented by the following General Formula (AII) is more preferable.

In General Formula (AII), $Rb_0$ represents a hydrogen atom, a halogen atom, or an alkyl group (preferably having 1 to 4 carbon atoms) which may have a substituent.

Preferred examples of the substituent which the alkyl group of $Rb_0$ can have include a hydroxyl group and a halogen atom. Examples of the halogen atom of $Rb_0$ include a fluorine atom, a chlorine atom, a bromine atom, and an iodine atom. $Rb_0$ is preferably a hydrogen atom, a methyl group, a hydroxymethyl group, or a trifluoromethyl group, and particularly preferably a hydrogen atom or a methyl group.

Ab represents a single bond, an alkylene group, a divalent linking group having a monocyclic or polycyclic cycloalkyl structure, an ether bond, an ester bond, a carbonyl group, or a divalent linking group obtained by combining these. Ab is preferably a single bond or a divalent linking group represented by -$Ab_1$-$CO_2$—.

$Ab_1$ is a linear or branched alkylene group or a monocyclic or polycyclic cycloalkylene group, and preferably a methylene group, an ethylene group, a cyclohexylene group, an adamantylene group, or a norbornylene group.

V represents a group having a lactone structure.

As the group having a lactone structure, any group can be used as long as the group has a lactone structure, but the group preferably has a 5- to 7-membered ring lactone structure. It is preferable that another ring structure is condensed with the 5- to 7-membered lactone structure while forming a bicyclo structure or a spiro structure. The group more preferably has a repeating unit having a lactone structure represented by any one of the following General Formulae (LC1-1) to (LC1-17). In addition, the lactone structure may be directly bonded to the main structure. A preferred structure is (LC1-1), (LC1-4), (LC1-5), (LC1-6), (LC1-8), (LC1-13), or (LC1-14).

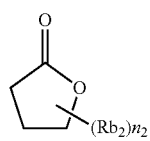
LC1-1

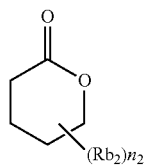
LC1-2

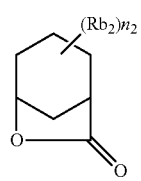
LC1-3

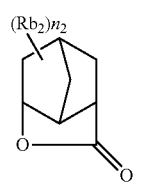
LC1-4

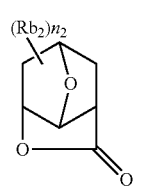
LC1-5

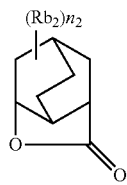
LC1-6

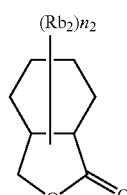
LC1-7

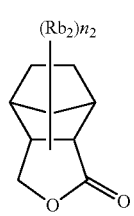
LC1-8

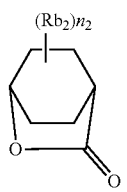
LC1-9

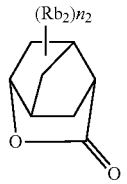
LC1-10

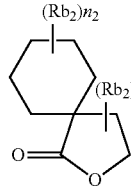
LC1-11

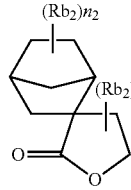
LC1-12

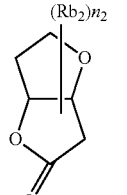
LC1-13

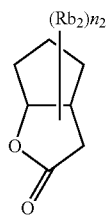
LC1-14

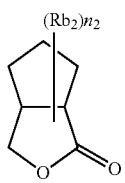
LC1-15

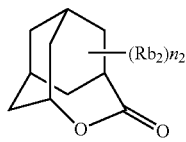
LC1-16

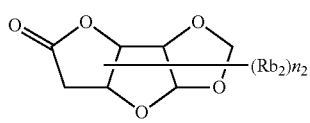
LC1-17

The lactone structure moiety may or may not have a substituent (Rb$_2$). Preferred examples of the substituent (Rb$_2$) include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, and an acid-decomposable group. The substituent (Rb$_2$) is more preferably an alkyl group having 1 to 4 carbon atoms, a cyano group, or an acid-decomposable group. n$_2$ represents an integer of 0 to 4. When n$_2$ is 2 or more, the substituents (Rb$_2$) which are present in plural numbers be the same as or different from each other, and the substituents (Rb$_2$) which are present in plural numbers be bonded to each other to form a ring.

The repeating unit having a lactone structure typically has optical isomers, and any optical isomer may be used. In addition, one kind of optical isomer may be used singly, or plural kinds of optical isomers may be used in combination. In a case where one kind of optical isomer is mainly used, the optical purity (ee) is preferably 90% or more, and more preferably 95% or more.

The resin (A) may contain or may not contain a repeating unit having a lactone structure, and in a case where the resin (A) contains the repeating unit having a lactone structure, the content of the repeating unit in the resin (A) is preferably in a range of 1% to 70% by mole, more preferably in a range of 3% to 65% by mole, and still more preferably in a range of 5% to 60% by mole, with respect to all the repeating units.

Specific examples of the repeating unit having a lactone structure in the resin (A) are shown below, but the present invention is not limited thereto. In the formulae, Rx represents H, CH$_3$, CH$_2$OH, or CF$_3$.

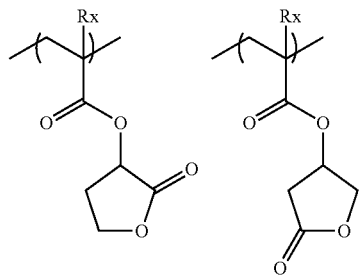

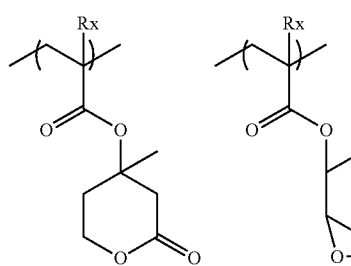

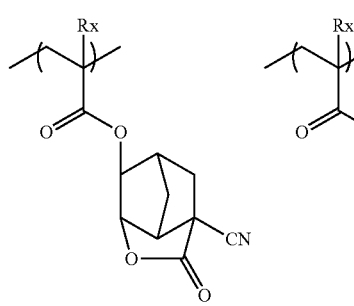

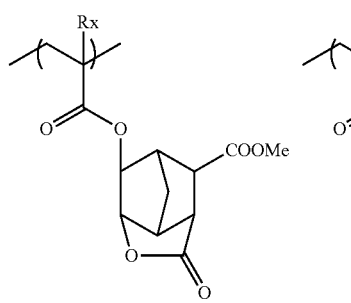

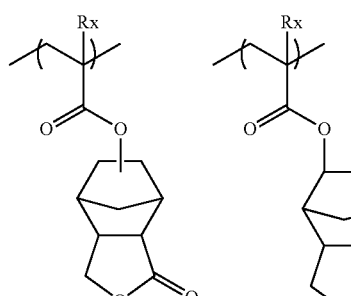

-continued

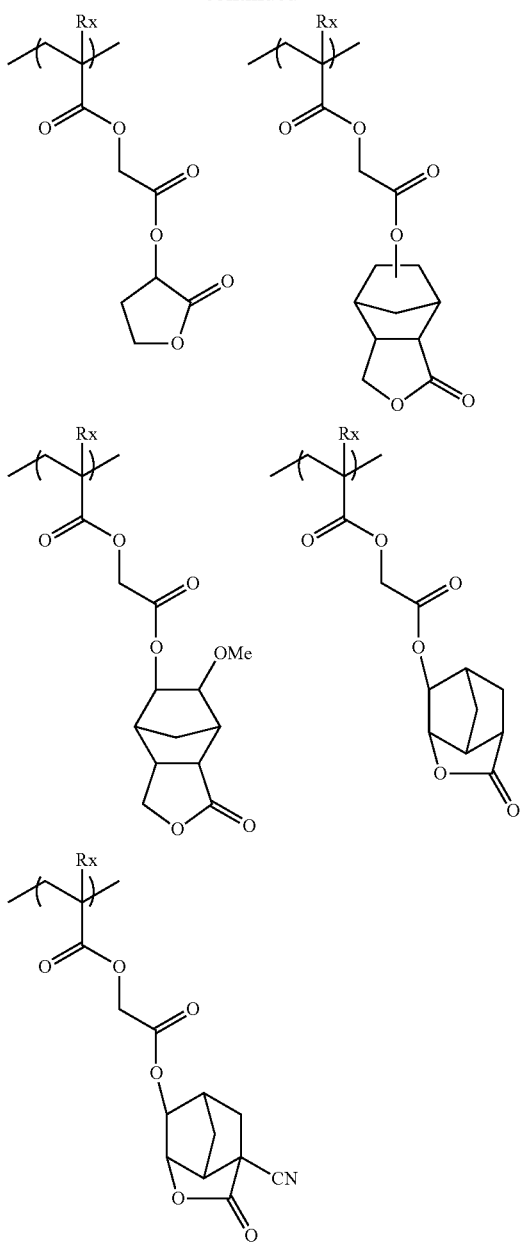

Moreover, as a sultone structure which the resin (A) may have, the following General Formula (SL-1) or (SL-2) is preferable. $Rb_2$ and $n_2$ in the formulae have the same definitions as those in General Formulae (LC1-1) to (LC1-17), respectively.

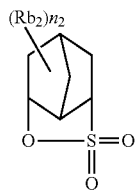

SL1-1

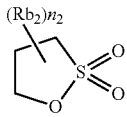

SL1-2

As the repeating unit including a sultone structure which the resin (A) may have, a repeating unit formed by substituting the lactone structure in the repeating unit having an lactone structure as described above with a sultone structure is preferable.

Moreover, it is also one of particularly preferable embodiments that a polar group which the repeating unit (c) can have is an acidic group. Preferred examples of the acidic group include a carboxylic acid group, a sulfonic acid group, a fluorinated alcohol group (for example, a hexafluoroisopropanol group), a sulfonamide group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group. Among these, the repeating unit (c) is more preferably a repeating unit having a carboxyl group. Examples of the repeating unit having an acidic group include a repeating unit of which an acidic group is directly bonded to the main chain of a resin as a repeating unit by acrylic acid or methacrylic acid and a repeating unit of which an acidic group is bonded to the main chain of a resin through a linking group, and further, introduction of an acidic group into a terminal of a polymer chain using a polymerization initiator or a chain transfer agent having an acidic group at the time of polymerization is preferable. A repeating unit by acrylic acid or methacrylic acid is particularly preferable.

The acidic group which the repeating unit (c) can have may or may not include an aromatic ring, but in a case where the acidic group has an aromatic ring, the acidic group is preferably selected from acidic groups other than a phenolic hydroxyl group. In a case where the resin (A) contains a repeating unit having an acidic group, the content of the repeating unit having an acidic group in the resin (A) is usually 1% by mole or more.

Specific examples of the repeating unit having an acidic group are shown below, but the present invention is not limited thereto.

In the specific examples, Rx represents H, $CH_3$, $CH_2OH$, or $CF_3$.

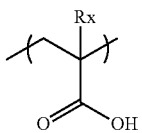 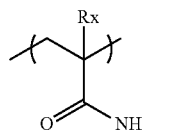

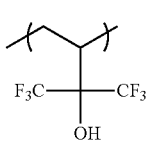 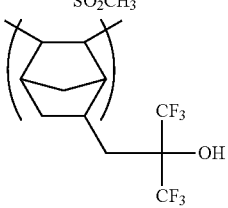

-continued

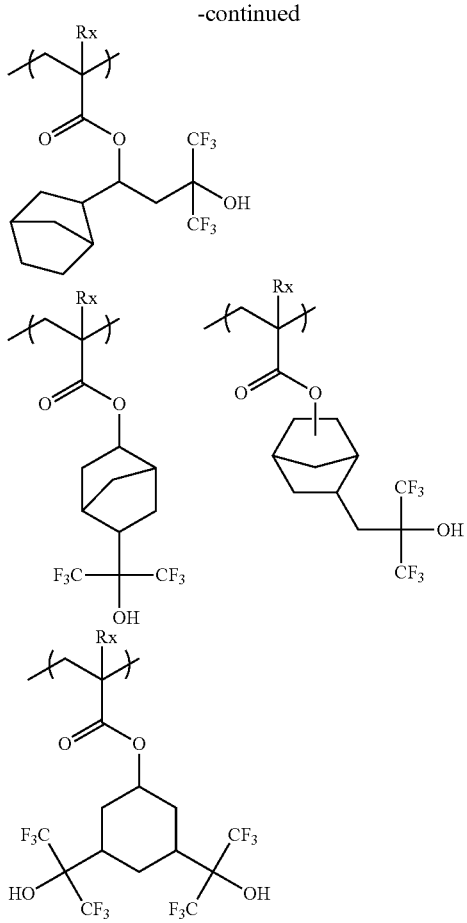

(d) Repeating Unit Having Plurality of Aromatic Rings

The resin (A) may have a repeating unit (d) having a plurality of aromatic ring.

Examples of such the repeating unit having aromatic rings include repeating units derived from a monomer such as styrene, p-hydroxystyrene, phenyl acrylate, and phenyl methacrylate, and among these, the resin (A) preferably further has the repeating unit (d) having a plurality of aromatic rings represented by the following General Formula (c1).

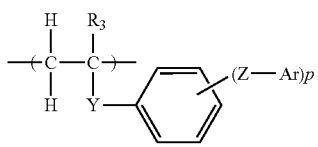

(c1)

In General Formula (c1), $R_3$ represents a hydrogen atom, an alkyl group, a halogen atom, a cyano group, or a nitro group, Y represents a single bond or a divalent linking group, Z represents a single bond or a divalent linking group, Ar represents an aromatic ring group, and p represents an integer of 1 or more.

The alkyl group as $R_3$ may be linear or branched. Examples thereof include a methyl group, an ethyl group, an n-propyl group, an i-propyl group, an n-butyl group, a sec-butyl group, a t-butyl group, an n-pentyl group, an n-hexyl group, an n-heptyl group, an n-octyl group, an n-nonyl group, an n-decanyl group, and an i-butyl group, and the alkyl group may have a substituent. Preferred examples of the substituent include an alkoxy group, a hydroxyl group, a halogen atom, and a nitro group. Among these, as the alkyl group having a substituent, a $CF_3$ group, an alkyloxycarbonyl methyl group, an alkylcarbonyloxy methyl group, a hydroxymethyl group, an alkoxymethyl group, or the like is preferable.

Examples of the halogen atom as $R_3$ include a fluorine atom, a chlorine atom, a bromine atom, and an iodine atom, with the fluorine atom being particularly preferable.

Y represents a single bond or a divalent linking group, and examples of the divalent linking group include an ether group (oxygen atom), a thioether group (sulfur atom), an alkylene group, an arylene group, a carbonyl group, a sulfide group, a sulfone group, —COO—, —CONH—, —$SO_2$NH—, —$CF_2$—, —$CF_2CF_2$—, —$OCF_2$O—, —$CF_2OCF_2$—, —SS—, —$CH_2SO_2CH_2$—, —$CH_2COCH_2$—, —$COCF_2$CO—, —COCO—, —OCOO—, —$OSO_2$O—, an amino group (nitrogen atom), an acyl group, an alkylsulfonyl group, —CH=CH—, —C≡C—, an aminocarbonylamino group, an aminosulfonylamino group, and a group obtained by combining these. Y preferably has 15 or less carbon atoms, and more preferably has 10 or less carbon atoms.

Y is preferably a single bond, a —COO— group, a —COS— group, or a —CONH— group, more preferably a —COO— group or a —CONH— group, and particularly preferably a —COO— group.

Z represents a single bond or a divalent linking group, and examples of the divalent linking group include an ether group (oxygen atom), a thioether group (sulfur atom), an alkylene group, an arylene group, a carbonyl group, a sulfide group, a sulfone group, —COO—, —CONH—, —$SO_2$NH—, an amino group (nitrogen atom), an acyl group, an alkylsulfonyl group, —CH=CH—, an aminocarbonylamino group, an aminosulfonylamino group, or a group obtained by combining these.

Z is preferably a single bond, an ether group, a carbonyl group, or a —COO—, more preferably a single bond or an ether group, and particularly preferably a single bond.

Ar represents an aromatic ring group, and specific examples thereof include a phenyl group, a naphthyl group, an anthracenyl group, a phenanthrenyl group, a quinolinyl group, a furanyl group, a thiophenyl group, a fluorenyl-9-on-yl group, an anthraquinonyl group, a phenanthraquinonyl group, and a pyrrole group, and a phenyl group is preferable. The aromatic ring group may further have a substituent, and preferable examples of the substituent include an alkyl group, an alkoxy group, a hydroxyl group, a halogen atom, a nitro group, an acyl group, an acyloxy group, an acylamino group, a sulfonylamino group, an aryl group such as a phenyl group, an aryloxy group, an arylcarbonyl group, and a heterocyclic residue. Among these, a phenyl group is preferable from the viewpoint of suppressing deterioration of exposure latitude or a pattern shape due to out band light.

p is an integer of 1 or more, and is preferably an integer of 1 to 3.

The repeating unit (d) is more preferably a repeating unit represented by the following Formula (c2).

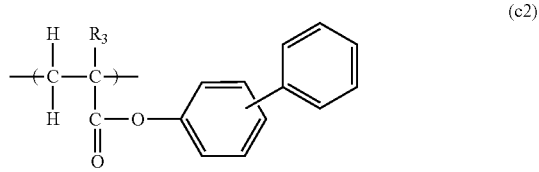

(c2)

In General Formula (c2), $R_3$ represents a hydrogen atom or an alkyl group. Preferable alkyl group as $R_3$ is the same as the alkyl group as $R_3$ in General Formula (c1).

Here, regarding extreme ultraviolet rays (EUV light) exposure, leakage light (out of band light) generated in a region of ultraviolet rays having a wavelength of 100 nm to 400 nm deteriorates the surface roughness, and as a result, the resolution or LWR performance tends to be reduced due to a bridge between patterns or disconnection of a pattern.

However, the aromatic ring in the repeating unit (d) functions as an internal filter capable of absorbing the out of band light. Accordingly, the resin (A) preferably contains the repeating unit (d) from the viewpoint of high resolution and low LWR.

The repeating unit (d) preferably does not have a phenolic hydroxyl group (hydroxyl group directly bonded to an aromatic ring) from the viewpoint of obtaining high resolution.

The resin (A) may contain or may not contain the repeating unit (d), and in a case where the resin (A) contains the repeating unit (d), the content of the repeating unit (d) is preferably within a range of 1% to 30% by mole, more preferably within a range of 1% to 20% by mole, and still more preferably within a range of 1% to 15% by mole, with respect to all the repeating units in the resin (A). The repeating unit (d) included in the resin (A) may be included in combination of two or more types thereof.

The resin (A) in the present invention may suitably have a repeating unit other than the repeating units (a), (c), and (d).

In the resin (A), the content molar ratio of respective repeating structural units is suitably set to adjust the dry etching resistance or the standard developer suitability of a resist, adhesiveness to a substrate, a resist profile, and resolving power, and heat resistance, sensitivity, and the like which are properties generally required for a resist.

The form of the resin (A) may be any form of a random form, a block form, a comb form, and a star form.

The resin (A) can be synthesized by, for example, polymerizing an unsaturated monomer corresponding to each structure through radical polymerization, cationic polymerization, or anionic polymerization. In addition, by carrying out a polymer reaction after polymerization is carried out using an unsaturated monomer corresponding to a precursor of each structure, a target resin can also be obtained.

Examples of a general synthetic method include a collective polymerization method of carrying out polymerization by dissolving an unsaturated monomer and a polymerization initiator in a solvent and heating the resultant product and a dropwise addition polymerization method of adding a solution containing an unsaturated monomer and an polymerization initiator dropwise to a heated solvent over a period of 1 to 10 hours, and the dropwise addition polymerization method is preferable.

Examples of the solvent used in the polymerization include solvents which can be used in preparing an active-light-sensitive or radiation-sensitive resin composition which will be described later, and it is more preferable that the polymerization is carried out using the same solvent as the solvent (D) used in the composition of the present invention. Thus, generation of particles during storage can be suppressed.

The polymerization reaction is preferably carried out in an inert gas atmosphere such as nitrogen and argon. The polymerization is initiated using a commercially available radical initiator as a polymerization initiator (an azo-based initiator, a peroxide, or the like). As the radical initiator, an azo-based initiator is preferable, and an azo-based initiator having an ester group, a cyano group, or a carboxyl group is preferable. Preferred examples of the initiator include azobisisobutyronitrile, azobisdimethylvaleronitrile, and dimethyl 2,2'-azobis(2-methylpropionate). If necessary, polymerization may be carried out in the presence of a chain transfer agent (for example, alkyl mercaptan).

The concentration of the reaction is usually 5% to 70% by mass, and preferably 10% to 50% by mass. The reaction temperature is typically 10° C. to 150° C., preferably 30° C. to 120° C., and more preferably 40 to 100° C.

The reaction time is usually 1 to 48 hours, preferably 1 to 24 hours, and more preferably 1 to 12 hours.

After completion of the reaction, cooling to room temperature and purification are carried out. A usual method such as a liquid-liquid extraction method in which a residual monomer or an oligomer component is removed by washing with water or combining suitable solvents, a purification method in a solution state such as ultrafiltration which extracts and removes only substances having a specific molecular weight or less, a reprecipitation method in which a residual monomer or the like is removed by adding a resin solution dropwise to a poor solvent to coagulate the resin in the poor solvent, or a purification method in a solid state in which filtered resin slurry is washed with a poor solvent can be applied to the purification. For example, by bringing into contact with a solvent (a poor solvent), which does poorly dissolve or does not dissolve the resin, corresponding to 10 times or less the volume amount of the reaction solution, or preferably 10 to 5 times the volume amount of the reaction solution, the resin is solidified and precipitated.

The solvent (a precipitation or reprecipitation solvent) used in a precipitation or reprecipitation operation from the polymer solution may be a poor solvent for the polymer, and depending on the type of the polymer, the solvent can be appropriately selected from a hydrocarbon, a halogenated hydrocarbon, a nitro compound, ether, ketone, ester, carbonate, alcohol, carboxylic acid, water, and a mixed solvent including these solvents and used. Among these, as a precipitation or reprecipitation solvent, a solvent including at least alcohol (in particular, methanol) or water is preferable.

The amount of the precipitation or reprecipitation solvent to be used can be appropriately selected in consideration of efficiency, a yield, or the like, but is generally 100 to 10,000 parts by mass, preferably 200 to 2,000 parts by mass, and more preferably 300 to 1,000 parts by mass, with respect to 100 parts by mass of the polymer solution.

The temperature at a time of precipitation or reprecipitation can be appropriately selected in consideration of efficiency or operability, but is usually approximately 0° C. to 50° C., and preferably around room temperature (for example, approximately 20° C. to 35° C.). Precipitation or reprecipitation operation can be carried out by a known method such as a batch type method and a continuous type method, using a generally used mixing vessel such as a stirring vessel.

The precipitated or reprecipitated polymer is usually subjected to solid-liquid separation generally used, such as filtration and centrifugation, dried, and then provided for use. The filtration is preferably carried out under pressure using a solvent-resistant filter medium. The drying is carried out at a temperature of approximately 30° C. to 100° C. at normal pressure or under reduced pressure (preferably, under reduced pressure), and preferably at a temperature of approximately 30° C. to 50° C.

Moreover, once the resin is precipitated and separated, and then it may be again dissolved in a solvent to be brought into contact with a solvent which does poorly dissolve or does not dissolve the resin. That is, a method which includes a step of precipitating a resin by bringing into contact with a poorly soluble or insoluble solvent which does not dissolve the polymer after the radical polymerization reaction ends (step a), a step of separating the resin from the solution (step b), a step of preparing a resin solution A by dissolving the resin in a solvent (step c), thereafter, by bringing the resin solution A into contact with a solvent in which the resin is poorly soluble or insoluble, corresponding to 10 times or less the volume amount (preferably 5 times or less the volume amount) of the resin solution A, the resin solid is precipitated (step d), and a step of separating the precipitated resin (step e) may be carried out.

It is preferable that the polymerization reaction is carried out in an inert gas atmosphere such as nitrogen and argon. As the polymerization initiator, commercially available radical initiators (an azo-based initiator, a peroxide, or the like) are used to initiate the polymerization. As the radical initiator, an azo-based initiator is preferable, and the azo-based initiator having an ester group, a cyano group, or a carboxyl group is preferable. Preferable initiators include azobisisobutyronitrile, azobisdimethylvaleronitrile, dimethyl 2,2'-azobis(2-methyl propionate), or the like. The initiator is added or added in portionwise, depending on the purposes, and after completion of the reaction, the reaction mixture is poured into a solvent, and then a desired polymer is recovered by a method such as powder or solid recovery. The concentration of the reaction is 5% to 50% by mass, and preferably 10% to 30% by mass. The reaction temperature is normally 10° C. to 150° C., preferably 30° C. to 120° C., and more preferably 60 to 100° C.

The molecular weight of the resin (A) according to the present invention is not particularly limited, but the weight-average molecular weight is preferably in a range of 1,000 to 100,000, more preferably in a range of 1,500 to 60,000, and particularly preferably in a range of 2,000 to 30,000. When the weight-average molecular weight is in a range of 1,000 to 100,000, degradation of heat resistance or dry etching resistance can be prevented, and degradation of developability or degradation of film formability due to increase in viscosity can be prevented. Here, the weight-average molecular weight of the resin represent a molecular weight in terms of polystyrene, as measured by means of GPC (carrier: THF or N-methyl-2-pyrrolidone (NMP)).

Moreover, the dispersity (Mw/Mn) is preferably 1.00 to 5.00, more preferably 1.00 to 3.50, and still more preferably 1.00 to 2.50. As the molecular weight distribution is lower, the resolution and the resist shape become better, and the side wall of the resist pattern becomes smoother, and thus, the roughness becomes excellent.

The resin (A) can be used singly or in combination of two or more kinds thereof. The content of the resin (A) is preferably 20% to 99% by mass, more preferably 30% to 99% by mass, and still more preferably 40% to 99% by mass, with respect to the total solid content in the active-light-sensitive or radiation-sensitive resin composition.

[(B) Compound that Generates Acid by Active Light or Radiation]

The composition in the present invention contains a (B) compound that generates an acid by active light or radiation (hereinafter referred to as an "acid generator" or an "acid generator (B)").

The acid generator may have a form of a low molecular compound or may have a form in which the acid generator is incorporated into a part of a polymer. In addition, the form of a low molecular compound and the form in which the acid generator is incorporated into a part of a polymer may be used in combination.

In a case where the acid generator has a form of a low molecular compound, the molecular weight thereof is preferably 3,000 or less, more preferably 2,000 or less, and still more preferably 1,000 or less.

In a case where the acid generator has a form in which the acid generator is incorporated into a part of a polymer, the acid generator may be incorporated into a part of the resin (A), or may be incorporated into a resin different from the resin (A).

In the present invention, the acid generator is preferably a form of the low molecular compound.

The acid generator (B) is not particularly limited as long as it is a known acid generator, but the acid generator is preferably a compound which generates an organic acid, for example, at least any one of sulfonic acid, bis(alkylsulfonyl) imide, or tris(alkylsulfonyl)methide upon irradiation with active light or radiation, and preferably an electron beam or extreme ultraviolet rays.

More preferably, compounds represented by the following General Formula (ZI), (ZII), and (ZIII) can be exemplified.

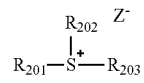

(ZI)

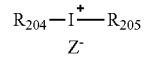

(ZII)

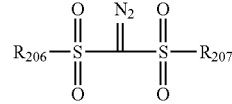

(ZIII)

In General Formula (ZI), $R_{201}$, $R_{202}$, and $R_{203}$ each independently represent an organic group.

The number of carbon atoms of the organic group as $R_{201}$, $R_{202}$, and $R_{203}$ is generally 1 to 30, and preferably 1 to 20.

Furthermore, two members out of $R_{201}$ to $R_{203}$ may be bonded to each other to form a ring structure, and the ring may contain an oxygen atom, a sulfur atom, an ester bond, an amide bond, or a carbonyl group. Examples of the group formed by the mutual bonding of two members out of $R_{201}$ to $R_{203}$ include an alkylene group (for example, a butylene group and a pentylene group).

$Z^-$ refers to a non-nucleophilic anion (an anion having an extremely low ability of causing a nucleophilic reaction).

Examples of the non-nucleophilic anion include a sulfonate anion (an aliphatic sulfonate anion, an aromatic sulfonate anion, and a camphorsulfonate anion), a carboxylate anion (an aliphatic carboxylic anion, an aromatic carboxylate anion, and an aralkylcarboxylate anion), a sulfonylimide anion, a bis(alkylsulfonyl)imide anion, and a tris(alkylsulfonyl)methide anion.

The aliphatic site in the aliphatic sulfonate anion and the aliphatic carboxylate anion may be an alkyl group, or a cycloalkyl group, and preferred examples thereof include a linear or branched alkyl group having 1 to 30 carbon atoms or a cycloalkyl group having 3 to 30 carbon atoms.

Preferred examples of the aromatic group in the aromatic sulfonate anion and the aromatic carboxylate anion include an aryl group having 6 to 14 carbon atoms, such as a phenyl group, a tolyl group, and a naphthyl group.

The alkyl group, the cycloalkyl group, and the aryl group as mentioned above may have a substituent. Specific examples of the substituent include a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 1 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), and a cycloalkylalkyloxyalkyloxy group (preferably having 8 to 20 carbon atoms). The aryl group or ring structure which each of the groups has may further have an alkyl group (preferably having 1 to 15 carbon atoms) as a substituent.

The aralkyl group in the aralkylcarboxylate anion is preferably an aralkyl group having 7 to 12 carbon atoms, and examples thereof include a benzyl group, a phenethyl group, a naphthylmethyl group, a naphthylethyl group and a naphthylbutyl group.

Examples of the sulfonylimide anion include a saccharin anion.

The alkyl group in the bis(alkylsulfonyl)imide anion and tris(alkylsulfonyl)methide anion is preferably an alkyl group having 1 to 5 carbon atoms. Examples of the substituent of the alkyl group include a halogen atom, a halogen atom-substituted alkyl group, an alkoxy group, an alkylthio group, an alkyloxysulfonyl group, an aryloxysulfonyl group, and a cycloalkylaryloxysulfonyl group, with the fluorine atom and the fluorine atom-substituted alkyl group being preferred.

Furthermore, the alkyl groups in the bis(alkylsulfonyl)imide anion may be bonded to each other to form a ring structure, whereby the acid strength increases.

Other examples of non-nucleophilic anion include fluorinated phosphorus (for example, $PF_6^-$), fluorinated boron (for example, $BF_4^-$), and fluorinated antimony (for example, $SbF_6^-$).

The non-nucleophilic anion is preferably an aliphatic sulfonate anion substituted with a fluorine atom at least at the α-position of sulfonic acid, an aromatic sulfonate anion substituted with a fluorine atom or a group having a fluorine atom, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoroaliphatic sulfonate anion (still more preferably having 4 to 8 carbon atoms) or a benzenesulfonate anion having a fluorine atom, and even still more preferably a nonafluorobutanesulfonate anion, a perfluorooctanesulfonate anion, a pentafluorobenzenesulfonate anion, or a 3,5-bis(trifluoromethyl)benzenesulfonate anion.

From the viewpoint of the acid strength, the pKa of the generated acid is preferably −1 or less in order to improve the sensitivity.

Moreover, preferred embodiments of the non-nucleophilic anion also include an anion represented by the following General Formula (AN1).

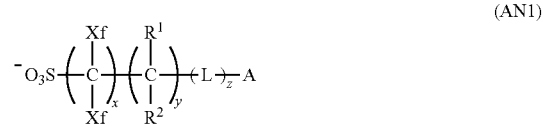

(AN1)

In the formula, Xf's each independently represent a fluorine atom or an alkyl group substituted with at least one fluorine atom.

$R^1$ and $R^2$ each independently represent a hydrogen atom, a fluorine atom, or an alkyl group, and in a case where a plurality of $R^1$'s or $R^2$'s are present, they may be the same as or different from each other.

L represents a divalent linking group, and in a case where a plurality of L's are present, they may be the same as or different from each other.

A represents a cyclic organic group.

x represents an integer of 1 to 20, y represents an integer of 0 to 10, and z represents an integer of 0 to 10.

General Formula (AN1) will be described in more detail.

The alkyl group in the alkyl group substituted with a fluorine atom of Xf preferably has 1 to 10 carbon atoms, and more preferably 1 to 4 carbon atoms. In addition, the alkyl group substituted with a fluorine atom of Xf is preferably a perfluoroalkyl group.

Xf is preferably a fluorine atom or a perfluoroalkyl group having 1 to 4 carbon atoms. Specific examples of Xf include a fluorine atom, $CF_3$, $C_2F_5$, $C_3F_7$, $C_4F_9$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, a fluorine atom or $CF_3$ is preferable. In particular, both of Xf's are preferably fluorine atoms.

The alkyl group of $R^1$ or $R^2$ may have a substituent (preferably a fluorine atom), and the alkyl group is preferably an alkyl group having 1 to 4 carbon atoms, and more preferably a perfluoroalkyl group having 1 to 4 carbon atoms. Specific examples of the alkyl group having a substituent of $R^1$ or $R^2$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, and $CH_2CH_2C_4F_9$, and among these, $CF_3$ is preferable.

Each of $R^1$ and $R^2$ is preferably a fluorine atom or $CF_3$.

x is preferably 1 to 10, and more preferably 1 to 5.

y is preferably 0 to 4, and more preferably 0.

z is preferably 0 to 5, and more preferably 0 to 3.

The divalent linking group of L is not particularly limited, and examples thereof include —COO—, —OCO—, —CO—, —O—, —S—, —SO—, —SO$_2$—, an alkylene group, a cycloalkylene group, an alkenylene group, and a linking group obtained by connecting a plurality of these, and a linking group having 12 or less total carbon atoms is preferable. Among these, —COO—, —OCO—, —CO—, or —O— is preferable, and —COO— or —OCO— is more preferable.

The cyclic organic group of A is not particularly limited as long as it has a ring structure, and examples thereof include an alicyclic group, an aryl group, and a heterocyclic group (including not only a heterocyclic group having aromaticity but also a heterocyclic group without aromaticity).

The alicyclic group may be monocyclic or polycyclic, and as the alicyclic group, a monocyclic cycloalkyl group such as a cyclopentyl group, a cyclohexyl group, or a cyclooctyl group, or polycyclic cycloalkyl groups such as a norbornyl group, a tricyclodecanyl group, a tetracyclodecanyl group, a tetracyclododecanyl group, or an adamantyl group is preferable. Among these, an alicyclic group with a bulky structure having 7 or more carbon atoms such as a norbornyl group, a tricyclodecanyl group, a tetracyclodecanyl group, a tetracyclododecanyl group, or an adamantyl group is preferable from the viewpoint of being capable of suppressing in-film diffusibility in a heating step after exposure and MEEF improvement.

Examples of the aryl group include a benzene ring, a naphthalene ring, a phenanthrene ring, and an anthracene ring.

Examples of the heterocyclic group include groups derived from a furan ring, a thiophene ring, a benzofuran ring, a benzothiophene ring, a dibenzofuran ring, a dibenzothiophene ring, and a pyridine ring. Among these, a group derived from a furan ring, a thiophene ring, or a pyridine ring is preferable.

In addition, examples of the cyclic organic group also include a lactone structure, and specific examples thereof include the lactone structures represented by General Formulae (LC1-1) to (LC1-17), which the resin (A) as described above may have.

The cyclic organic group may has a substituent, and Examples of the cyclic organic group may have a substituent, and examples of the substituent include an alkyl group (which may be linear, branched, or cyclic, and preferably has 1 to 12 carbon atoms), a cycloalkyl group (which may be a monocycle, a polycycle, or a spiro ring, and preferably has 3 to 20 carbon atoms), an aryl group (which preferably has 6 to 14 carbon atoms), a hydroxyl group, an alkoxy group, an ester group, an amide group, a urethane group, a ureido group, a thioether group, a sulfonamide group, and a sulfonic acid ester group. Moreover, the carbon (carbon which contributes to formation of a ring) constituting the cyclic organic group may be a carbonyl carbon.

Examples of the organic group of each of $R_{201}$, $R_{202}$, and $R_{203}$ include an aryl group, an alkyl group, and a cycloalkyl group.

It is preferable that at least one of $R_{201}$, $R_{202}$, or $R_{203}$ is an aryl group, and it is more preferable that all of three are aryl groups. Examples of the aryl group include heteroaryl groups such as an indole residue and a pyrrole residue, in addition to a phenyl group and a naphthyl group. Preferable examples of the alkyl group or the cycloalkyl group represented by each of $R_{201}$ to $R_{203}$ can include a linear or branched alkyl group having 1 to 10 carbon atoms and a cycloalkyl group having 3 to 10 carbon atoms. More preferable examples of the alkyl group can include a methyl group, an ethyl group, an n-propyl group, an i-propyl group, and an n-butyl group. More preferable examples of the cycloalkyl group can include a cyclopropyl group, a cyclobutyl group, a cyclopentyl group, a cyclohexyl group, and a cycloheptyl group. These groups may further contain a substituent. Examples of the substituent include a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), and an alkoxycarbonyloxy group (preferably having 2 to 7 carbon atoms), but are not limited thereto.

In addition, in a case where two members out of $R_{201}$ to $R_{203}$ are bonded to each other to form a ring structure, the structure represented by the following General Formula (A1) is preferable.

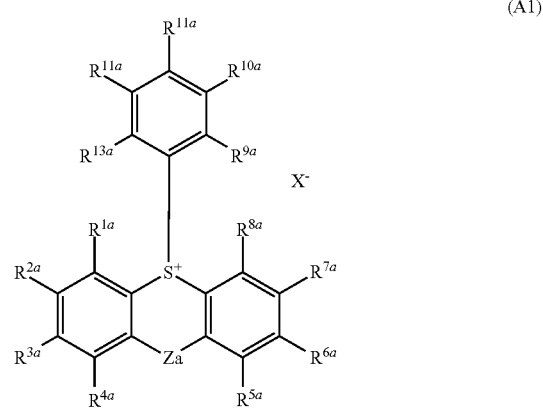

(A1)

In General Formula (A1), $R^{1a}$ to $R^{13a}$ each independently represent a hydrogen atom or a substituent.

It is preferable that one to three members out of $R^{1a}$ to $R^{13a}$ are preferably not hydrogen atoms, and it is more preferable that any one of $R^{9a}$ to $R^{13a}$ is not a hydrogen atom.

Za represents a single bond or a divalent linking group.

$X^-$ has the same meaning as $Z^-$ in General Formula (ZI).

Specific examples in a case where each of $R^{1a}$ to $R^{13a}$ is not a hydrogen atom include a halogen atom, a linear, branched, or cyclic alkyl group, an alkenyl group, an alkynyl group, an aryl group, a heterocyclic group, a cyano group, a nitro group, a carboxyl group, an alkoxy group, an aryl oxy group, a silyloxy group, a heterocyclic oxy group, an acyloxy group, a carbamoyloxy group, an alkoxycarbonyloxy group, an aryloxy carbonyloxy group, an amino group (including an anilino group), an ammonio group, an acylamino group, an aminocarbonyl amino group, an alkoxycarbonyl amino group, an aryloxy carbonyl amino group, a sulfamoyl amino group, an alkyl or arylsulfonyl amino group, a mercapto group, an alkylthio group, an arylthio group, a heterocyclic thio group, a sulfamoyl group, a sulfo group, an alkyl or aryl sulfinyl group, an alkyl or aryl sulfonyl group, an acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H), and other known substituents.

As a case where each of $R^{1a}$ to $R^{13a}$ is not a hydrogen atom, each of $R^{1a}$ to $R^{13a}$ is preferably a linear, branched, or cyclic alkyl group substituted with a hydroxyl group.

Examples of the divalent linking group of Za include an alkylene group, an arylene group, a carbonyl group, a sulfonyl group, a carbonyloxy group, a carbonylamino group, a sulfonylamide group, an ether bond, a thioether bond, an amino group, a disulfide group, —(CH$_2$)$_n$—CO—, —(CH$_2$)$_n$—SO$_2$—, —CH═CH—, an aminocarbonylamino group, and an aminosulfonylamino group (n is an integer of 1 to 3).

Moreover, examples of a preferable structure in a case where at least one of $R_{201}$, $R_{202}$, or $R_{203}$ is not an aryl group include cationic structures of compounds exemplified in paragraphs 0046 to 0048 of JP2004-233661A, paragraphs 0040 to 0046 of JP2003-35948A, and exemplified as Formulae (I-1) to (I-70) in the specification of US2003/0224288A1, and compounds exemplified as Formulae (IA-1) to (IA-54), and Formulae (IB-1) to (IB-24) in the specification of US2003/0077540A1.

In General Formulae (ZII) and (ZIII), $R_{204}$ to $R_{207}$ each independently represent an aryl group, an alkyl group, or a cycloalkyl group.

The aryl group, the alkyl group, and the cycloalkyl group of each of $R_{204}$ to $R_{207}$ are the same as the aryl group described for the aryl group, the alkyl group, and the cycloalkyl group of each of $R_{201}$ to $R_{203}$ in the compound (ZI) as described above.

The aryl group, the alkyl group, and the cycloalkyl group of each of $R_{204}$ to $R_{207}$ may have a substituent. Examples of the substituent include the substituents that the aryl group, the alkyl group, and the cycloalkyl group of each of $R_{201}$ to $R_{203}$ in the compound (ZI) as described above may have.

$Z^-$ represent a non-nucleophilic anion, and examples thereof include the same ones as the non-nucleophilic anion of $Z^-$ in General Formula (ZI).

Other examples of the acid generator include compounds represented by the following General Formulae (ZIV), (ZV), and (ZVI).

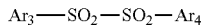

(ZIV)

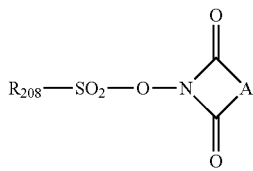

(ZV)

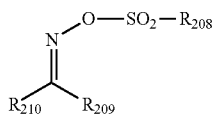

(ZVI)

In General Formulas (ZIV) to (ZVI),

Ar$_3$ and Ar$_4$ each independently represent an aryl group.

$R_{208}$, $R_{209}$, and $R_{210}$ each independently represent an alkyl group, a cycloalkyl group, or an aryl group.

A represents an alkylene group, an alkenylene group, or an arylene group.

Specific examples of the aryl group represented by Ar$_3$, Ar$_4$, $R_{208}$, $R_{209}$, or $R_{210}$ include the same as the specific examples of the aryl group of each of $R_{201}$, $R_{202}$, or $R_{203}$ in General Formula (ZI).

Specific examples of the alkyl group and the cycloalkyl group of each of $R_{208}$, $R_{209}$, and $R_{210}$ respectively include the same as the specific examples of the alkyl group and the cycloalkyl group of each of $R_{201}$, $R_{202}$, and $R_{203}$ in General Formula (ZI).

Examples of the alkylene group of A include alkylene groups having 1 to 12 carbon atoms (for example, a methylene group, an ethylene group, a propylene group, an isopropylene group, a butylene group, and an isobutylene group), examples of the alkenylene group represented by A include alkenylene groups having 2 to 12 carbon atoms (for example, an ethenylene group, a propenylene group, and a butenylene group), and examples of the arylene group represented by A include arylene groups having 6 to 10 carbon atoms (for example, a phenylene group, a tolylene group, and a naphthylene group).

In the present invention, the compound (B) that generates an acid is preferably a compound that generates an acid having a volume of 240 Angstroms$^3$ or more, more preferably a compound that generates an acid having a volume of 300 Angstroms$^3$ or more, still more preferably a compound that generates an acid having a volume of 350 Angstroms$^3$ or more, and particularly preferably a compound that generates an acid having a volume of 400 Angstroms$^3$ or more, upon irradiation with electron beams or extreme ultraviolet rays, from the viewpoint of suppressing diffusion of the acid generated by exposure to the unexposed area and improving resolution. Here, from the viewpoint of sensitivity and solubility in a coating solvent, the volume is preferably 2,000 Angstroms$^3$ or less, and more preferably 1,500 Angstroms$^3$ or less. The volume value is determined by using "WinMOPAC" manufactured by FUJITSU. That is, first, the chemical structure of the acid according to each example is input, then, using this structure as an initial structure, the most stable conformation of each acid is determined by molecular force field calculation using an MM3 method, and then, by carrying out molecular orbital calculation using a PM3 method on these most stable conformations, the "accessible volume" of each acid can be calculated.

In the present invention, an acid generator that generates an acid upon irradiation with active light or radiation is preferable. Further, calculated volume values are given to some of examples that have been extensively studied (unit Angstroms$^3$). In addition, the calculated value determined here is a volume value of an acid in which a proton is bonded to the anion moiety.

1 Angstroms is $1\times10^{-10}$ m.

585Å$^3$

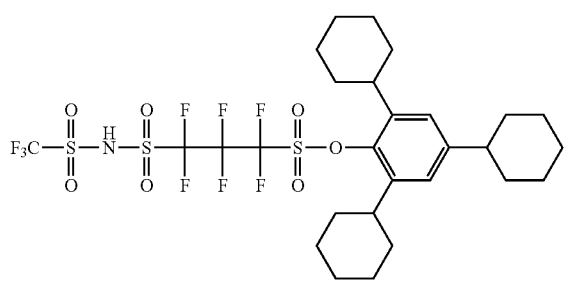

585Å³
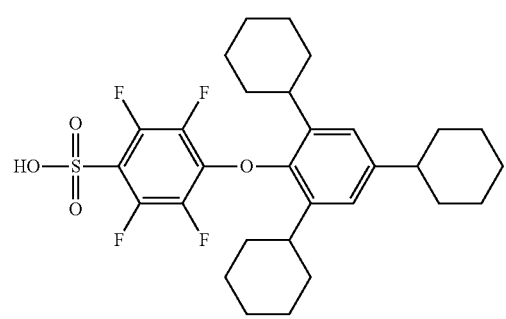
244Å³
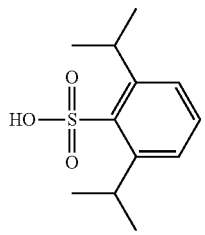
525Å³
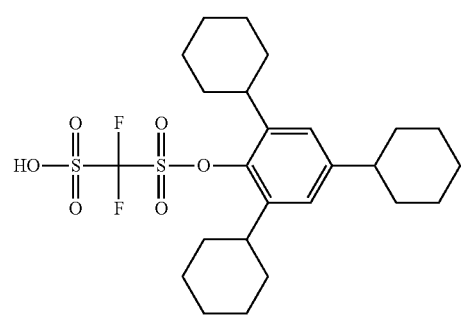
529Å³
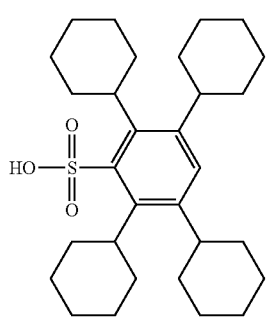
554Å³
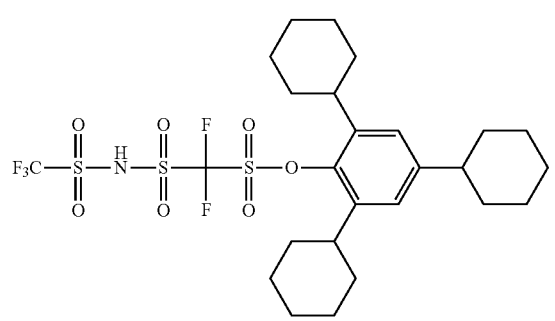
336Å³
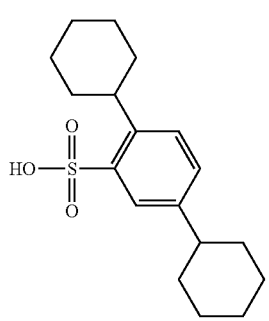
303Å³
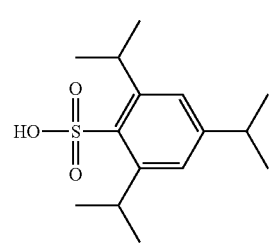
437Å³
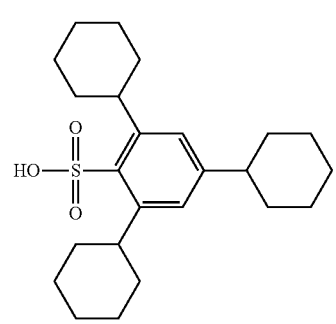
244Å³
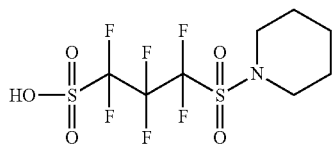
271Å³
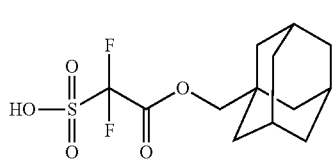

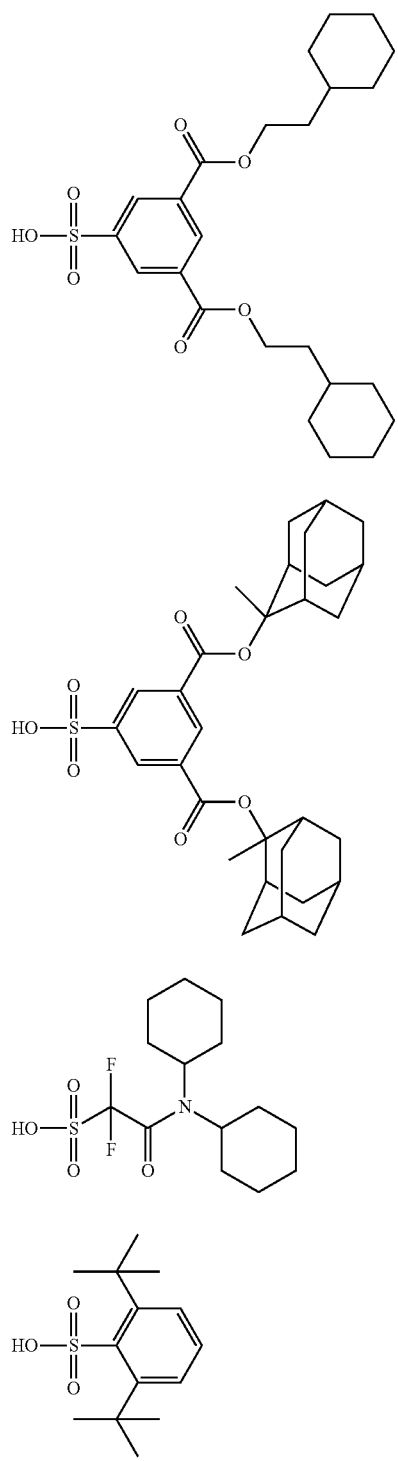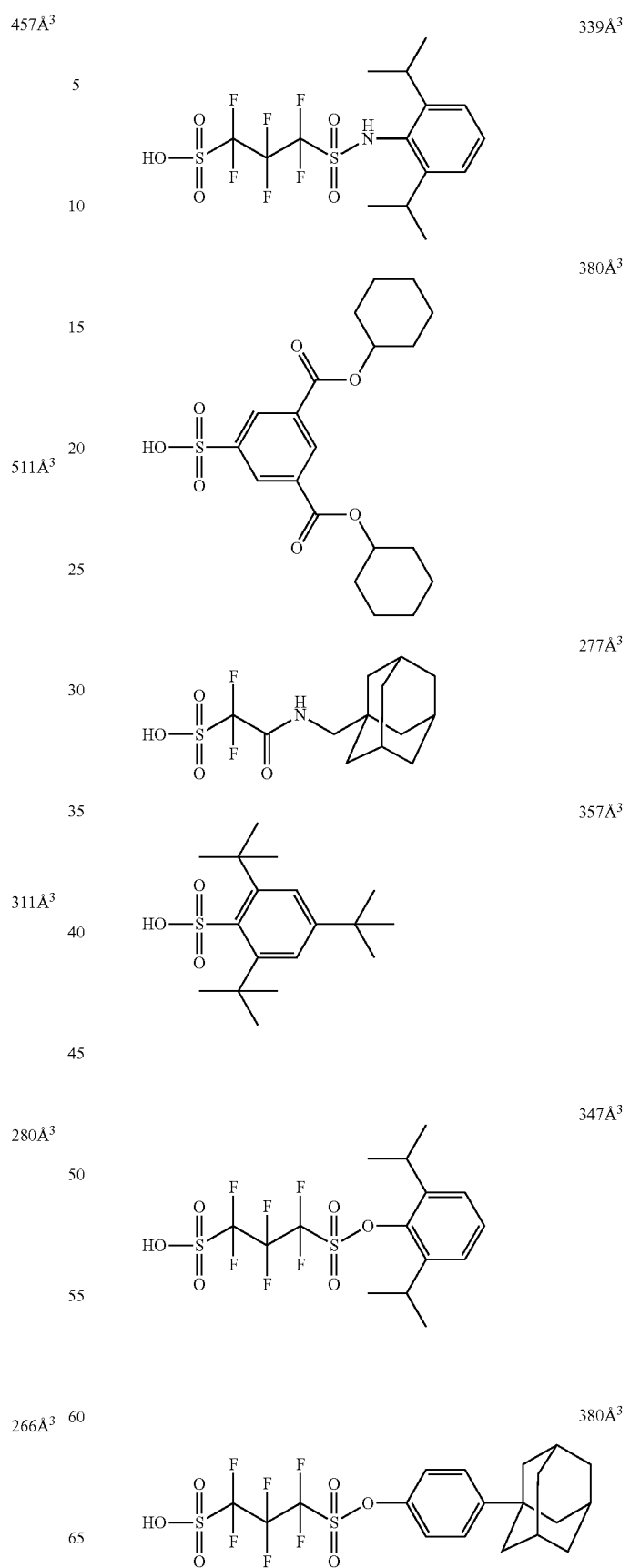

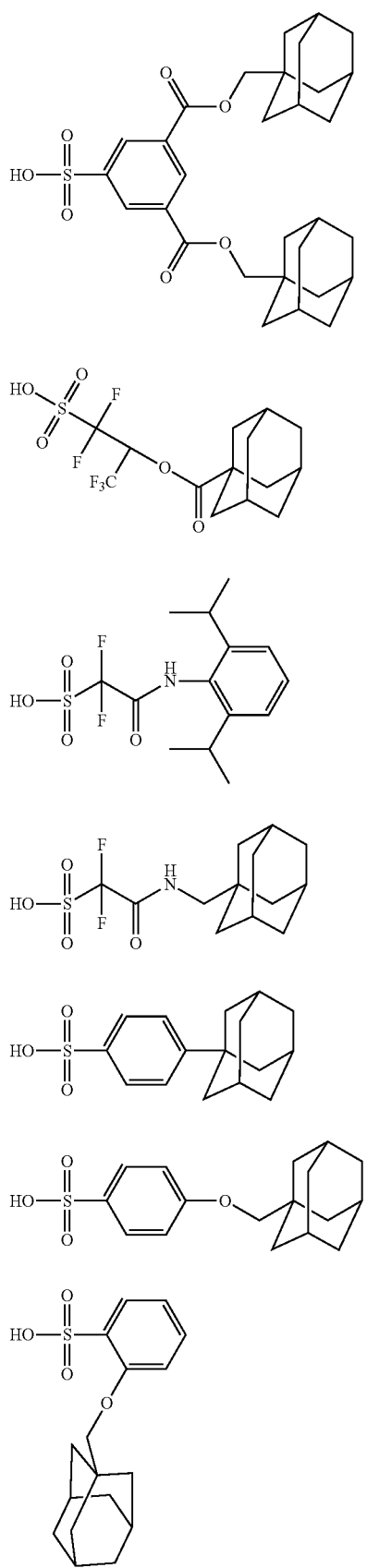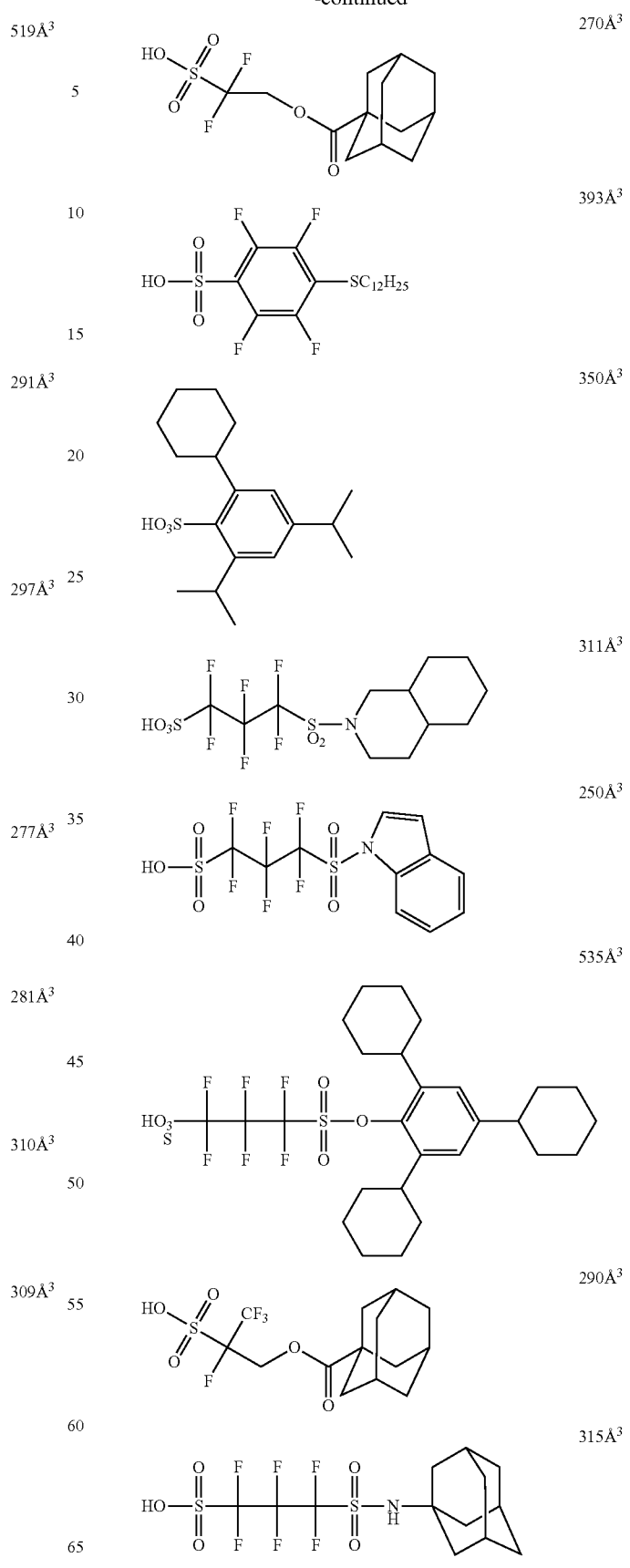

The acid generator can be used singly or in combination of two or more kinds thereof.

The content of the acid generator in the active-light-sensitive or radiation-sensitive resin composition is preferably 0.1% to 50% by mass, more preferably 5% to 50% by mass, and still more preferably 10% to 40% by mass, with respect to the total solid content of the composition. In particular, to achieve both high sensitivity and high resolution when exposure is performed by an electron beam or extreme ultraviolet rays, the content of an acid generator is preferably higher, more preferably 15% to 40% by mass, and most preferably 15% to 35% by mass.

[(C) Compound Having Cation Site and Anion Site in the Same Molecule, in which Cation Site and Anion Site are Linked to Each Other Via Covalent Bond]

The active-light-sensitive or radiation-sensitive resin composition according to the present invention preferably further includes a (C) compound having a cationic site and an anionic site in the same molecule, in which the cationic site and the anionic site are linked to each other via a covalent bond (also referred to as a "compound (C)").

As the compound (C), a compound represented by the following General Formula (C-1) is preferable.

(C-1)

$A^-$ represents an organic acid anion, L represents a single bond or a divalent linking group, and $X^+$ represents a nitrogen cation, a sulfur cation, or an iodine cation.

Rx represents an alkyl group, a cycloalkyl group, an aryl group, an aralkyl group, or a heterocyclic group. In a case where Rx's are present in plural numbers, a plurality of Rx's may be the same as or different from each other. Further, in a case where Rx's are present in plural numbers, a plurality of Rx's may be bonded to each other to form a ring, and a ring thus formed may have a nitrogen atom, an oxygen atom, or a sulfur atom as a ring member.

In a case where $X^+$ represents a nitrogen cation, n2 represents 3, in a case where $X^+$ represents a sulfur cation, n2 represents 2, and in a case where $X^+$ represents an iodine cation, n2 represents 1.

In General Formula (C-1), a conjugated base structure of the organic acid anion $A^-$ is not particularly limited, and examples thereof include conjugated base structures such as a carboxylic acid group, a sulfonic acid group, a hydroxyl group, a mercapto group, an imido group, a sulfonamido group, a sulfonimido group, a methylene compound (a malonic acid derivative, an acetoacetic acid derivative, a cyanoacetic acid derivative, a malononitrile derivative, a cyclopentadiene derivative, a bissulfonylmethane derivative, and the like), and a nitrogen-containing aromatic compound (an imidazole derivative, an indole derivative, an isocyanuric acid derivative, and the like). Among these, a carboxylic acid group or a sulfonic acid group is preferable, and a carboxylic acid group is particularly preferable.

The organic acid anion $A^-$ is not particularly limited, and is preferably a carboxylate anion or a sulfonic acid anion, and particularly preferably a carboxylate anion.

$X^+$ represents a nitrogen cation, a sulfur cation, or an iodine cation, preferably a nitrogen cation or a sulfur cation, and more preferably a nitrogen cation.

Examples of the divalent linking group of L include an alkylene group (preferably having 1 to 6 carbon atoms, and more preferably having 1 to 4 carbon atoms, such as a methylene group, an ethylene group, a propylene group, and a butylene group), a cycloalkylene group (preferably having 6 to 12 carbon atoms, and more preferably having 6 to 9 carbon atoms, such as a cyclopentylene group, a cyclohexylene group, and an adamantylene group), an arylene group (preferably having 6 to 12 carbon atoms, and more preferably having 6 to 9 carbon atoms, such as a phenylene group, a tolylene group, and a naphthylene group), an alkenylene group (preferably having 2 to 6 carbon atoms, and more preferably having 2 to 4 carbon atoms, such as an ethenylene group, a propenylene group, and a butenylene group), —COO—, —OCO—, —CO—, —O—, —S—, —SO—, —SO$_2$—, and a group composed of a combination of these two or more groups, and is preferably an alkylene group, a cycloalkylene group, an arylene group, or a group composed of a combination of these two or more groups, and more preferably an alkylene group, a cycloalkylene group, or an arylene group.

The divalent linking group for L may have a substituent.

Examples of the substituent which the divalent linking group for L can have include an alkoxy group (preferably having 1 to 15 carbon atoms), an alkylthio group (preferably having 1 to 15 carbon atoms), an alkylcarbonylamino group (preferably having 1 to 15 carbon atoms), a hydroxyl group, an alkyl group (preferably having 1 to 15 carbon atoms), a cycloalkyl group (preferably having 3 to 15 carbon atoms), an aryl group (preferably having 6 to 14 carbon atoms), a halogen atom, an acyl group (preferably having 2 to 15 carbon atoms), an acyloxy group (preferably having 2 to 15 carbon atoms), an alkoxycarbonyl group (preferably having 2 to 15 carbon atoms), a cyano group, and a nitro group.

Rx represents an alkyl group, a cycloalkyl group, an aryl group, an aralkyl group, or a heterocyclic group. From the viewpoints of improving the solubility in a solvent and relieving development defects, at least one of n2 Rx's preferably has 3 or more carbon atoms, more preferably has 5 or more carbon atoms, and still more preferably has 6 or more carbon atoms. Further, from the viewpoint of improving the resolution, Rx preferably has 10 or less carbon atoms. In addition, from the viewpoint of improving LWR, Rx preferably represents an alkyl group.

The alkyl group of Rx includes a linear or branched alkyl group having 1 to 20 carbon atoms, such as a methyl group, an ethyl group, a propyl group, an isopropyl group, an n-butyl group, a sec-butyl group, a pentyl group, a hexyl group, a 2-ethylhexyl group, an octyl group, and a dodecyl group, and an alkyl group having 5 to 10 carbon atoms is more preferable, and an alkyl group having 6 to 8 carbon atoms is still more preferable.

The cycloalkyl group of Rx may be monocyclic or polycyclic, and is preferably a cycloalkyl group having 3 to 15 carbon atoms, more preferably a cycloalkyl group having 3 to 10 carbon atoms, and still more preferably a cycloalkyl group having 3 to 6 carbon atoms. Specific examples of the cycloalkyl group of Rx include a cyclopropyl group, a cyclobutyl group, a cyclopentyl group, a cyclohexyl group, a cycloheptyl group, a cyclooctyl group, a decahydronaphthyl group, a cyclodecyl group, a 1-adamantyl group, a 2-adamantyl group, a 1-norbornyl group, and a 2-norbornyl group. The cycloalkyl group of Rx is preferably a cyclopropyl group, a cyclopentyl group, or a cyclohexyl group.

Examples of the aryl group of Rx include an aryl group having 6 to 18 carbon atoms, such as a phenyl group and a naphthyl group, and more preferably an aryl group having 6 to 10 carbon atoms.

The aralkyl group of Rx is preferably an aralkyl group having 6 to 20 carbon atoms, and more preferably an aralkyl group having 7 to 12 carbon atoms. Specific examples of the aralkyl group for Rx include a benzyl group, a phenethyl group, a naphthylmethyl group, and a naphthylmethyl group.

The heterocyclic group of Rx is preferably a heterocyclic group having 2 to 20 carbon atoms, and more preferably a heterocyclic group having 2 to 12 carbon atoms. Specific examples of the heterocyclic group of Rx include a triazolyl group, an imidazolyl group, a pyrrolyl group, a pyridyl group, a pirazyl group, a tetrahydropyranyl group, a tetrahydropyranyl group, a tetrahydrothiophenyl group, a piperidyl group, a piperazyl group, a furanyl group, a pyranyl group and a chromanyl group.

The alkyl group, the cycloalkyl group, the aryl group, the aralkyl group, and the heterocyclic group of Rx may further have a substituent.

Specific examples and preferred examples of the substituent which the alkyl group, the cycloalkyl group, the aryl group, the aralkyl group, and the heterocyclic group of Rx may further have include the same groups as the specific examples and preferred examples of the substituent which the divalent linking group represented by L can have as described above.

In a case where Rx's are present in plural numbers, a plurality of Rx's may be the same as or different from each other.

In the case where Rx's are present in plural numbers, the plurality of Rx's may be bonded to each other to form a ring, and the ring thus formed may contain a nitrogen atom, an oxygen atom, or a sulfur atom as a ring member.

Examples of the ring thus formed include cycloalkane rings such as a cyclopentane ring, a cyclohexane rung, an adamantane ring, a norbornene ring, and a norbornane ring, and hetero rings such as an imidazole ring, a piperidine ring, a tetrahydrothiophene ring, a tetrahydrothiopyran ring, and a dibenzothiophene ring. The ring may have a substituent, and specific examples of the substituent which the ring can have include the respective groups described above as the specific examples of the substituent which the divalent linking group of L can have as described above.

Examples of the case where two Rx's are bonded to each other to form a ring in a case of X⁺ being a sulfur cation include cases where the following some structures are formed.

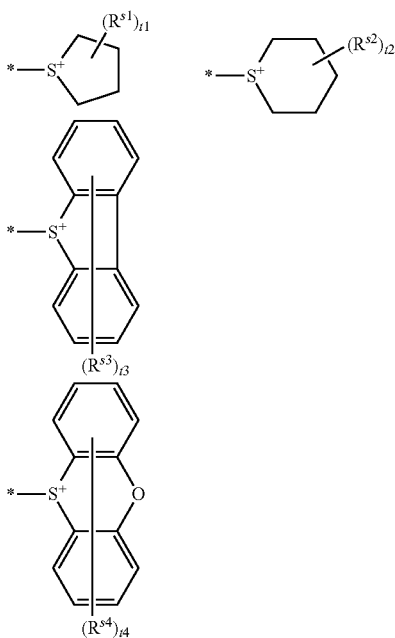

In these formulae, $R^{s1}$, $R^{s2}$, $R^{s3}$ and $R^{s4}$ each independently represent a hydroxyl group, an alkyl group having 1 to 12 carbon atoms, an alkoxy group (preferably having 1 to 12 carbon atoms), or an alicyclic hydrocarbon group (preferably having 3 to 12 carbon atoms). Further, t1 represents an integer of 0 to 4, t2 represents an integer of 0 to 5, t3 represents an integer of 0 to 8, and t4 represents an integer of 0 to 8. * represents a bonding arm. Incidentally, specific examples of each of the alkyl group, the alkoxy group, and the alicyclic hydrocarbon group as mentioned herein include the above-exemplified groups having carbon atoms in each range. Further, in these groups, regarding

one or two of the ring-constituting methylene groups may be substituted with an oxygen atom or a carbonyl group.

Examples of the case where two Rx's are bonded to each other to form a ring in a case of X⁺ being a nitrogen cation include cases where the following some structures are formed.

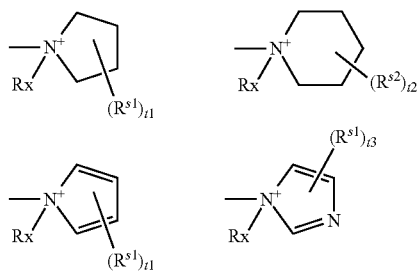

In these formulae, $R^{s1}$ and $R^{s2}$ each independently represent a hydroxyl group, an alkyl group (preferably having 1 to 12 carbon atoms), an alkoxy group (preferably having 1 to 12 carbon atoms), or an alicyclic hydrocarbon group (preferably having 3 to 12 carbon atoms). Further, t1 represents an integer of 0 to 4, t2 represents an integer of 0 to 5, and t3 represents an integer of 0 to 3. Rx represents an alkyl group, a cycloalkyl group, an aryl group, an aralkyl group, or a heterocyclic group. Incidentally, specific examples of each of the alkyl group, the alkoxy group, and the alicyclic hydrocarbon group as mentioned herein include the above-exemplified groups having carbon atoms in each range. Further, in these, regarding

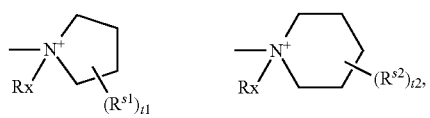

one or two of the ring-constituting methylene groups may be substituted with an oxygen atom or a carbonyl group.

For the compound represented by General Formula (C-1), the number of carbon atoms present between X⁺ and the element having negative charge among the elements constituting A⁻ is preferably 5 or less, more preferably from 0 to 4, and still more preferably from 0 to 3, from the viewpoints of the interaction of the resin (A) with the phenolic hydroxyl group can further be suppressed and the effects of the present invention can further be improved.

The compound (C) can be synthesized by a known method, and can be synthesized in accordance with methods described, for example, in "Hiroshi Horiguchi, Gosei Kaimen Kasseizai <Augmented Edition>, Sankyo Publishing Co., Ltd., 1969", "Kaimen Kasseizai Hyoka-Shikenho Henshuiinkai, Kaimen Kasseizai Hyoka-Shikenho, Gihodo Shuppan Co., Ltd., 2002", or the like.

Specific examples of the compound (C) are shown below, but the present invention is not limited thereto.

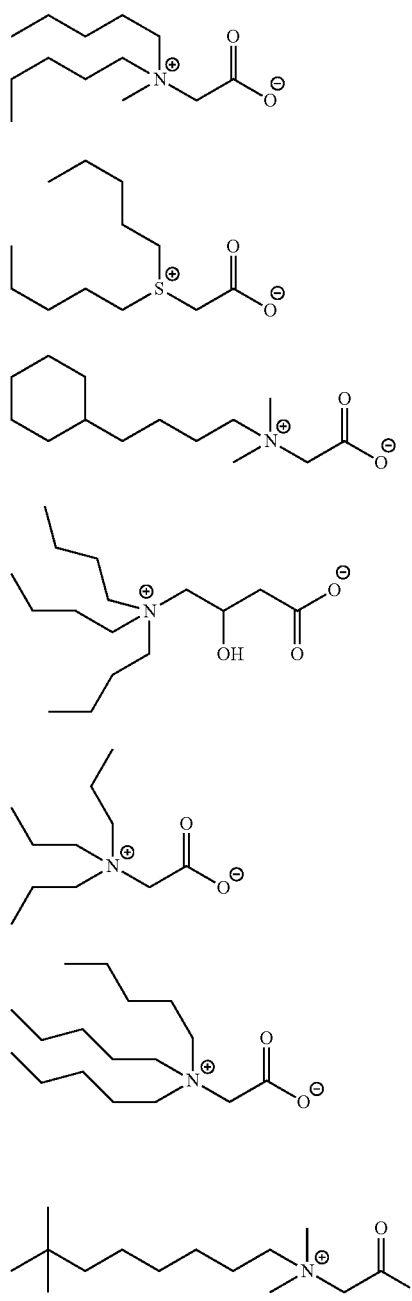

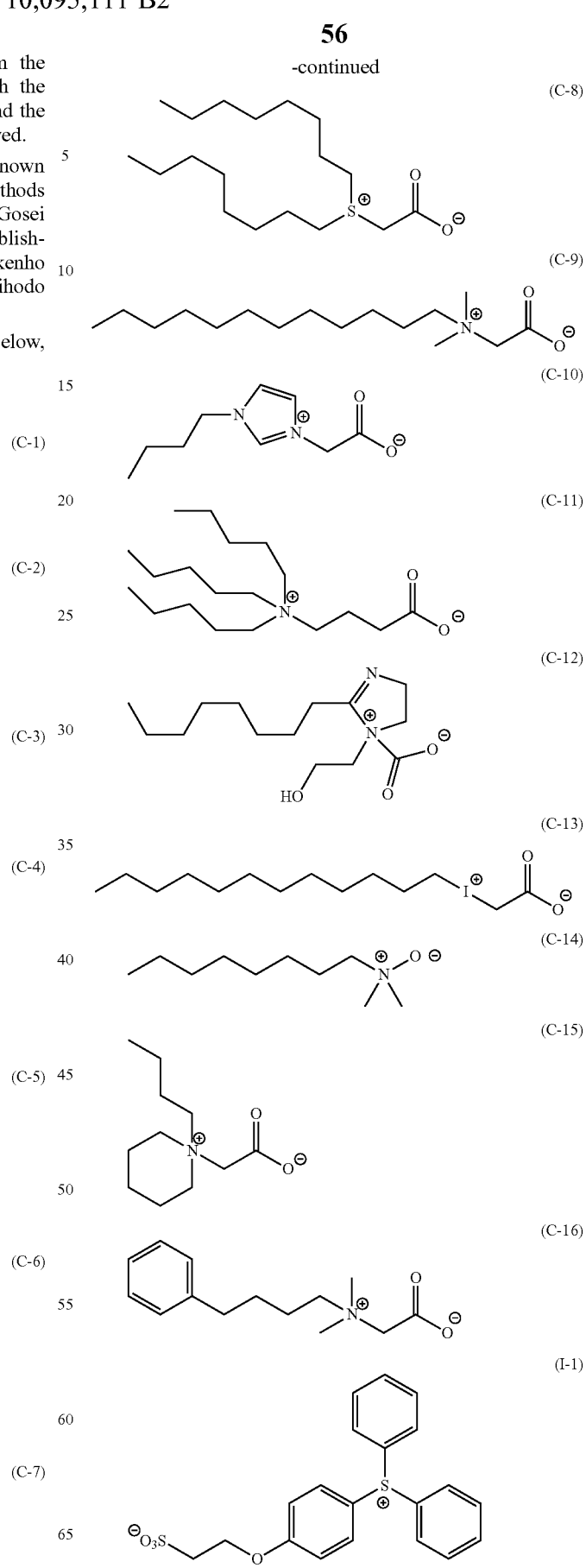

-continued
(I-2)
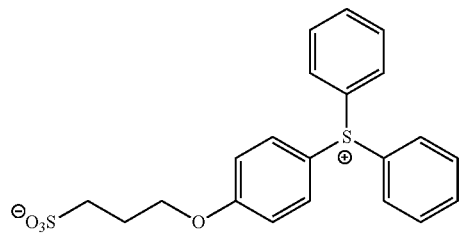
(I-3)
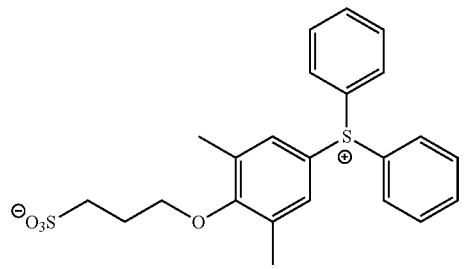
(I-4)
(I-5)
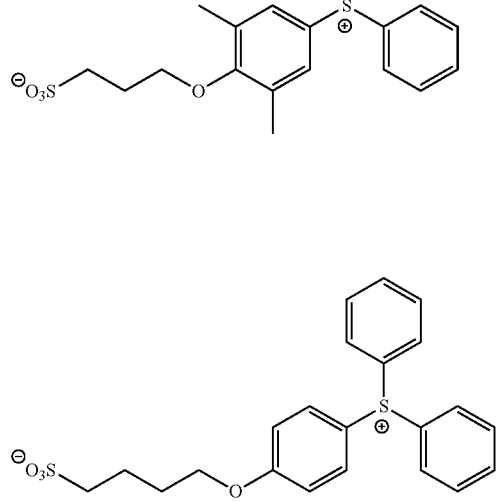
(I-6)
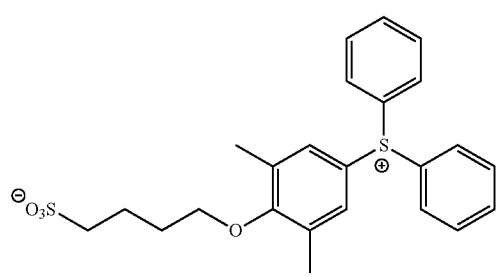
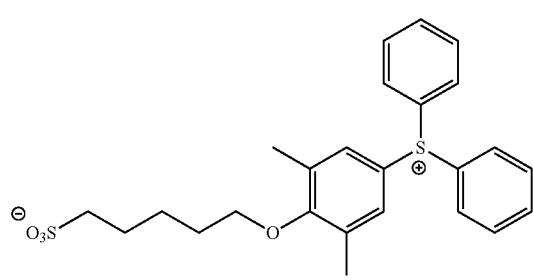
-continued
(I-7)
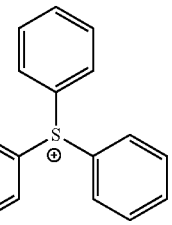
(I-8)
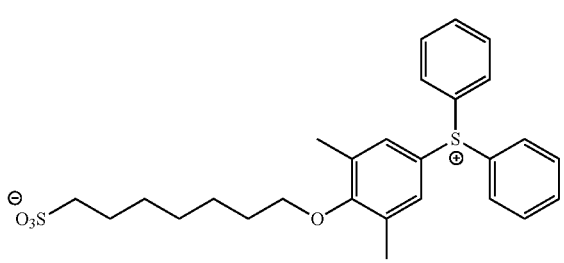
(I-9)
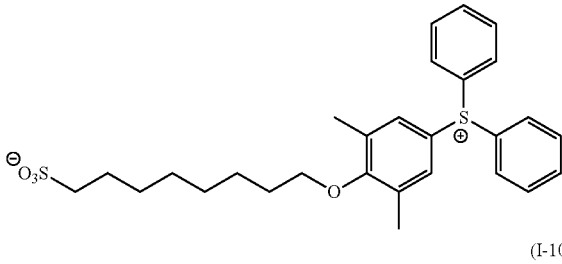
(I-10)
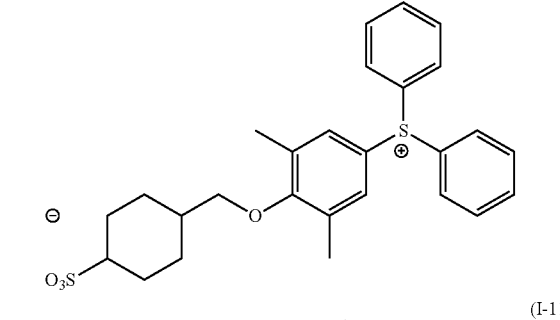
(I-11)
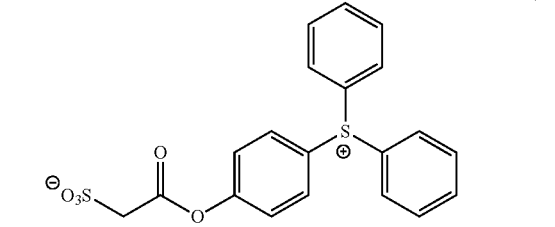
(I-12)
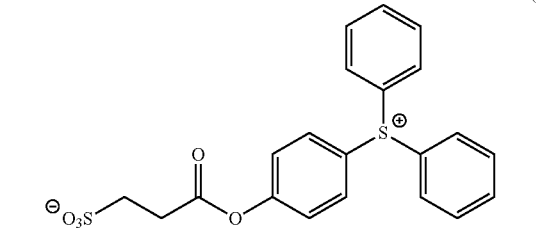

(I-13)
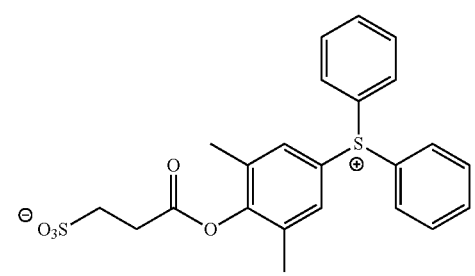
(I-14)
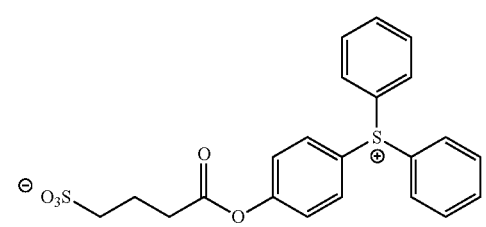
(I-15)
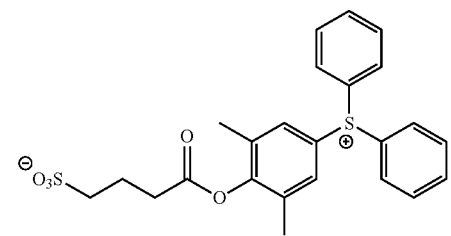
(I-16)
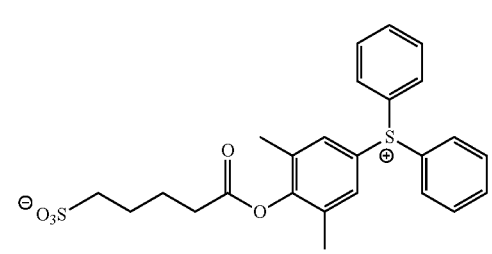
(I-17)
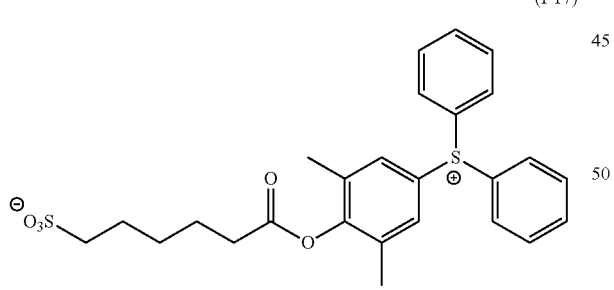
(I-18)
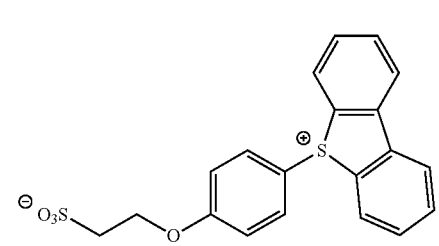
(I-19)
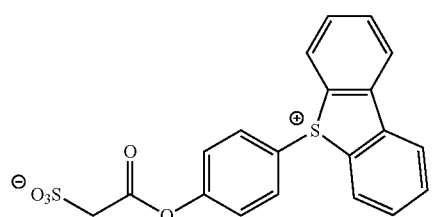
(I-20)
(I-21)
(I-22)
(I-23)
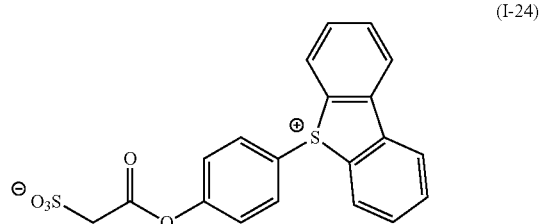
(I-24)
(I-25)
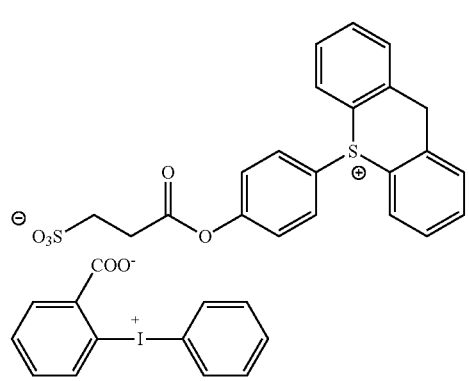

61
-continued
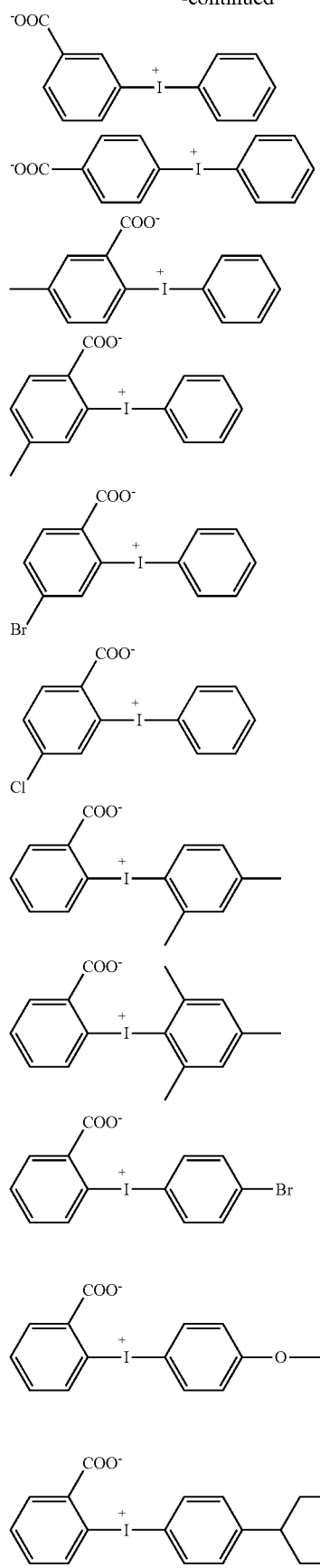
62
-continued
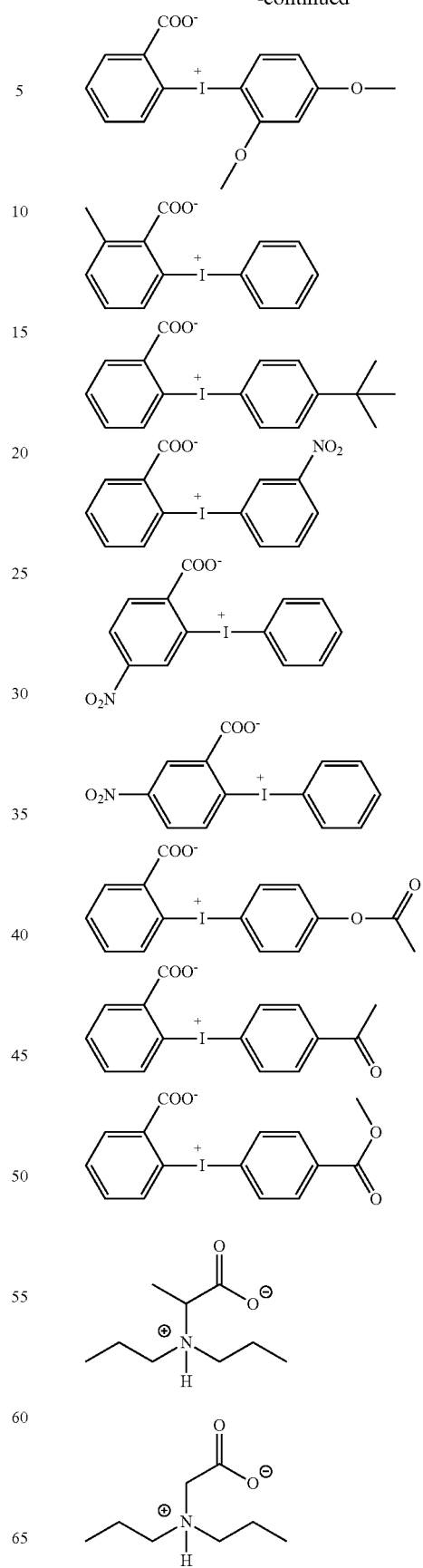

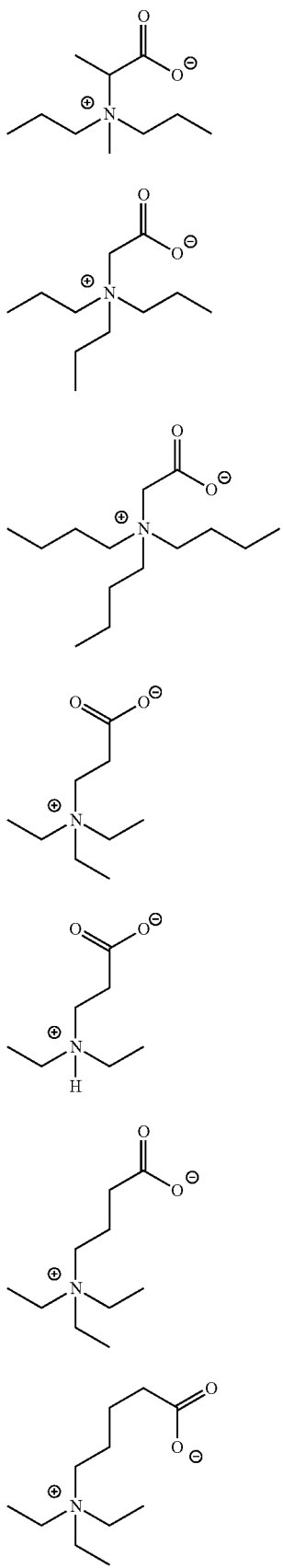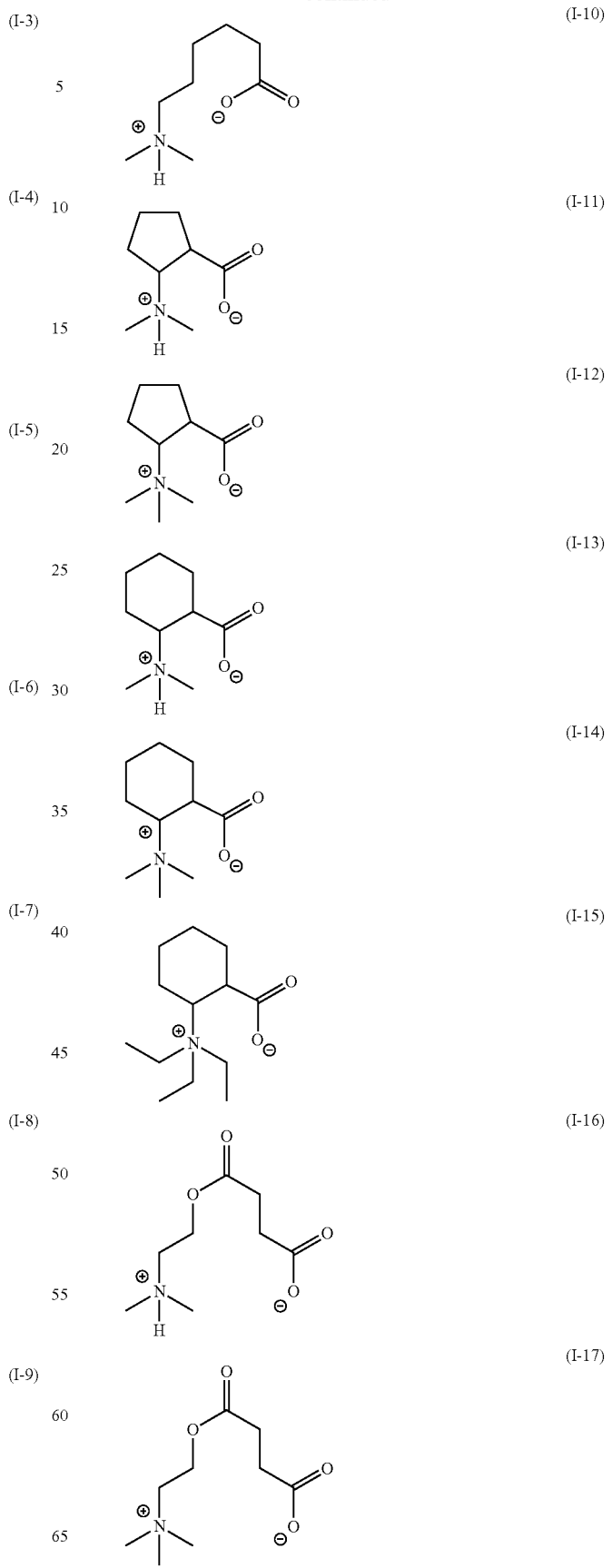

(I-18)
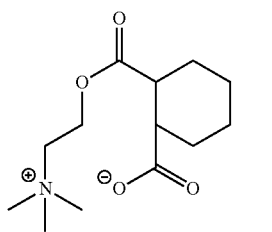

(I-19)
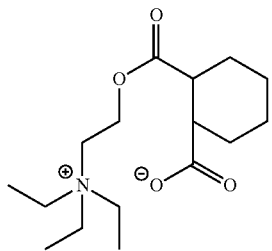

(I-20)
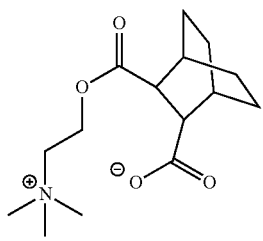

(I-31)
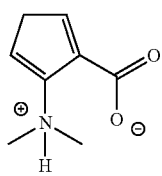

(I-32)
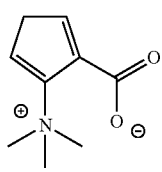

(I-33)
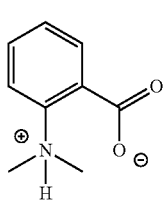

(I-34)
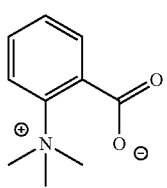

(I-35)
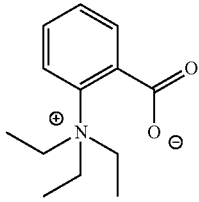

(I-31)
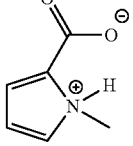

(I-32)
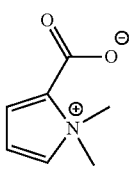

(I-33)
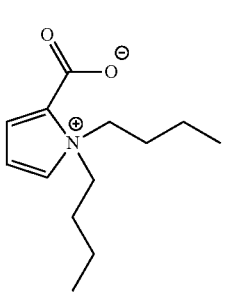

(I-34)
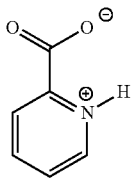

(I-35)
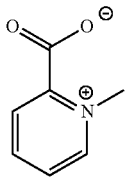

The compound (C) can be used singly or in combination of two or more kinds thereof.

The content of the compound (C) is preferably 5% by mass or less, and more preferably 1 to 4% by mass, with respect to the total solid content of the active-light-sensitive or radiation-sensitive resin composition in the present invention, from the viewpoint of reduction in shot noise.

[(C') Basic Compound]

The active-light-sensitive or radiation-sensitive resin composition according to the present invention may further include a (C') basic compound. The (C') basic compound is preferably a compound having stronger basicity, as compared to phenol. In addition, the basic compound is preferably an organic basic compound, and more preferably a nitrogen-containing basic compound.

The nitrogen-containing basic compound which can be used is not particularly limited, but the compounds which are classified into (1) to (5) below, for example, can be used.

(1) Compound Represented by General Formula (BS-1)

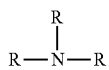
(BS-1)

In General Formula (BS-1),

R's each independently represent a hydrogen atom or an organic group. Here, at least one of three Rs is an organic group. This organic group is a linear or branched alkyl group, a monocyclic or polycyclic cycloalkyl group, an aryl group, or an aralkyl group.

The number of carbon atoms in the alkyl group as R is not particularly limited, but is normally 1 to 20, and preferably 1 to 12.

The number of carbon atoms in the cycloalkyl group as R is not particularly limited, but is normally 3 to 20, and preferably 5 to 15.

The number of carbon atoms in the aryl group as R is not particularly limited, but is normally 6 to 20, and preferably 6 to 10. Specific examples thereof include a phenyl group and a naphthyl group.

The number of carbon atoms in the aralkyl group as R is not particularly limited, but is normally 7 to 20, and preferably 7 to 11. Specifically, examples thereof include a benzyl group.

A hydrogen atom in the alkyl group, the cycloalkyl group, the aryl group, or the aralkyl group as R may be substituted with a substituent. Examples of the substituent include an alkyl group, a cycloalkyl group, an aryl group, an aralkyl group, a hydroxyl group, a carboxyl group, an alkoxy group, an aryloxy group, an alkylcarbonyloxy group, and an alkyloxycarbonyl group.

At least two members out of R's in the compound represented by General Formula (BS-1) are preferably organic groups.

Specific examples of the compound represented by General Formula (BS-1) include tri-n-butyl amine, tri-n-pentyl amine, tri-n-octyl amine, tri-n-decyl amine, triisodecyl amine, dicyclohexyl methyl amine, tetradecyl amine, pentadecyl amine, hexadecyl amine, octadecyl amine, didecyl amine, methyl octadecyl amine, dimethyl undecyl amine, N,N-dimethyl dodecyl amine, methyl dioctadecyl amine, N,N-dibutyl aniline, N,N-dihexyl aniline, 2,6-diisopropyl aniline, and 2,4,6-tri(t-butyl)aniline.

In addition, as the preferable basic compound represented by General Formula (BS-1), an alkyl group in which at least one R is substituted with a hydroxyl group is exemplified. Specific examples thereof include triethanol amine and N,N-dihydroxyethyl aniline.

The alkyl group as R may have an oxygen atom in the alkyl chain. That is, an oxyalkylene chain may be formed. As the oxyalkylene chain, —$CH_2CH_2O$— is preferable. Specific examples thereof include tris(methoxyethoxyethyl)amine and a compound disclosed after line 60 of column 3 in the specification of U.S. Pat. No. 6,040,112A.

Among the basic compounds represented by General Formula (BS-1), examples of such the compound having a hydroxyl group, an oxygen atom, or the like include the following ones.

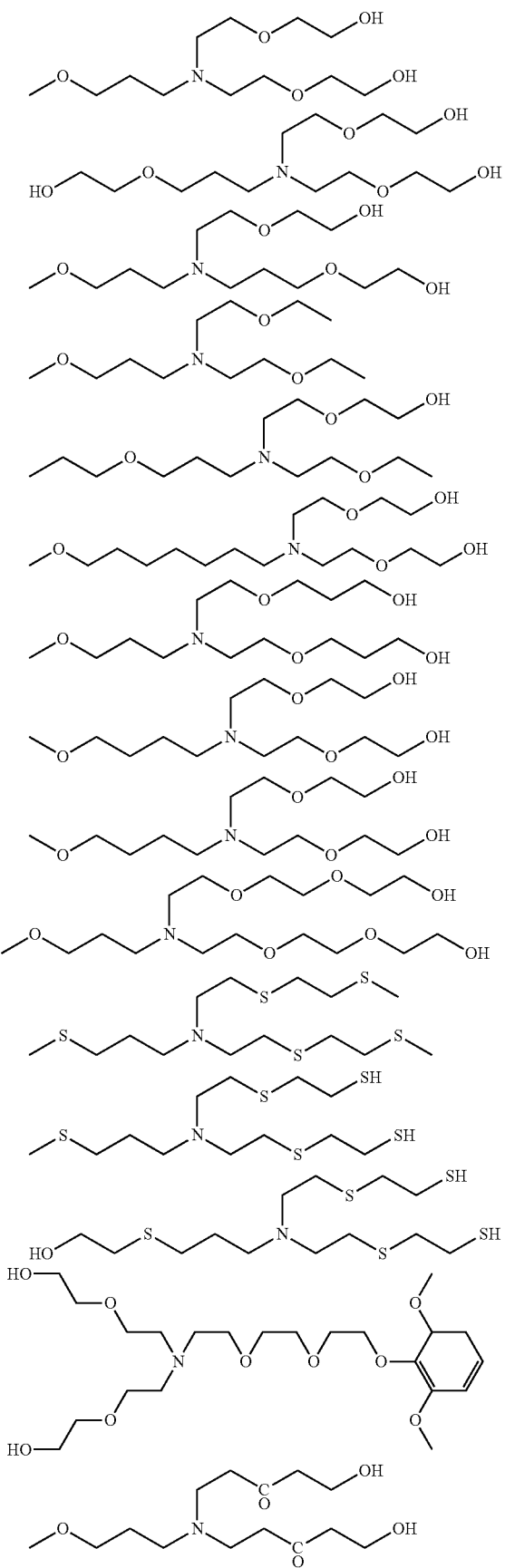

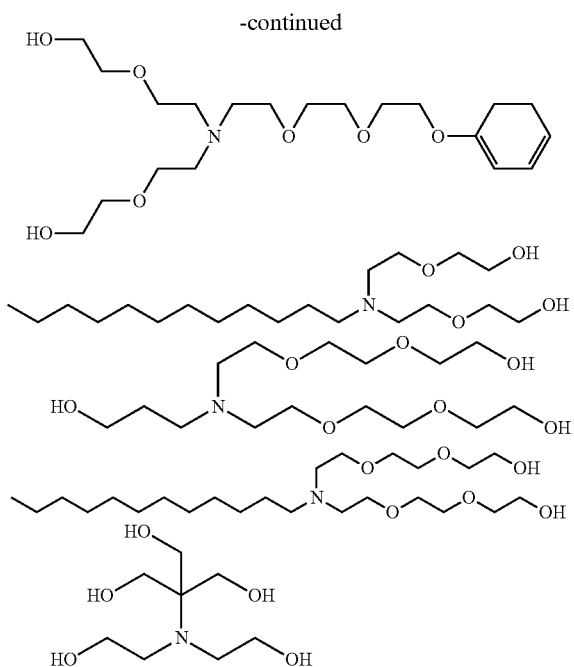

(2) Compound Having Nitrogen-Containing Heterocyclic Structure

This nitrogen-containing heterocycle may or may not have aromatic properties. The nitrogen-containing heterocycle may have a plurality of nitrogen atoms. Furthermore, the nitrogen-containing heterocycle may contain heteroatoms other than the nitrogen atom. Specific examples thereof include a compound having an imidazole structure (2-phenylbenzimidazole, 2,4,5-triphenyl imidazole and the like), a compound having a piperidine structure [N-hydroxyethylpiperidine, bis(1,2,2,6,6-pentamethyl-4-piperidyl)sebacate, and the like], a compound having a pyridine structure (4-dimethylaminopyridine and the like), and a compound having an antipyrine structure (antipyrine, hydroxyantipyrine, and the like).

Preferred examples of the compound having a nitrogen-containing heterocyclic structure include guanidine, aminopyridine, aminoalkyl pyridine, aminopyrrolidine, indazole, imidazole, pyrazole, pyrazine, pyrimidine, purine, imidazoline, pyrazoline, piperazine, aminomorpholine, and aminoalkyl morpholine. These may further have a substituent.

Preferred examples of the substituent include an amino group, an aminoalkyl group, an alkylamino group, an aminoaryl group, an arylamino group, an alkyl group, an alkoxy group, an acyl group, an acyloxy group, an aryl group, an aryloxy group, a nitro group, a hydroxyl group, and a cyano group.

Particularly preferred examples of the basic compound include imidazole, 2-methyl imidazole, 4-methyl imidazole, N-methyl imidazole, 2-phenyl imidazole, 4,5-diphenyl imidazole, 2,4,5-triphenyl imidazole, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoethylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-iminopiperidine, 1-(2-aminoethyl)pyrrolidine, pyrazole, 3-amino-5-methyl pyrazole, 5-amino-3-methyl-1-p-tolyl pyrazole, pyrazine, 2-(aminomethyl) 5-methyl pyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Furthermore, a compound having two or more ring structures can also be suitably used. Specific examples thereof include 1,5-diazabicyclo[4.3.0]non-5-ene and 1,8-diazabicyclo[5.4.0]undeca-7-ene (3) Amine Compound Having Phenoxy Group An amine compound having a phenoxy group is a compound having a phenoxy group at the terminal on the opposite side to the N atom of the alkyl group which is contained in an amine compound. The phenoxy group may have a substituent such as an alkyl group, an alkoxy group, a halogen atom, a cyano group, a nitro group, a carboxyl group, a carboxylic acid ester group, a sulfonic acid ester group, an aryl group, an aralkyl group, an acyloxy group, or an aryloxy group.

This compound more preferably has at least one oxyalkylene chain between the phenoxy group and the nitrogen atom. The number of oxyalkylene chains in one molecule is preferably 3 to 9, and more preferably 4 to 6. Among oxyalkylene chains, —$CH_2CH_2O$— is particularly preferable.

Specific examples thereof include 2-[2-{2-(2,2-dimethoxyphenoxyethoxy)ethyl}-bis-(2-methoxy-ethyl)-amine, and the compounds (C1-1) to (C3-3) exemplified in paragraph [0066] in the specification of US2007/0224539A1.

An amine compound having a phenoxy group is obtained by, for example, heating a mixture of a primary or secondary amine having a phenoxy group and an haloalkyl ether to be reacted, by adding an aqueous solution of a strong base such as sodium hydroxide, potassium hydroxide, or tetraalkylammonium thereto, and by extracting the resultant product with an organic solvent such as ethyl acetate or chloroform. In addition, an amine compound having a phenoxy group can also be obtained by heating a mixture of a primary or secondary amine and an haloalkyl ether having a phenoxy group at the terminal to be reacted, by adding an aqueous solution of a strong base such as sodium hydroxide, potassium hydroxide, or tetraalkylammonium thereto, and by extracting the resultant product with an organic solvent such as ethyl acetate or chloroform.

(4) Ammonium Salt

An ammonium salt can be appropriately used as a basic compound.

As the cation of the ammonium salt, a tetraalkylammonium cation in which an alkyl group having 1 to 18 carbon atoms is substituted is preferable, a tetramethylammonium cation, a tetraethylammonium cation, a tetra(n-butyl)ammonium cation, a tetra(n-heptyl)ammonium cation, a tetra(n-octyl)ammonium cation, a dimethylhexadecylammonium cation, or a benzyltrimethyl cation is more preferable, and tetra(n-butyl)ammonium cation is most preferable.

Examples of the anion of the ammonium salt include hydroxide, carboxylate, halide, sulfonate, borate, and phosphate. Among these, hydroxide or carboxylate is particularly preferable.

As the halide, chloride, bromide, or iodide is particularly preferable.

As the sulfonate, an organic sulfonate having 1 to 20 carbon atoms is particularly preferable. Examples of the organic sulfonate include alkyl sulfonate and aryl sulfonate having 1 to 20 carbon atoms.

The alkyl group included in the alkyl sulfonate may have a substituent. Examples of the substituent include a fluorine atom, a chlorine atom, a bromine atom, an alkoxy group, an acyl group, and an aryl group. Specific examples of the alkyl sulfonate include methanesulfonate, ethanesulfonate, butanesulfonate, hexanesulfonate, octanesulfonate, benzylsulfonate, trifluoromethanesulfonate, pentafluoroethanesulfonate, and nonafluorobutanesulfonate.

Examples of the aryl group included in the aryl sulfonate include a phenyl group, a naphthyl group, and an anthryl group. These aryl groups may have a substituent. As the substituent, for example, a linear or branched alkyl group having 1 to 6 carbon atoms or a cycloalkyl group having 3 to 6 carbon atoms is preferable. Specifically, for example, a methyl group, an ethyl group, an n-propyl group, an isopropyl group, an n-butyl group, an i-butyl group, a t-butyl group, an n-hexyl group, or a cyclohexyl group is preferable. Examples of other substituents include an alkoxy group having 1 to 6 carbon atoms, a halogen atom, a cyano group, a nitro group, an acyl group, and an acyloxy group.

The carboxylate may be aliphatic carboxylate or aromatic carboxylate, and examples thereof include acetate, lactate, pyruvate, trifluoroacetate, adamantane carboxylate, hydroxyadamantane carboxylate, benzoate, naphthoate, salicylate, phthalate, and phenolate, and in particular, benzoate, naphthoate, or phenolate is preferable, and benzoate is most preferable.

In this case, as the ammonium salt, tetra(n-butyl)ammonium benzoate, tetra(n-butyl)ammonium phenolate, or the like is preferable.

In the case of hydroxide, the ammonium salt is particularly preferably tetraalkylammonium hydroxide (tetraalkyl ammonium hydroxide such as tetramethyl ammonium hydroxide, tetraethyl ammonium hydroxide, or tetra-(n-butyl)ammonium hydroxide) having 1 to 8 carbon atoms.

(5) Low Molecular Compound Having Nitrogen Atom and Group that Leaves by Action of Acid The composition according to the present invention can contain a low molecular compound having a nitrogen atom and a group that leaves by the action of an acid. The compound preferably has basicity after a group that leaves by the action of an acid leaves.

With regard to the compound, reference can be made to the description in paragraphs [0324] to [0337] of JP2012-133331A, the contents of which are incorporated in the present specification.

In the present invention, the compound may be used singly or in mixture of two or more kinds thereof.

In addition to these, examples of the compound which can be used in the composition according to the present invention include the compounds synthesized in Examples of JP2002-363146A and the compounds described in paragraph 0108 of JP2007-298569A.

As the (C') basic compound, a photosensitive basic compound may be used. As the photosensitive basic compound, for example, the compounds described in JP2003-524799A, J. Photopolym. Sci & Tech. Vol. 8, P. 543-553 (1995), and the like as can be used.

The molecular weight of the (C') basic compound is usually 100 to 1,500, preferably 150 to 1,300, and more preferably 200 to 1,000.

These (C') basic compounds may be used singly or in combination of two or more kinds thereof.

The active-light-sensitive or radiation-sensitive resin composition according to the present invention may or may not include the (C') basic compound, but in a case of including the (C') basic compound, the content of the (C') basic compound included in the composition of the present invention is preferably 0.01% to 8.0% by mass, more preferably 0.1% to 5.0% by mass, and particularly preferably 0.2% to 4.0% by mass, with respect to the total solid content of the composition.

The molar ratio of the (C') basic compound to the photoacid generator is preferably set to 0.01 to 10, more preferably set to 0.05 to 5, and still more preferably set to 0.1 to 3. When the molar ratio is excessively large, the sensitivity and/or the resolution may be reduced in some cases. When the molar ratio is excessively small, there is a possibility that thinning of a pattern occurs, during exposure and heating (post baking). The molar ratio is more preferably 0.05 to 5, and still more preferably 0.1 to 3.

(D) Solvent

The composition according to the present invention preferably includes a solvent (D). The solvent preferably includes (S1) propylene glycol monoalkyl ether carboxylate and (S2) at least one selected from the group consisting of propylene glycol monoalkyl ether, lactic acid ester, acetic acid ester, alkoxypropionic acid ester, chain ketone, cyclic ketone, lactone, and alkylene carbonate. Further, the solvent may further include components other than the component (S1) and the component (S2).

The present inventors find that when such a solvent and the resin as described above are used in combination, coatability of a composition is improved, and a pattern having a small number of development defects can be formed. The reason is not clear, but the present inventors consider that the reason is due to the fact that, since these solvents have excellent balance among solubility with respect to the resin as described above, a boiling point, and viscosity, unevenness in the film thickness of the composition layer or the generation of precipitates during the spin coating can be suppressed.

As the component (S1), at least one selected from the group of consisting of propylene glycol monomethyl ether acetate, propylene glycol monomethyl ether propionate, and propylene glycol monoethyl ether acetate is preferable, and propylene glycol monomethyl ether acetate is particularly preferable.

As the component (S2), the following ones are preferable.

As propylene glycol monoalkyl ether, propylene glycol monomethyl ether or propylene glycol monoethyl ether is preferable.

As the lactic acid ester, ethyl lactate, butyl lactate, or propyl lactate is preferable.

As the acetic acid ester, methyl acetate, ethyl acetate, butyl acetate, isobutyl acetate, propyl acetate, isoamyl acetate, methyl formate, ethyl formate, butyl formate, propyl formate, or 3-methoxybutyl acetate is preferable.

As the alkoxypropionic acid ester, methyl 3-methoxypropionate (MMP) or ethyl 3-ethoxypropionate (EEP) is preferable.

As the chain ketone, 1-octanone, 2-octanone, 1-nonanone, 2-nonanone, acetone, 4-heptanone, 1-hexanone, 2-hexanone, diisobutyl ketone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, or methyl amyl ketone is preferable.

As cyclic ketone, methyl cyclohexanone, isophorone, or cyclohexanone is preferable.

As lactone, γ-butyrolactone is preferable.

As alkylene carbonate, propylene carbonate is preferable.

As the component (S2), propylene glycol monomethyl ether, ethyl lactate, ethyl 3-ethoxypropionate, methyl amyl ketone, cyclohexanone, butyl acetate, pentyl acetate, γ-butyrolactone, or propylene carbonate is more preferable.

As the component (S2), a component having a flash point (hereinafter, also referred to as fp) of 37° C. or higher is preferably used. As such a component (S2), propylene glycol monomethyl ether (fp: 47° C.), ethyl lactate (fp: 53° C.), ethyl 3-ethoxypropionate (fp: 49° C.), methyl amyl ketone (fp: 42° C.), cyclohexanone (fp: 44° C.), pentyl acetate (fp: 45° C.), methyl 2-hydroxyisobutyrate (fp: 45° C.), γ-butyrolactone (fp: 101° C.), or propylene carbonate (fp: 132° C.) is preferable. Among these, propylene glycol monoethyl ether, ethyl lactate, pentyl acetate, or cyclohexanone is more preferable, and propylene glycol monoethyl ether or ethyl lactate is particularly preferable. In addition, the "flash point" herein means a value described in the reagent catalog of Tokyo Chemical Industry Co., Ltd. or Sigma-Aldrich Co. LLC.

The solvent preferably includes the component (S1). It is more preferable that the solvent consists of substantially only the component (S1) or is a mixed solvent of the component (S1) and other components. In the latter case, the solvent still more preferably includes both the component (S1) and the component (S2).

The mass ratio between the component (S1) and the component (S2) is preferably in a range of 100:0 to 15:85, more preferably in a range of 100:0 to 40:60, and still more preferably in a range of 100:0 to 60:40. That is, it is preferable that the solvent consists of only the component (S1), or includes both the component (S1) and the component (S2) and the mass ratio thereof is as follows. That is, in the latter case, the mass ratio of the component (S1) to the component (S2) is preferably 15/85 or more, more preferably 40/60 or more, and still more preferably 60/40 or more. When such a configuration is adopted, the number of development defects can further be reduced.

Moreover, in a case where the solvent includes both the component (S1) and the component (S2), the mass ratio of the component (S1) with respect to the component (S2) is, for example, set to 99/1 or less.

As described above, the solvent may further include a component other than the component (S1) and the component (S2). In this case, the content of the component other than the component (S1) and the component (S2) is preferably in a range of 5% by mass to 30% by mass with respect to the total amount of the solvent.

The content of the solvent in the composition is preferably set such that the solid content concentration of all components becomes 2% to 30% by mass, and more preferably set such that the solid content concentration of all components becomes 3% to 20% by mass. Within this range, the coatability of the composition can further be improved.

[(E) Hydrophobic Resin]

The active-light-sensitive or radiation-sensitive resin composition in the present invention may contain a hydrophobic resin (E), in addition to the resin (A).

Although the hydrophobic resin is preferably designed to be unevenly localized on the surface of the resist film, it does not necessarily have to have a hydrophilic group in its molecule as different from a surfactant, and does not need to contribute to uniform mixing of polar/nonpolar materials.

Examples of the effect of addition of the hydrophobic resin include control of the static/dynamic contact angle of the resist film surface with respect to water, improvement of the immersion liquid tracking properties, and suppression of out gas.

The hydrophobic resin preferably has at least one of a "fluorine atom", a "silicon atom", or a "$CH_3$ partial structure which is contained in a side chain portion of a resin" from the viewpoint of uneven distribution on the film surface layer, and more preferably has two or more kinds. Further, the hydrophobic resin preferably contains a hydrocarbon group having 5 or more carbon atoms. These groups may be included in the main chain or the side chain of the resin.

In a case where hydrophobic resin includes a fluorine atom and/or a silicon atom, the fluorine atom and/or the silicon atom in the hydrophobic resin may be included in the main chain or the side chain of the resin.

In a case where the hydrophobic resin includes a fluorine atom, the resin is preferably a resin which has an alkyl group having a fluorine atom, a cycloalkyl group having a fluorine atom, or an aryl group having a fluorine atom, as a partial structure having a fluorine atom.

The alkyl group having a fluorine atom (preferably having 1 to 10 carbon atoms, and more preferably having 1 to 4 carbon atoms) is a linear or branched alkyl group in which at least one hydrogen atom is substituted with a fluorine atom, and may further have a substituent other than a fluorine atom.

The cycloalkyl group having a fluorine atom is a monocyclic or polycyclic cycloalkyl group in which at least one hydrogen atom is substituted with a fluorine atom, and may further have a substituent other than a fluorine atom.

The aryl group having a fluorine atom is an aryl group in which at least one hydrogen atom is substituted with a fluorine atom, and they may further have a substituent other than a fluorine atom.

Examples of the repeating unit having a fluorine atom or a silicon atom include those exemplified in paragraph 0519 of US2012/0251948A1.

In addition, as described above, it is also preferable that the hydrophobic resin includes a $CH_3$ partial structure in the side chain portion.

Here, a $CH_3$ partial structure which an ethyl group, a propyl group, or the like has is contained in a $CH_3$ partial structure which the side chain portion in the hydrophobic resin has.

On the other hand, since a methyl group (for example, an α-methyl group of a repeating unit having a methacrylic acid structure) which is directly bonded to the main chain of the hydrophobic resin does not largely contribute to the surface uneven distribution of the hydrophobic resin due to the influence of the main chain, the methyl group is not included in the $CH_3$ partial structure in the present invention.

With regard to the hydrophobic resin, reference can be made to descriptions of [0348] to [0415] of JP2014-010245A, the contents of which are incorporated in the present specification.

Moreover, in addition to the above hydrophobic resins, the hydrophobic resins described in JP2011-248019A, JP2010-175859A, or JP 2012-032544A can also be preferably used.

In the pattern forming method of the present invention, a resist film can be formed on a substrate, using the active-light-sensitive or radiation-sensitive resin composition, and a top coat layer can be formed on the resist film using the top coat composition. The film thickness of the resist film is preferably 10 to 100 nm, and the film thickness of the top coat layer is preferably 10 to 200 nm, more preferably 20 to 100 nm, and particularly preferably 40 to 80 nm.

As a method for coating the active-light-sensitive or radiation-sensitive resin composition onto a substrate, spin coating is preferable, and the rotation speed is preferably 1,000 to 3,000 rpm.

For example, the active-light-sensitive or radiation-sensitive resin composition is coated on a substrate (for example, a silicon/silicon dioxide-coated substrate) used in the manufacture of a precision integrated circuit element, an imprint mold or the like, by using a spinner, a coater, or the like. Further, an antireflection film that is already provided can also be coated. In addition, it is preferable to dry the resist film prior to the formation of the top coat layer.

Then, the top coat composition can be coated and dried by the same means as the method for forming the resist film on the obtained resist film to form a top coat layer.

The resist film having the top coat layer on the upper layer there is usually irradiated with electron beams (EB), X-rays, or EUV light through a mask, and are preferably baked (heated) and developed, thereby obtaining a good pattern.

[(F) Surfactant]

The composition according to the present invention may further include a surfactant (F). By incorporating the surfactant into the composition, it becomes possible to form a pattern which is improved in adhesiveness and decreased in development defects with good sensitivity and resolution in a case of using a light source for exposure of 250 nm or less, and particularly 220 nm or less.

As the surfactant, a fluorine-based and/or silicon-based surfactant is/are particularly preferably used.

Examples of the fluorine- and/or silicon-based surfactants include the surfactants described in [0276] of US2008/0248425A. Other examples of the surfactants include EFTOP EF301 or EF303 (manufactured by Shin-Akita Kasei K. K.); FLORAD FC430, 431, or 4430 (manufactured by Sumitomo 3M Inc.); MEGAFACE F171, F173, F176, F189, F113, F110, F177, F120, or R08 (manufactured by DIC Corp.); SURFLON S-382, SC101, 102, 103, 104, 105, or 106 (manufactured by Asahi Glass Co., Ltd.); TROYSOL S-366 (manufactured by Troy Chemical Corp.); GF-300 or GF-150 (manufactured by Toagosei Chemical Industry Co., Ltd.); SURFLON S-393 (manufactured by Seimi Chemical Co., Ltd.); EFTOP EF121, EF122A, EF122B, RF122C, EF125M, EF135M, EF351, EF352, EF801, EF802, or EF601 (manufactured by JEMCO Inc.); KH-20 (manufactured by Asahi Glass Co., Ltd.); PF636, PF656, PF6320, or PF6520 (manufactured by OMNOVA); and FTX-204G, 208G, 218G, 230G; 204D, 208D, 212D, 218D, or 222D (manufactured by NEOS Co., Ltd.). In addition, Polysiloxane Polymer KP-341 (manufactured by Shin-Etsu Chemical Co., Ltd.) can also be used as the silicon-based surfactant.

Furthermore, in addition to those known surfactants as described above, surfactants may also be synthesized using a fluoro-aliphatic compound which is produced by a telomerization method (also referred to as a telomer method) or an oligomerization method (also referred to as an oligomer method). Specifically, a polymer including a fluoro-aliphatic group derived from the fluoro-aliphatic compound may also be used as the surfactant. The fluoro-aliphatic compound can be synthesized in accordance with the method described in JP2002-90991A.

In addition, a surfactant other than the fluorine- and/or silicon-based surfactants described in 0280 of US2008/0248425A may also be used.

These surfactants may be used singly or in combination of two or more kinds thereof.

In a case where the composition according to the present invention includes a surfactant, the content of the surfactant is preferably 0% to 2% by mass, more preferably 0.0001% to 2% by mass, and still more preferably 0.0005% to 1% by mass, with respect to the total solid content amount of the composition.

[(G) Other Additives]

The composition according to the present invention may further include a dissolution inhibiting compound, a dye, a plasticizer, a light sensitizer, a light absorbent, and/or a compound promoting solubility in a developer (for example, a phenol compound having a molecular weight of 1,000 or less, and an alicyclic or aliphatic compound including a carboxyl group).

The composition according to the present invention may further include a dissolution inhibiting compound. Here, the "dissolution inhibiting compound" is a compound having a molecular weight of 3,000 or less, that decomposes by the action of an acid, and thus, has a reduced solubility in an organic developer.

As the dissolution inhibiting compound, an alicyclic or aliphatic compound which contains an acid-decomposable group such as a cholic acid derivative which including an acid-decomposable group described in the Proceeding of SPIE, 2724, 355 (1996) is preferable since the transparency with respect to light having a wavelength of 220 nm or less is not reduced. Examples of the acid-decomposable group and the alicyclic structure include the same as those described above, respectively.

EXAMPLES

Hereinbelow, the present invention will be described with reference to Examples, but the present invention is not limited thereto.

As the resin (A), resins A-1 to A-17 were used. The resins A-1 to A-17 were synthesized in accordance with JP2013-8020A. Further, A-18 was used as a resin for Comparative Examples. The structure, the weight-average molecular weight (Mw), and the dispersity (Mw/Mn) of each of the resins A-1 to A-18 are shown below. The ratios of the repeating units represent molar ratios.

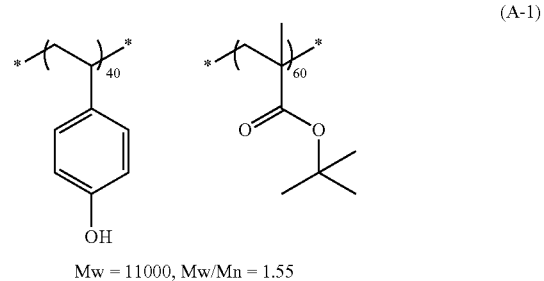

(A-1)

Mw = 11000, Mw/Mn = 1.55

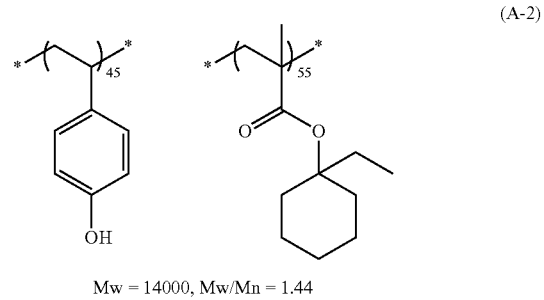

(A-2)

Mw = 14000, Mw/Mn = 1.44

-continued
(A-3)
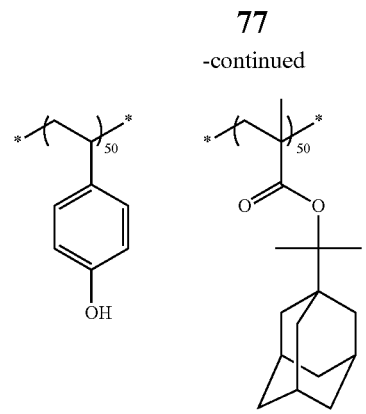
Mw = 10000, Mw/Mn = 1.51
(A-4)
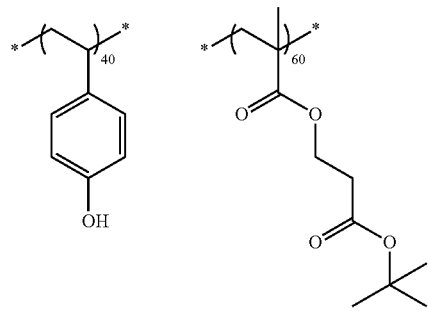
Mw = 12000, Mw/Mn = 1.48
(A-5)
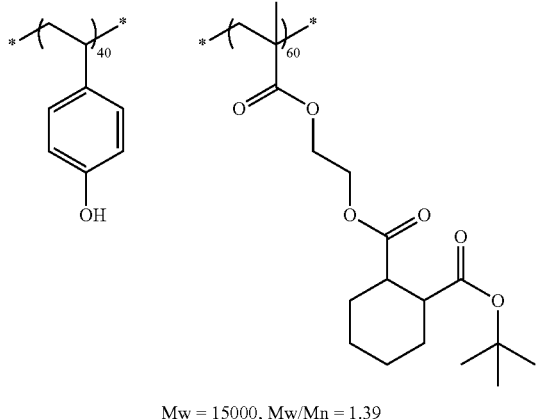
Mw = 15000, Mw/Mn = 1.39
(A-6)
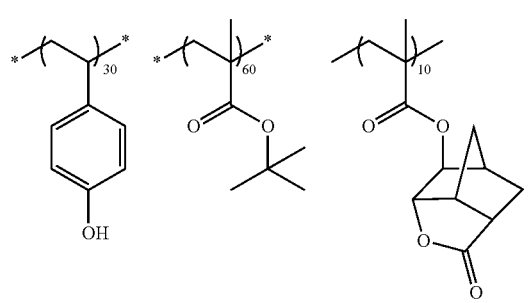
Mw = 12000, Mw/Mn = 1.59
-continued
(A-7)
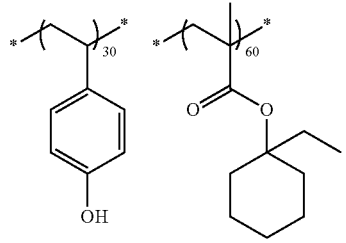
Mw = 11000, Mw/Mn = 1.54
(A-8)
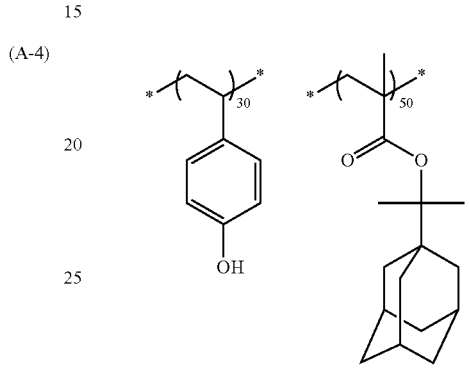
Mw = 15000, Mw/Mn = 1.64
(A-9)
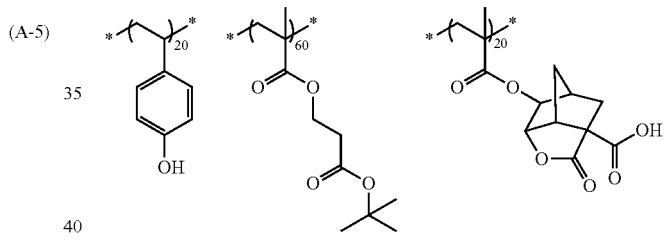
Mw = 18000, Mw/Mn = 1.61
(A-10)
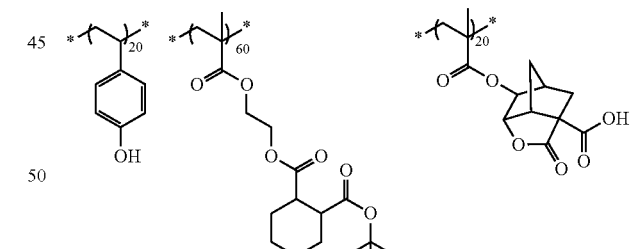
Mw = 17000, Mw/Mn = 1.55
(A-11)
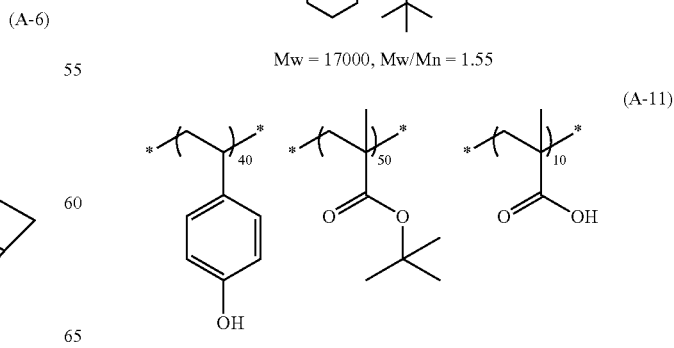
Mw = 13000, Mw/Mn = 1.56

(A-12)
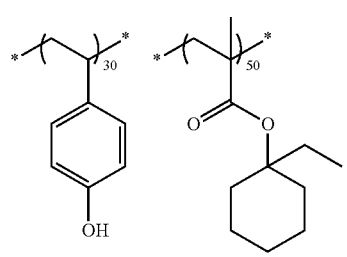
Mw = 11000, Mw/Mn = 1.43
(A-13)
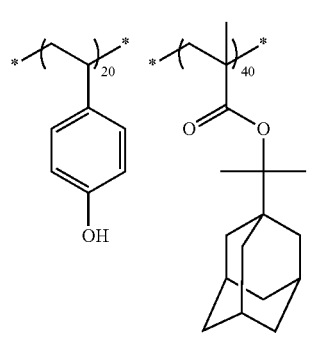
Mw = 12000, Mw/Mn = 1.51
(A-14)
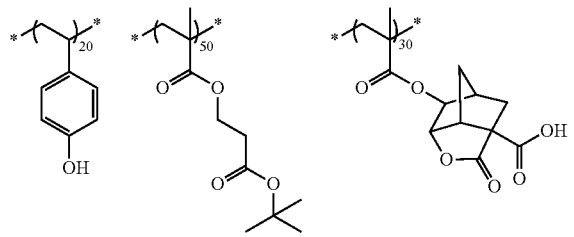
Mw = 14000, Mw/Mn = 1.52
(A-15)
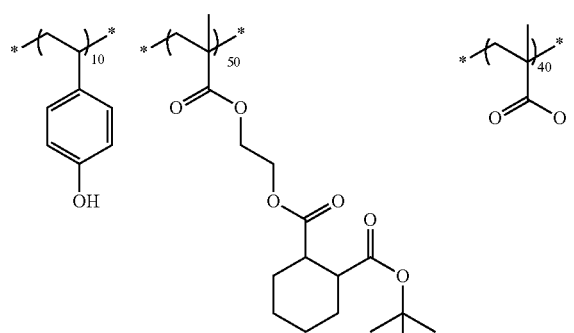
Mw = 15000, Mw/Mn = 1.54
(A-16)
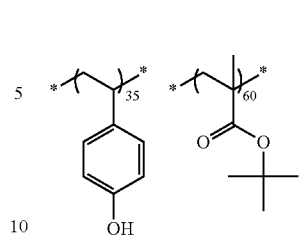
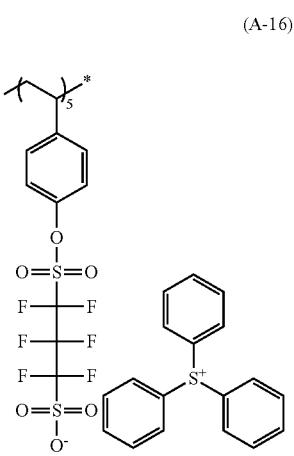
Mw = 10000, Mw/Mn = 1.75
(A-17)
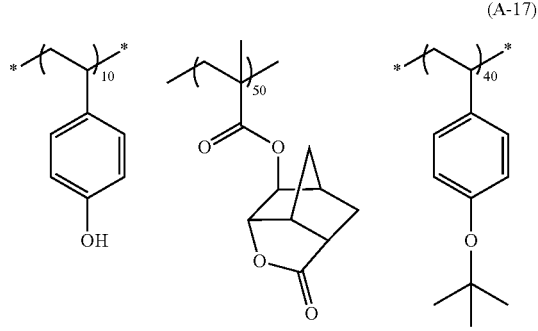
Mw = 13000, Mw/Mn = 1.57
(A-18)
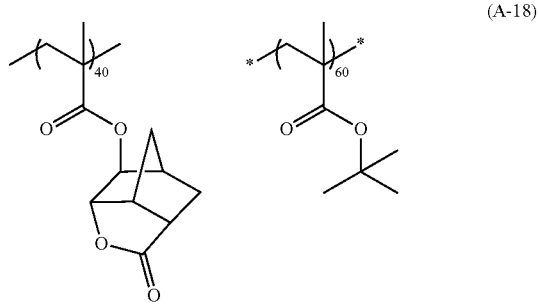
Mw = 14000, Mw/Mn = 1.53
As the acid generator (B), the following B-1 to B-12 were used.
(B-1)
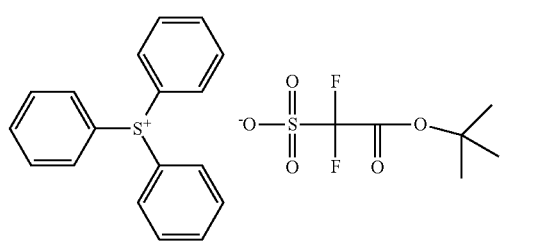

-continued
(B-2)
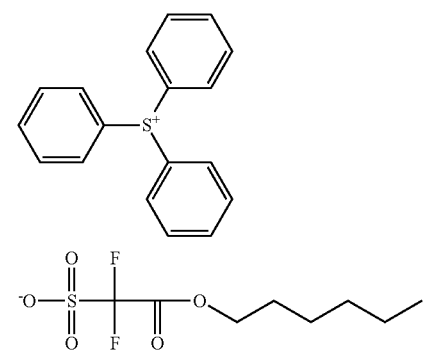
(B-3)
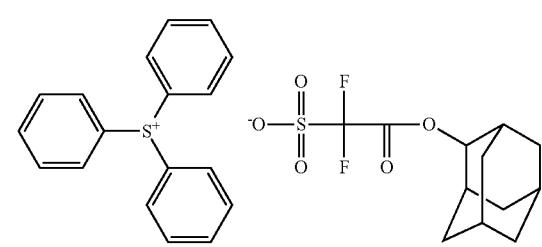
(B-4)
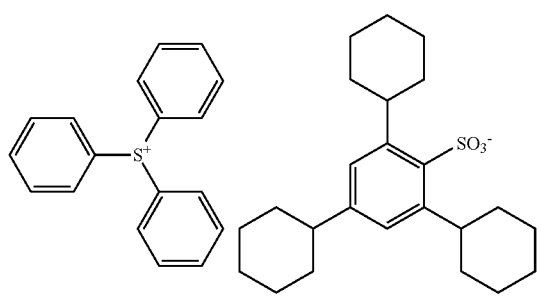
(B-5)
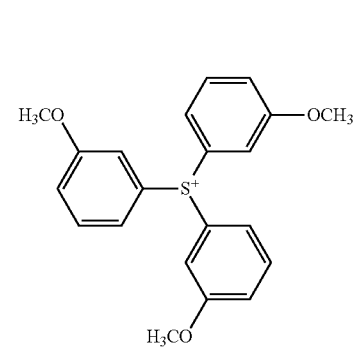
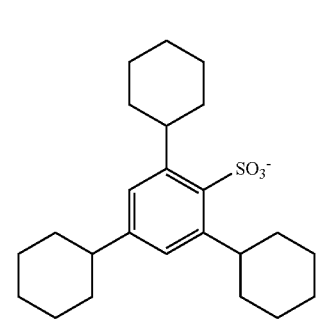
-continued
(B-6)
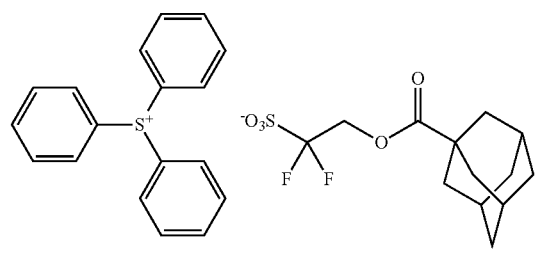
(B-7)
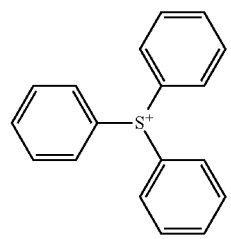
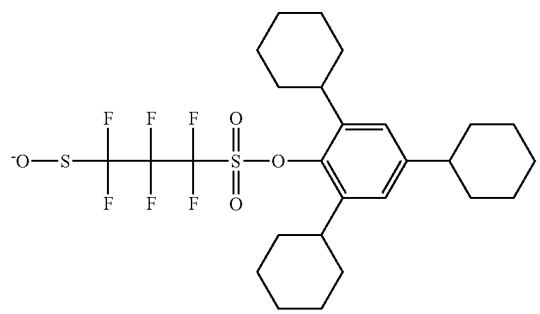
(B-8)
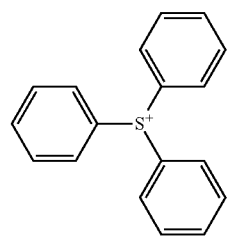
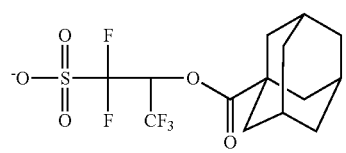
(B-9)
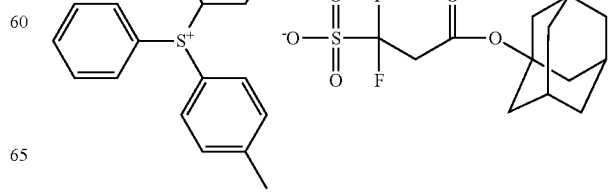

(B-10)
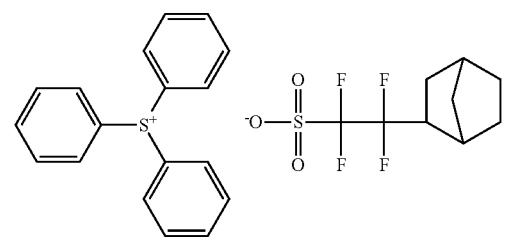
(B-11)
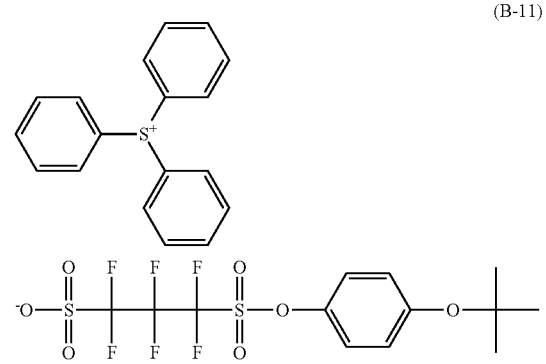
(B-12)
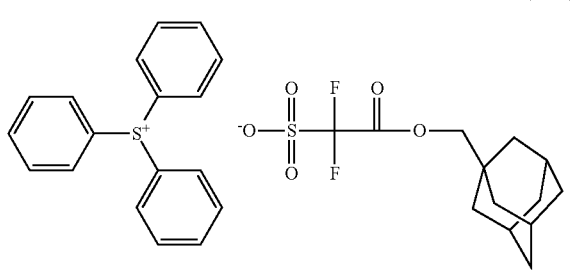
As the compound (C), the following C-1 to C-16 were used.
(C-1)
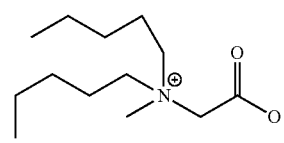
(C-2)
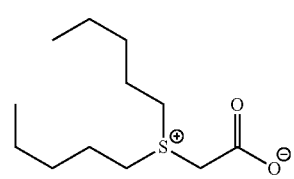
(C-3)
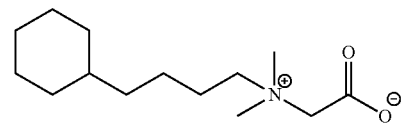
(C-4)
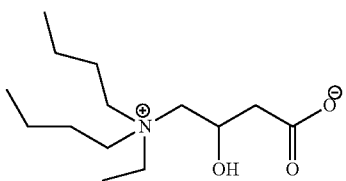
(C-5)
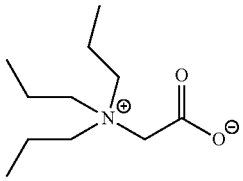
(C-6)
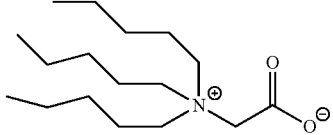
(C-7)
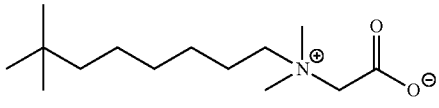
(C-8)
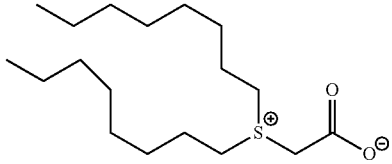
(C-9)
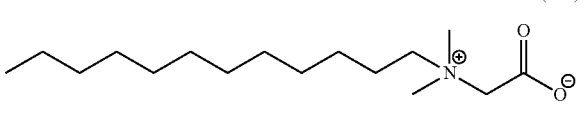
(C-10)
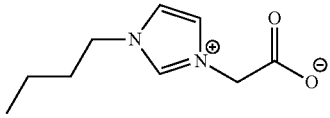
(C-11)
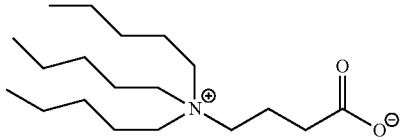
(C-12)
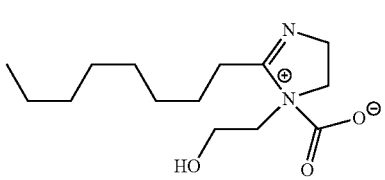
(C-13)
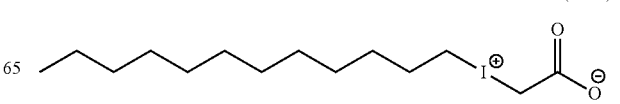

If necessary, a basic compound Q-1 shown below was used.

Q-1: Tetrabutylammonium hydroxide

As the surfactant, the following ones were used.

W-1: MEGAFACE F176 (manufactured by DIC, Inc.; fluorine-based)

W-2: MEGAFACE R08 (manufactured by DIC, Inc.; fluorine- and silicon-based)

W-3: Polysiloxane Polymer KP-341 (manufactured by Shin-Etsu Chemical Co., Ltd.) (silicon-based)

W-4: TROYSOL S-366 (manufactured by Troy Chemical Co., Ltd.)

W-5: KH-20 (manufactured by Asahi Glass Co., Ltd.)

W-6: PolyFox™ PF-6320 (manufactured by OMNOVA Solution Inc.) (fluorine-based)

As the solvent, the following ones were used.

Group a

SL-1: Propylene glycol monomethyl ether acetate (PGMEA)

SL-2: Propylene glycol monomethyl ether propionate

SL-3: 2-Heptanone

Group b

SL-4: Ethyl lactate

SL-5: Propylene glycol monomethyl ether (PGME)

SL-6: Cyclohexanone

Group c

SL-7: γ-Butyrolactone

SL-8: Propylene carbonate

<Preparation of Resist Composition>

The components shown in Table 1 below were dissolved in the solvents shown in Table 1 below, and each of the solutions was filtered through a filter having a pore size of 0.03 to prepare a resist composition of each of Examples 1 to 29, and Comparative Examples 1 and 2. In addition, Further, the parts by mass of the respective components and solvents are shown in Table 1.

TABLE 1

| | Resin (A) | | Acid generator (B) | | Compound (C) | | Basic compound (C') | | Surfactant | | Solvent (D) | |
|---|---|---|---|---|---|---|---|---|---|---|---|---|
| | Compound No. | Parts by mass | Compound No. | Parts by mass | Compound No. | Parts by mass | Compound No. | Parts by mass | Compound No. | Parts by mass | Compound No. | Parts by mass |
| Example 1 | A-6 | 42 | B-6 | 7 | C-6 | 1 | | | | | SL-1/SL-2 | 2,200/250 |
| Example 2 | A-6 | 43 | B-6 | 6 | C-6 | 1 | | | | | SL-1/SL-2 | 2,200/250 |
| Example 3 | A-11 | 40 | B-7 | 8 | C-9 | 1 | | | W-1 | 1 | SL-1/SL-3 | 2,000/450 |
| Example 4 | A-1 | 41 | B-12 | 8 | C-3 | 1 | | | | | SL-1/SL-6 | 2,000/450 |
| Example 5 | A-11 | 40 | B-6 | 9 | C-12 | 1 | | | | | SL-1/SL-2 | 2,200/250 |
| Example 6 | A-6/A-8 | 30/14 | B-3 | 5 | C-6 | 1 | | | | | SL-1/SL-2 | 2,200/250 |
| Example 7 | A-9 | 43 | B-1 | 6 | C-9 | 1 | | | | | SL-1/SL-2/SL-5 | 2,200/150/100 |
| Example 8 | A-7 | 42 | B-6 | 7 | C-2 | 1 | | | | | SL-1/SL-2 | 2,200/250 |
| Example 9 | A-2 | 42 | B-6 | 5 | C-6 | 1 | Q-1 | 1 | W-2 | 1 | SL-1/SL-4 | 2,100/350 |
| Example 10 | A-12 | 39 | B-8 | 10 | C-4 | 1 | | | | | SL-1/SL-2 | 2,200/250 |
| Example 11 | A-6 | 38 | B-2 | 10 | C-6 | 2 | | | | | SL-1/SL-4 | 2,100/350 |
| Example 12 | A-5 | 37 | B-3/B-6 | 5/5 | C-11 | 2 | | | W-5 | 1 | SL-1/SL-3 | 2,000/450 |
| Example 13 | A-5 | 37 | B-6 | 12 | C-13 | 1 | | | | | SL-1/SL-7 | 2,000/450 |
| Example 14 | A-15 | 41 | B-10 | 8 | C-11 | 1 | | | | | SL-1/SL-7 | 2,000/450 |
| Example 15 | A-11 | 40 | B-9 | 8 | C-6 | 1 | Q-1 | 1 | | | SL-1/SL-3 | 2,000/450 |
| Example 16 | A-9 | 43 | B-6 | 5 | C-9 | 1 | | | W-6 | 1 | SL-1/SL-2/SL-5 | 2,200/150/100 |
| Example 17 | A-14 | 40 | B-6 | 9 | C-10 | 1 | | | | | SL-1/SL-2 | 2,200/250 |
| Example 18 | A-6 | 38 | B-6 | 10 | C-6/C-9 | 1/1 | | | | | SL-1/SL-2 | 2,200/250 |
| Example 19 | A-13 | 36 | B-3 | 11 | C-9 | 2 | | | W-4 | 1 | SL-1/SL-4 | 2,100/350 |
| Example 20 | A-3 | 42 | B-6 | 7 | C-5 | 1 | | | | | SL-1/SL-2 | 2,200/250 |
| Example 21 | A-6 | 41 | B-6 | 8 | C-14 | 1 | | | | | SL-1/SL-8 | 2,200/250 |
| Example 22 | A-10 | 38 | B-5 | 10 | C-8 | 1 | | | W-3 | 1 | SL-1/SL-2 | 2,200/250 |
| Example 23 | A-6 | 40 | B-6 | 9 | C-16 | 1 | | | | | SL-1/SL-3 | 2,000/450 |
| Example 24 | A-12 | 41 | B-4 | 8 | C-1 | 1 | | | | | SL-1/SL-2 | 2,200/250 |
| Example 25 | A-4 | 37 | B-6 | 12 | C-15 | 1 | | | | | SL-1/SL-8 | 2,200/250 |
| Example 26 | A-4 | 39 | B-11 | 10 | C-7 | 1 | | | | | SL-1/SL-2 | 2,200/250 |
| Example 27 | A-6 | 43 | B-3 | 6 | C-6 | 1 | | | | | SL-1/SL-2 | 2,200/250 |
| Example 28 | A-16 | 49 | | | C-1 | 1 | | | | | SL-1/SL-3 | 2,000/450 |
| Example 29 | A-17 | 42 | B-6 | 7 | C-5 | 1 | | | | | SL-1/SL-8 | 2,200/250 |

TABLE 1-continued

| | | Resin (A) | | Acid generator (B) | | Compound (C) | | Basic compound (C') | | Surfactant | | Solvent (D) | |
|---|---|---|---|---|---|---|---|---|---|---|---|---|---|
| | | Compound No. | Parts by mass | Compound No. | Parts by mass | Compound No. | Parts by mass | Compound No. | Parts by mass | Compound No. | Parts by mass | Compound No. | Parts by mass |
| Comparative Example | 1 | A-6 | 42 | B-6 | 7 | | | Q-1 | 1 | | | SL-1/SL-2 | 2,200/250 |
| Comparative Example | 2 | A-18 | 43 | B-6 | 6 | C-6 | 1 | | | | | SL-1/SL-2 | 2,200/250 |

Example 1 to 29 and Comparative Examples 1 and 2 (Extreme. Ultraviolet Rays (EUV) Exposure and Organic Solvent Development)

An organic antireflection film, ARC29SR (manufactured by Nissan Chemical Industries, Ltd.), was coated on a silicon wafer, and baked at 205° C. for 60 seconds to form an antireflection film having a film thickness of 86 nm. Then, the resist composition prepared above was coated thereon and baked (PB) at 120° C. for 60 seconds to form a resist film having a film thickness of 50 nm. The wafer having the resist film coated thereon was subjected to pattern exposure through an exposure mask (line/space=1/1), using an EUV exposure device (Micro Exposure Tool manufactured by Exitech, NA0.3, Quadrupole, outer sigma 0.68, inner sigma 0.36). After irradiation, the wafer was heated on a hot plate at 120° C. for 60 seconds, developed by paddling with a developer (butyl acetate) for 30 seconds, rotated at a rotation speed of 2,000 rpm for 30 seconds, and then baked at 100° C. for 60 seconds to obtain a 1:1 line-and-space pattern having a line width of 30 nm.

[Evaluation of Resist Pattern/EUV]

Performance evaluation of the resist pattern was carried out, using a scanning electron microscope. For the pattern formed using the EUV exposure, performance evaluation was carried out, using a scanning electron microscope (S-9380II manufactured by Hitachi, Ltd.).

<Sensitivity>

The irradiation energy at a time when the 1:1 line-and-space pattern having a line width of 30 nm was resolved was taken as sensitivity (Eop). A smaller value thereof indicates better performance.

<Line Width Roughness (LWR)>

With regard to the line width roughness, in the Eop, the line widths at arbitrary 50 points having a size of 0.5 μm in the longitudinal direction of a 1:1 line-and-space pattern having a line width of 30 nm were measured, the standard deviation thereof was determined, and 3σ was calculated. A smaller value thereof indicates better performance.

<Evaluation of Pattern Shape (Notched Shape of Lower Part of Pattern)>

In the Eop, the 1:1 line-and-space pattern having a line width of 30 nm was observed using a scanning electron microscope (S4800 manufactured by Hitachi, Ltd.) and a notch was not seen in the lower part of the resist pattern. Thus, a case where the line width of the lower part of the pattern is from 99% to 101% with respect to the line width of the upper part of the pattern was denoted as A, a case where a notch is slightly seen in the lower part of the resist pattern, but the line width of the lower part of the pattern is in the range of 90% or more and less than 99% with respect to the line width of the upper part of the pattern was denoted as B, and a case where a notch is seen in the lower part of the resist pattern, but the line width of the lower part of the pattern is in the range of less than 90% with respect to the line width of the upper part of the pattern was denoted as C. The results are shown in Table 2.

Moreover, the line width of the lower part of the pattern means the line width of a resist pattern at a height of 0.1×T from the surface of a substrate in a case where the height of the resist pattern from the surface of the substrate (in a case where the height of the resist pattern is not uniform, the maximum height of the resist pattern from the surface of the substrate) is defined as T. In addition, the line width of the upper part of the pattern means the line width of a resist pattern at a height of 0.9×T from the surface of a substrate.

<Development Defects>

With regard to the obtained pattern, development defects were detected using a defect inspecting apparatus UVision (product name) manufactured by Applied Materials, Inc. under the conditions of a pixel size of 120 nm, a light source polarization Horizontal, and a detection mode Gray Field. The number of development defects per unit area (number/cm$^2$) was calculated and evaluation of the development defect performance was carried out using the following criteria.

A (Particularly good) . . . A case where the value is less than 0.5

B (Good) . . . A case where the value is 0.5 or more and less than 1.0

C (Slightly defective) . . . A case where the value is 1.0 or more and less than 2.0

C (Defective) . . . A case where the value is 2.0 or more

TABLE 2

| | Evaluation results of line-and-space performance | | |
|---|---|---|---|
| | LWR | Development defects | Pattern shape |
| Example 1 | 3.3 | A | A |
| Example 2 | 2.6 | A | A |
| Example 3 | 3.0 | B | B |
| Example 4 | 3.1 | A | B |
| Example 5 | 3.0 | B | A |
| Example 6 | 3.4 | A | B |
| Example 7 | 2.8 | A | A |
| Example 8 | 3.4 | A | A |
| Example 9 | 3.3 | A | B |
| Example 10 | 3.3 | A | B |
| Example 11 | 3.3 | B | A |
| Example 12 | 3.1 | B | A |
| Example 13 | 3.5 | A | A |
| Example 14 | 3.6 | A | B |
| Example 15 | 2.8 | A | A |
| Example 16 | 3.3 | B | B |
| Example 17 | 3.3 | B | B |
| Example 18 | 2.8 | A | B |
| Example 19 | 3.1 | A | A |

TABLE 2-continued

| | Evaluation results of line-and-space performance | | |
|---|---|---|---|
| | LWR | Development defects | Pattern shape |
| Example 20 | 3.1 | B | A |
| Example 21 | 2.9 | B | A |
| Example 22 | 3.2 | A | A |
| Example 23 | 3.2 | B | A |
| Example 24 | 3.3 | A | A |
| Example 25 | 2.9 | A | A |
| Example 26 | 3.3 | B | B |
| Example 27 | 3.1 | B | B |
| Example 28 | 2.7 | B | A |
| Example 29 | 3.6 | B | A |
| Comparative Example 1 | 3.8 | D | B |
| Comparative Example 2 | 3.9 | B | C |

From Tables 1 and 2, it is found that for the patterns of Examples formed by the pattern forming method using the composition containing the resin (A), the acid generator (B), and the compound (C) in the present invention, LWR was small, there were fewer development defects, and the shapes were excellent, as compared with Comparative Example 1 not using the compound (C) and Comparative Example 2 not using the resin (A) (not having a repeating unit having a phenolic hydroxyl group). Further, Example 28 was an embodiment in which a repeating unit that generates an acid upon irradiation with active light or radiation was included in the resin (A-16), and the acid generator (B) was incorporated into a part of the resin (A).

INDUSTRIAL APPLICABILITY

By the pattern forming method of the present invention, all of line width roughness performance, suppression of development defects, and pattern shapes can be accomplished to extremely high levels, in particular, in formation of an ultrafine pattern (for example, having a line width of 50 nm or less).

The present invention has been described in detail and with reference to specific embodiments, and it is apparent to those skilled in the art that various modifications and changes are possible without departing from the spirit and the scope of the invention.

This application is based on Japanese Patent Application (Japanese Patent Application No. 2014-178217) filed on Sep. 2, 2014, and the contents thereof are incorporated herein by reference.

What is claimed is:

1. A pattern forming method comprising:
   (1) a step of forming a film with an active-light-sensitive or radiation-sensitive resin composition containing the following (A) to (C):
   (A) a resin having a repeating unit having a phenolic hydroxyl group, and having a group that decomposes by the action of an acid to generate a polar group,
   (B) a compound that generates an acid upon irradiation with active light or radiation, and
   (C) a compound having a cationic site and an anionic site in the same molecule, in which the cationic site and the anionic site are linked to each other via a covalent bond;
   (2) a step of exposing the film; and
   (3) a step of developing the exposed film using a developer including an organic solvent to form a negative tone pattern,
   wherein the compound (C) is a compound represented by the following General Formula (C-1):

$$(Rx)_{n2}\text{-}X^{\oplus}\text{-L-}A^{\ominus} \quad (C\text{-}1)$$

in which $A^-$ represents an organic acid anion, L represents a single bond or a divalent linking group, and $X^+$ represents a nitrogen cation or an iodine cation;
Rx represents an alkyl group, a cycloalkyl group, an aryl group, an aralkyl group, or a heterocyclic group, in a case where Rx's are present in plural numbers, a plurality of Rx's may be the same as or different from each other, and at least one of n2 Rx's has 5 or more carbon atoms; and
in a case where $X^+$ represents a nitrogen cation, n2 represents 3, and in a case where $X^+$ represents an iodine cation, n2 represents 1.

2. The pattern forming method according to claim 1, wherein $A^-$ represents a carboxylate anion.

3. The pattern forming method according to claim 1, wherein $X^+$ represents a nitrogen cation.

4. The pattern forming method according to claim 1, wherein Rx represents an alkyl group.

5. The pattern forming method according to claim 1, wherein at least one of n2 Rx's has 3 or more carbon atoms.

6. The pattern forming method according to claim 1, wherein the number of carbon atoms present between $X^+$ and the element having negative charge among the elements constituting $A^-$ is 5 or less.

7. The pattern forming method according to claim 1, wherein the content of the compound (C) is 5% by mass or less with respect to the total solid content of the active-light-sensitive or radiation-sensitive resin composition.

8. The pattern forming method according to claim 1, wherein the divalent linking group of L is an alkylene group, a cycloalkylene group, an arylene group, or a group composed of a combination of two or more of these groups.

9. The pattern forming method according to claim 1, wherein Rx represents an alkyl group having 5 to 10 carbon atoms.

10. The pattern forming method according to claim 1, wherein Rx represents an alkyl group having 6 to 8 carbon atoms.

11. The pattern forming method according to claim 1, wherein the number of carbon atoms present between $X^+$ and the element having negative charge among the elements constituting $A^-$ is from 0 to 3.

12. The pattern forming method according to claim 1, wherein the content of the compound (C) is 1 to 4% by mass, with respect to the total solids content of the active-light-sensitive or radiation-sensitive resin composition.

13. The pattern forming method according to claim 1, wherein the compound (C) is any one of (C-1), (C-3), (C-6), (C-7), (C-9), (C-11), (C-13), (C-14), (C-16):

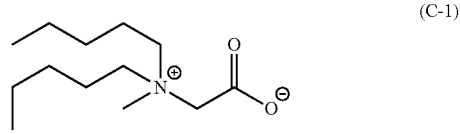

(C-1)

-continued

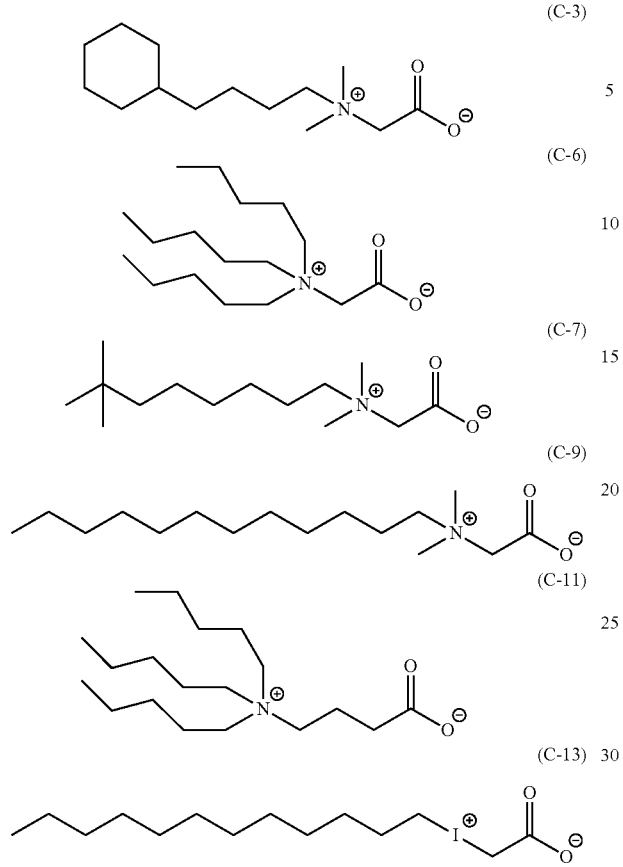

(C-3)
(C-6)
(C-7)
(C-9)
(C-11)
(C-13)

-continued

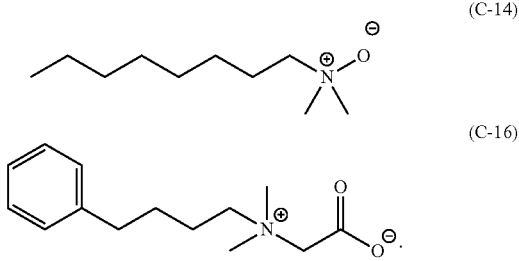

(C-14)
(C-16)

14. A method for manufacturing an electronic device, comprising
  (1) a step of forming a film on an inorganic substrate or a coating type inorganic substrate suitable for use in a process of producing a semiconductor, a circuit board for a liquid crystal device or a thermal head with an active-light-sensitive or radiation-sensitive resin composition containing the following (A) to (C):
  (A) a resin having a repeating unit having a phenolic hydroxyl group, and having a group that decomposes by the action of an acid to generate a polar group,
  (B) a compound that generates an acid upon irradiation with active light or radiation, and
  (C) a compound having a cationic site and an anionic site in the same molecule, in which the cationic site and the anionic site are linked to each other via a covalent bond;
  (2) a step of exposing the film; and
  (3) a step of developing the exposed film using a developer including an organic solvent to form a negative tone pattern.

* * * * *